US009169472B2

(12) United States Patent
Briers et al.

(10) Patent No.: US 9,169,472 B2
(45) Date of Patent: Oct. 27, 2015

(54) ENDOLYSIN OBPGPLYS

(71) Applicants: LYSANDO AG, Triesenberg (LI); KATHOLIEKE UNIVERSITEIT LEUVEN, K.U. LEUVEN R&D, Leuven (BE)

(72) Inventors: Yves Briers, Rohr (CH); Rob Lavigne, Merksem (BE); Maarten Walmagh, Herk-de-Stad (BE); Stefan Miller, Regensburg (DE)

(73) Assignees: LYSANDO AG, Triesenberg (LI); KATHOLIEKE UNIVERSITEIT LEUVEN, K.U. LEUVEN R&D, Leuven (BE)

( * ) Notice: Subject to any disclaimer, the term of this patent is extended or adjusted under 35 U.S.C. 154(b) by 0 days.

(21) Appl. No.: 14/475,900

(22) Filed: Sep. 3, 2014

(65) Prior Publication Data

US 2015/0024469 A1 Jan. 22, 2015

Related U.S. Application Data

(62) Division of application No. 13/390,033, filed as application No. PCT/EP2010/062351 on Aug. 24, 2010, now Pat. No. 8,846,865.

(30) Foreign Application Priority Data

Aug. 24, 2009 (EP) .................................... 09168527

(51) Int. Cl.

| | |
|---|---|
| ***C12N 9/26*** | (2006.01) |
| ***C12N 15/00*** | (2006.01) |
| ***C12N 5/10*** | (2006.01) |
| ***A61K 38/46*** | (2006.01) |
| ***C12N 9/36*** | (2006.01) |
| ***C07K 14/195*** | (2006.01) |
| *A61K 38/00* | (2006.01) |

(52) U.S. Cl.

CPC ............ *C12N 9/2462* (2013.01); *C07K 14/195* (2013.01); *C12Y 302/01017* (2013.01); *A61K 38/00* (2013.01); *C07K 2319/21* (2013.01); *C07K 2319/55* (2013.01)

(58) Field of Classification Search

None

See application file for complete search history.

(56) References Cited

U.S. PATENT DOCUMENTS

| | | | |
|---|---|---|---|
| 7,572,602 | B1 | 8/2009 | Donovan |
| 2011/0027249 | A1 | 2/2011 | Donovan |
| 2011/0243915 | A1 | 10/2011 | Briers et al. |

FOREIGN PATENT DOCUMENTS

| | | |
|---|---|---|
| EP | 0 510 907 | 10/1992 |
| WO | WO 2010/023207 | 3/2010 |
| WO | WO 2010/149792 | 12/2010 |
| WO | WO 2010/149795 | 12/2010 |

OTHER PUBLICATIONS

"Miscellaneous Peptides", Sigma Catalog, p. 1089, 1997.

Arima et al., "Bactericidal action of lysozymes attached with various sizes of hydrophobic peptides to the C-terminal using genetic modification," *FEBS Letters*, 415(1):114-118, 1997.

Loessner, "Bacteriophage endolysins—current state of research and applications," *Current Opinion in Microbiology*, 8(4):480-487, 2005.

Office Action issued in U.S. Appl. No. 13/390,033, mailed Jul. 25, 2013.

Office Action issued in U.S. Appl. No. 13/390,033, mailed Mar. 10, 2014.

Orito et al., "*Bacillus amyloliquefaciens* phage endolysin can enhance permeability of *Pseudomonas aeruginosa* outer membrane and induce cell lysis," *Applied Microbiology and Biotechnology*, 6591):105-109, 2004.

PCT International Preliminary Report on Patentability issued in International application No. PCT/EP2010/062351, dated Mar. 8, 2012.

PCT International Search Report and Written Opinion issued in International application No. PCT/EP2010/062351, dated Nov. 11, 2010.

*Primary Examiner* — David J Steadman

(74) *Attorney, Agent, or Firm* — Parker Highlander PLLC

(57) ABSTRACT

The present invention relates to a polypeptide with an amino acid sequence according to SEQ ID NO: 1 and fragments or derivatives thereof. The present invention further relates to fusion proteins comprising said polypeptide and an additional peptide stretch fused to said polypeptide at the N- or C-terminus. Moreover, the present invention relates to nucleic acid molecules encoding said polypeptide or fusion protein, vectors comprising said nucleic acid molecules and host cells comprising either said nucleic acid molecules or said vectors. In addition, the present invention relates to said polypeptide or fusion protein for use as a medicament, in particular for the treatment or prevention of Gram-negative bacterial infections, as diagnostic means, as cosmetic substance or as sanitizing agent. The present invention also relates to the use of said polypeptide or fusion protein for the treatment or prevention of Gram-negative bacterial contamination of foodstuff, of food processing equipment, of food processing plants, of surfaces coming into contact with foodstuff, of medical devices, of surfaces in hospitals and surgeries. Furthermore, the present invention relates to a pharmaceutical composition comprising said polypeptide or fusion protein.

15 Claims, 6 Drawing Sheets

MKNSEKNASIIMSIQRTLASLSLYGGRIDGLFGEKCRGAIILMLNKVYPNFSTNKLPSNTYE
AESVFTFLQTALAGVGLYTITIDGKWGGTSQGAIDALVKSYRQITEAERAGSTLPLGLATVM
SKHMSIEQLRAMLPTDRQGYAEVYIDPLNETMDIFEINTPLRIAHFMAQILHETACFKYTEE
LASGKAYEGRADLGNTRPGDGPLFKGRGLLQITGRLNYVKCQVYLREKLKDPTFDITSSVTC
AQQLSESPLLAALASGYFWRFIKPKLNETADKDDIYWVSVYVNGYAKQANPYYPNRDKEPNH
MKERVQMLAVTKKALGIV (B)

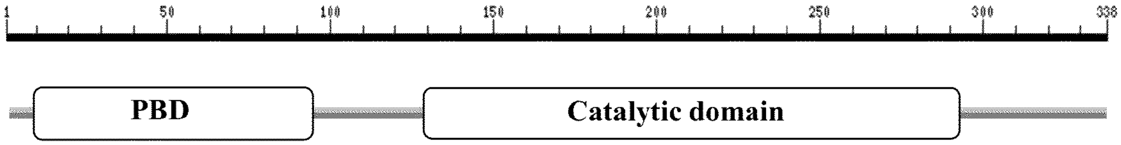

FIG. 2

ATGAAAAATAGCGAGAAGAATGCATCGATAATTATGTCGATACAGAGAACGCTCGCTTCACT
CTCACTCTATGGAGGCCGCATCGACGGCCTCTTTGGAGAGAAGTGTCGTGGGGCTATCATCT
TGATGCTGAATAAGGTCTATCCTAATTTCAGCACCAACAAACTTCCGAGTAACACATATGAA
GCGGAATCCGTGTTCACGTTTCTCCAGACTGCTTTGGCTGGTGTTGGTCTTTATACCATTAC
TATTGATGGTAAATGGGGTGGTACTTCTCAAGGTGCTATTGACGCCCTCGTCAAGTCTTACC
GTCAAATTACCGAAGCGGAGCGAGCTGGGTCGACGTTGCCATTAGGTCTTGCTACTGTGATG
TCTAAGCATATGTCTATTGAACAGTTGAGAGCAATGCTCCCTACCGATAGACAAGGATATGC
TGAAGTTTATATCGATCCTTTAAATGAGACGATGGATATATTTGAAATAAATACTCCATTAC
GAATTGCTCATTTCATGGCCCAAATCCTCCACGAAACGGCGTGTTTTAAATATACCGAAGAA
CTGGCGAGCGGTAAGGCTTATGAGGGTCGTGCTGATTTAGGTAATACTCGACCAGGTGATGG
ACCACTGTTTAAAGGTCGTGGATTATTACAAATTACCGGGCGACTGAATTATGTGAAATGCC
AAGTGTATTTGAGAGAGAAGTTAAAGGACCCTACTTTCGACATTACGTCGTCTGTAACTTGT
GCCCAACAGCTCTCCGAAAGTCCACTTCTTGCTGCATTGGCATCGGGCTACTTCTGGAGATT
CATCAAACCTAAACTCAATGAAACGGCTGATAAAGACGATATCTATTGGGTTTCTGTTTATG
TCAATGGTTACGCTAAACAAGCGAATCCTTATTACCCTAACCGGGATAAGGAACCCAACCAT
ATGAAAGAACGTGTCCAAATGCTTGCAGTGACAAAGAAAGCACACGGAATAGTTTAA

FIG. 3

```
ATGAAAAATAGCGAGAAGAATGCATCGATAATTATGTCGATACAGAGAACGCTCGCTTCACT
CTCACTCTATGGAGGCCGCATCGACGGCCTCTTTGGAGAGAAGTGTCGTGGGGCTATCATCT
TGATGCTGAATAAGGTCTATCCTAATTTCAGCACCAACAAACTTCCGAGTAACACATATGAA
GCGGAATCCGTGTTCACGTTTCTCCAGACTGCTTTGGCTGGTGTTGGTCTTTATACCATTAC
TATTGATGGTAAATGGGGTGGTACTTCTCAAGGTGCTATTGACGCCCTCGTCAAGTCTTACC
GTCAAATTACCGAAGCGGAGCGAGCTGGGTCGACGTTGCCATTAGGTCTTGCTACTGTGATG
TCTAAGCATATGTCTATTGAACAGTTGAGAGCAATGCTCCCTACCGATAGACAAGGATATGC
TGAAGTTTATATCGATCCTTTAAATGAGACGATGGATATATTTGAAATAAATACTCCATTAC
GAATTGCTCATTTCATGGCCCAAATCCTCCACGAAACGGCGTGTTTTAAATATACCGAAGAA
CTGGCGAGCGGTAAGGCTTATGAGGGTCGTGCTGATTTAGGTAATACTCGACCAGGTGATGG
ACCACTGTTTAAAGGTCGTGGATTATTACAAATTACCGGGCGACTGAATTATGTGAAATGCC
AAGTGTATTTGAGAGAGAAGTTAAAGGACCCTACTTTCGACATTACGTCGTCTGTAACTTGT
GCCCAACAGCTCTCCGAAAGTCCACTTCTTGCTGCATTGGCATCGGGCTACTTCTGGAGATT
CATCAAACCTAAACTCAATGAAACGGCTGATAAAGACGATATCTATTGGGTTTCTGTTTATG
TCAATGGTTACGCTAAACAAGCGAATCCTTATTACCCTAACCGGGATAAGGAACCCAACCAT
ATGAAAGAACGTGTCCAAATGCTTGCAGTGACAAAGAAAGCACTCGGAATAGTT
```

FIG. 4A

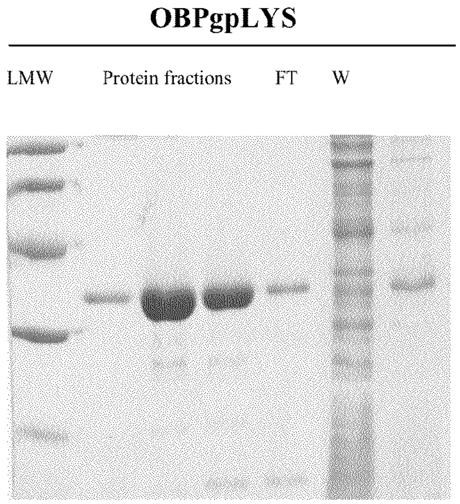

FIG. 4B

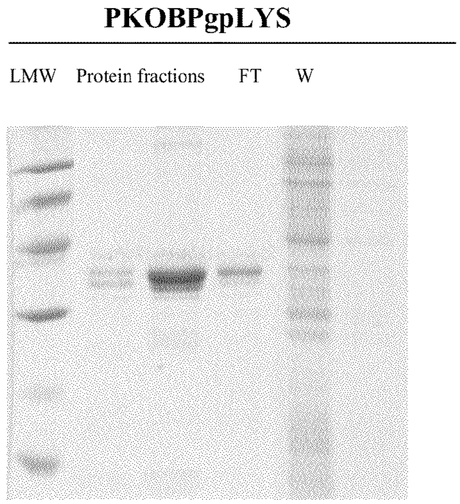

ENDOLYSIN OBPGPLYS

This application is divisional of U.S. application Ser. No. 13/390,033, which was filed as a national phase application under 35 U.S.C. §371 of International Application No. PCT/EP2010/062351 filed 24 Aug. 2010, which claims priority to European Application No. 09 168 527.1 filed on 24 Aug. 2009. The entire text of each of the above-referenced disclosures is specifically incorporated herein by reference without disclaimer.

The sequence listing that is contained in the file named "DEBEP0112USD1_ST25.txt", which is 139 KB (as measured in Microsoft Windows®) and was created on Aug. 19, 2014, is filed herewith by electronic submission and is incorporated by reference herein.

BACKGROUND OF THE INVENTION

1. Field of the Invention

The present invention relates to a polypeptide with an amino acid sequence according to SEQ ID NO: 1 and fragments or derivatives thereof. The present invention further relates to fusion proteins comprising said polypeptide and an additional peptide stretch fused to said polypeptide at the N- or C-terminus. Moreover, the present invention relates to nucleic acid molecules encoding said polypeptide or fusion protein, vectors comprising said nucleic acid molecules and host cells comprising either said nucleic acid molecules or said vectors. In addition, the present invention relates to said polypeptide or fusion protein for use as a medicament, in particular for the treatment or prevention of Gram-negative bacterial infections, as diagnostic means, as cosmetic substance or as sanitizing agent. The present invention also relates to the use of said polypeptide or fusion protein for the treatment or prevention of Gram-negative bacterial contamination of foodstuff, of food processing equipment, of food processing plants, of surfaces coming into contact with foodstuff, of medical devices, of surfaces in hospitals and surgeries. Furthermore, the present invention relates to a pharmaceutical composition comprising said polypeptide or fusion protein.

2. Description of Related Art

Gram-negative bacteria possess an outer membrane, with its characteristic asymmetric bilayer as a hallmark. The outer membrane bilayer consists of an inner monolayer containing phospholipids (primarily phosphatidyl ethanolamine) and an outer monolayer that is mainly composed of a single glycolipid, lipopolysaccharide (LPS). There is an immense diversity of LPS structures in the bacterial kingdom and the LPS structure may be modified in response to prevailing environmental conditions. The stability of the LPS layer and interaction between different LPS molecules is mainly achieved by the electrostatic interaction of divalent ions ($Mg^{2+}$, $Ca^{2+}$) with the anionic components of the LPS molecule (phosphate groups in the lipid A and the inner core and carboxyl groups of KDO). Furthermore, the dense and ordered packing of the hydrophobic moiety of lipid A, favored by the absence of unsaturated fatty acids, forms a rigid structure with high viscosity. This makes it less permeable for lipophilic molecules and confers additional stability to the outer membrane (OM).

Various types of agents having bactericidal or bacteriostatic activity are known, e.g. antibiotics, endolysins, antimicrobial peptides and defensins. Increasingly microbial resistance to antibiotics, however, is creating difficulties in treating more and more infections caused by bacteria. Particular difficulties arise with infections caused by Gram-negative bacteria like *Pseudomonas aeruginosa* and Enterobacteriaceae.

Endolysins are peptidoglycan hydrolases encoded by bacteriophages (or bacterial viruses). They are synthesized during late gene expression in the lytic cycle of phage multiplication and mediate the release of progeny virions from infected cells through degradation of the bacterial peptidoglycan. They are either β(1,4)-glycosylases (lysozymes), transglycosylases, amidases or endopeptidases. Antimicrobial application of endolysins was already suggested in 1991 by Gasson (GB2243611). Although the killing capacity of endolysins has been known for a long time, the use of these enzymes as antibacterials was ignored due to the success and dominance of antibiotics. Only after the appearance of multiple antibiotic resistant bacteria this simple concept of combating human pathogens with endolysins received interest. A compelling need to develop totally new classes of antibacterial agents emerged and endolysins used as 'enzybiotics'—a hybrid term of 'enzymes' and 'antibiotics'—perfectly met this need. In 2001, Fischetti and coworkers demonstrated for the first time the therapeutic potential of bacteriophage Cl endolysin towards group A streptococci (Nelson et al., 2001). Since then many publications have established endolysins as an attractive and complementary alternative to control bacterial infections, particularly by Gram positive bacteria. Subsequently different endolysins against other Gram positive pathogens such as *Streptococcus pneumoniae* (Loeffler et al., 2001), *Bacillus anthracis* (Schuch et al., 2002), *S. agalactiae* (Cheng et al., 2005) and *Staphylococcus aureus* (Rashel et al, 2007) have proven their efficacy as enzybiotics. Nowadays, the most important challenge of endolysin therapy lies in the insensitivity of Gram-negative bacteria towards the exogenous action of endolysins, since the outer membrane shields the access of endolysins from the peptidoglycan. This currently prevents the expansion of the range of effective endolysins to important Gram-negative pathogens.

Antimicrobial peptides (AMPs) represent a wide range of short, cationic or amphipatic, gene encoded peptide antibiotics that can be found in virtually every organism. Different AMPs display different properties, and many peptides in this class are being intensively researched not only as antibiotics, but also as templates for cell penetrating peptides. Despite sharing a few common features (e.g., cationicity, amphipathicity and short size), AMP sequences vary greatly, and at least four structural groups (α-helical, β-sheet, extended and looped) have been proposed to accommodate the diversity of the observed AMP conformations. Likewise, several modes of action as antibiotics have been proposed, and it was shown e.g. that the primary target of many of these peptides is the cell membrane whereas for other peptides the primary target is cytoplasmic invasion and disruption of core metabolic functions. AMPs may become concentrated enough to exhibit cooperative activity despite the absence of specific target binding; for example, by forming a pore in the membrane, as is the case for most AMPs. However, this phenomenon has only been observed in model phospholipid bilayers, and in some cases, AMP concentrations in the membrane that were as high as one peptide molecule per six phospholipid molecules were required for these events to occur. These concentrations are close to, if not at, full membrane saturation. As the minimum inhibitory concentration (MIC) for AMPs are typically in the low micromolar range, scepticism has understandably arisen regarding the relevance of these thresholds and their importance in vivo (Melo et al., Nature reviews, Microbiology, 2009, 245).

Defensins are a large family of small, cationic, cysteine- and arginine-rich antimicrobial peptides, found in both vertebrates and invertebrates. Defensins are divided into five groups according to the spacing pattern of cysteines: plant, invertebrate, α-, β-, and θ-defensins. The latter three are mostly found in mammals. α-defensins are proteins found in neutrophils and intestinal epithelia. β-defensins are the most widely distributed and are secreted by leukocytes and epithelial cells of many kinds. θ-defensins have been rarely found so far e.g. in leukocytes of rhesus macaques. Defensins are active against bacteria, fungi and many enveloped and non-enveloped viruses. However, the concentrations needed for efficient killing of bacteria are mostly high, i.e. in the micromolar range. Activity of many peptides may be limited in presence of physiological salt conditions, divalent cations and serum. Depending on the content of hydrophobic amino acid residues defensins also show haemolytic activity.

BRIEF SUMMARY OF THE INVENTION

Thus, there is a need for new antimicrobial agents against Gram-negative bacteria.

This object is solved by the subject matter defined in the claims.

BRIEF DESCRIPTION OF THE DRAWINGS

The following figures serve to illustrate the invention.

FIG. 1 shows the endolysin OBPgpLYS according to the present invention. In (A) the amino acid sequence of the endolysin OBPgpLYS (SEQ ID NO: 1) according to the present invention is depicted. In (B) the primary structure of the OBPgpLYS comprising an additional $His_6$-tag is given showing the results of a functional analysis using BLASTp and Pfam analysis. The predicted N-terminal peptidoglycan binding domain (PBD, amino acid residues 7-96) is underlined and the C-terminal catalytic domain (amino acid residues 126-292) of the lysozyme-like superfamily is written in italics. The complete amino acid sequence of the OBPgpLYS comprising an additional $His_6$-tag at the C-terminus shown in (B) is depicted in SEQ ID NO: 47.

FIG. 2 shows the nucleotide sequence (SEQ ID NO: 101) of the endolysin of phage OBP.

FIG. 3 shows the nucleotide sequence (SEQ ID NO: 3) of the endolysin OBPgpLYS (SEQ ID NO: 1) according to the present invention.

FIGS. 4A-4B show pictures of a Coomassie-stained SDS-PAGE showing the results of the expression and purification of the unmodified endolysin OBPgpLYS (4A, SEQ ID NO: 47) and its modified endolysin variant PKOBPgpLYS (4B, SEQ ID NO: 49). The lane LMW pertains to a size marker (LMW ladder). The following three lanes pertain to protein fractions of the purified protein in Elution Buffer (20 mM $NaH_2P0_4$—NaOH pH7.4; 0.5 M NaCl; 500 mM imidazole) after $Ni^{2+}$ affinity chromatography. The lane FT pertains to the flow through and the lane W to waste fractions. Only minor secondary bands are visible in the purified protein fractions, indicating the high purity of the recombinant protein (>90%).

In FIG. 5A the antibacterial activity on *Escherichia coli* WK 6 cells is represented, in FIG. 5B the antibacterial activity on *Salmonella typhimurium* LT2 (SGSC No 2317) cells, in FIG. 5C the antibacterial activity on *Pseudomonas aeruginosa* PAO1p cells, in FIG. 5D the antibacterial activity on *Pseudomonas aeruginosa* Br667 cells, in FIG. 5E the antibacterial activity on *Pseudomonas putida* G1 cells and in FIG. 5F the antibacterial activity on *Burkholderia pseudomallei* cells. "Δ" gives the difference of antibacterial activity between the respective OBPgpLYS and PKOBPgpLYS samples. The error bars render the standard deviations of the mean.

DETAILED DESCRIPTION OF THE INVENTION

Figure 5A:
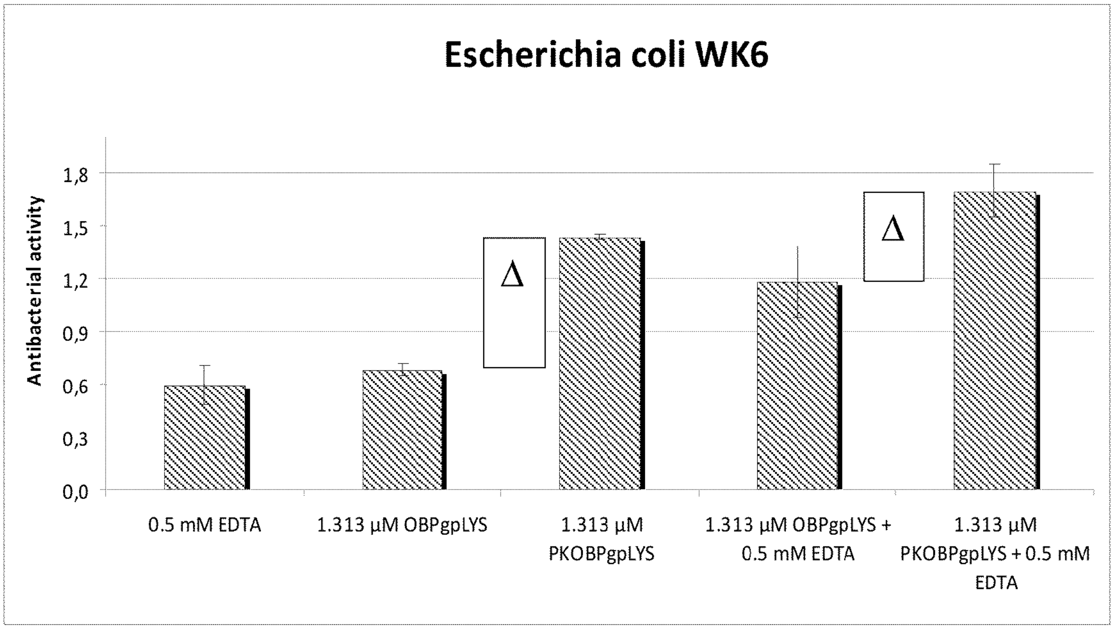
FIGS. 5A-5F show in a graphic representation the antibacterial activities of different compositions of unmodified OBPgpLYS (SEQ ID NO: 47) and the modified PKOBPgpLYS (SEQ ID NO: 49) on several exponential growing Gram-negative bacteria after an incubation at room temperature and without shaking. Each species of Gram-negative bacteria was incubated for 30 minutes with a composition comprising 0.5 mM EDTA but no endolysin, with a composition comprising 1.315 μM unmodified OBPgpLYS but no EDTA, with a composition comprising 1.315 μM modified PKOBPgpLYS but no EDTA, with a composition comprising 1.315 μM unmodified OBPgpLYS and 0.5 mM EDTA and with a composition comprising 1.315 μM modified PKOBPgpLYS and 0.5 mM EDTA.

The term "protein" as used herein refers synonymously to the term "polypeptide". The term "protein" as used herein refers to a linear polymer of amino acid residues linked by peptide bonds in a specific sequence. The amino-acid residues of a protein may be modified by e.g. covalent attachments of various groups such as carbohydrates and phosphate. Other substances may be more loosely associated with the polypeptide chains, such as heme or lipid, giving rise to the conjugated proteins which are also comprised by the term "protein" as used herein. The various ways in which the polypeptide chains fold have been elucidated, in particular with regard to the presence of alpha helices and beta-pleated sheets. The term "protein" as used herein refers to all four classes of proteins being all-alpha, all-beta, alpha/beta and alpha plus beta.

The term "fusion protein" as used herein refers to an expression product resulting from the fusion of two nucleic acid sequences. Such a protein may be produced, e.g., in recombinant DNA expression systems. Moreover, the term "fusion protein" as used herein refers to a fusion of a first amino acid sequence as e.g. an endolysin, with a second or further amino acid sequence. The second or further amino acid sequence is preferably a peptide stretch, in particular a cationic peptide, a polycationic peptide, an amphipatic peptide, a sushi peptide, a defensin, a hydrophobic peptide or an antimicrobial peptide. Preferably, said second and/or further amino acid sequence is foreign to and not substantially homologous with any domain of the first amino acid sequence.

The term "peptide stretch" as used herein refers to any kind of peptide linked to a protein such as an endolysin. In particular the term "peptide stretch" as used herein refers to a cationic peptide, a polycationic peptide, an amphipatic peptide, a sushi peptide, a defensin, a hydrophobic peptide and/or an antimicrobial peptide. However, a peptide stretch in the meaning of the present invention does not refer to $His_6$-tags, Strep-tags, Avi-tags, Myc-tags, Gst-tags, JS-tags, cystein-tags, FLAG-tags or other tags known in the art, thioredoxin or maltose binding proteins (MBP).

The term "tag" in contrast to the term "peptide stretch" as used herein refers to a peptide which can be useful to facilitate expression and/or affinity purification of a polypeptide, to immobilize a polypeptide to a surface or to serve as a marker or a label moiety for detection of a polypeptide e.g. by antibody binding in different ELISA assay formats as long as the function making the tag useful for one of the above listed facilitation is not caused by the positively charge of said peptide. However, the $His_6$-tag may, depending on the respective pH, also be positively charged, but is used as affinity purification tool as it binds to immobilized divalent cations and is not used as a peptide stretch according to the present invention.

The term "peptide" as used herein refers to short polypeptides consisting of from about 2 to about 100 amino acid residues, more preferably from about 4 to about 50 amino acid residues, more preferably from about 5 to about 30 amino acid residues, wherein the amino group of one amino acid residue is linked to the carboxyl group of another amino acid residue by a peptide bond. A peptide may have a specific function. A peptide can be a naturally occurring peptide or a synthetically designed and produced peptide. The peptide can be, for example, derived or removed from a native protein by enzymatic or chemical cleavage, or can be prepared using conventional peptide synthesis techniques (e.g., solid phase synthesis) or molecular biology techniques (see Sambrook, J. et al., Molecular Cloning: A Laboratory Manual, Cold Spring Harbor Press, Cold Spring Harbor, N.Y. (1989)). Preferred naturally occurring peptides are e.g. antimicrobial peptides, defensins, and sushi peptides. Preferred synthetically produced peptides are e.g. polycationic, amphiphatic or hydrophobic peptides. A peptide in the meaning of the present invention does not refer to His-tags, Strep-tags, thioredoxin or maltose binding proteins (MBP) or the like, which are used to purify or locate proteins.

The term "endolysin" as used herein refers to an enzyme which is suitable to hydrolyse bacterial cell walls. "Endolysins" comprise at least one "enzymatically active domain" (EAD) having at least one of the following activities: endopeptidase, N-acetyl-muramoyl-L-alanine-amidase (amidase), N-acetyl-muramidase, N-acetyl-glucosaminidase (lysozyme) or transglycosylases. In addition, the endolysins may contain also regions which are enzymatically inactive, and bind to the cell wall of the host bacteria, the so-called CBDs (cell wall binding domains). The endolysin may contain two or more CBDs. However, the term "endolysin" as used herein refers also to enzymes having at least one EAD but no CBDs. Generally, the cell wall binding domain is able to bind different components on the surface of bacteria. Preferably, the cell wall binding domain is a peptidoglycan binding domain and binds to the bacteria's peptidoglycan structure. The different domains of an endolysin can be connected by a domain linker.

The term "domain linker" as used herein refers to an amino acid sequence functioning to connect single protein domains with one another. As a rule domain linkers form no or only few regular secondary structure like α-helices or β-sheets and can occupy different conformations with the respective structural context. Methods to detect domain linker and properties of linker sequences are well known in the art as e.g. described in Bae et al., 2005, Bioinformatics, 21, 2264-2270 or George & Heringa, 2003, Protein Engineering, 15, 871-879.

The term "wild type" or "wt" as used herein refers to the amino acid sequence of the endolysin OBPgpLYS as depicted in SEQ ID NO: 86. The nucleic acid sequence encoding the wild type endolysin OBPgpLYS is depicted in SEQ ID NO: 101.

The term "deletion" as used herein refers to the removal of 1, 2, 3, 4, 5 or more amino acid residues from the respective starting sequence.

The term "insertion" or "addition" as used herein refers to the insertion or addition of 1, 2, 3, 4, 5 or more amino acid residues to the respective starting sequence.

The term "substitution" as used herein refers to the exchange of an amino acid residue located at a certain position for a different one.

The term "cell wall" as used herein refers to all components that form the outer cell enclosure of the Gram-negative bacteria and thus guarantee their integrity. In particular, the term "cell wall" as used herein refers to peptidoglycan, the outer membrane of the Gram-negative bacteria with the lipopolysaccharide, the bacterial cell membrane, but also to additional layers deposited on the peptidoglycan as e.g. capsules, outer protein layers or slimes.

The term "EAD" as used herein refers to the enzymatically active domain of an endolysin. The EAD is responsible for hydrolysing bacterial peptidoglycans. It exhibits at least one enzymatic activity of an endolysin. The EAD can also be composed of more than one enzymatically active module. The term "EAD" is used herein synonymously with the term "catalytic domain".

As used herein, the term "cationic peptide" refers to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides.

The term "polycationic peptide" as used herein refers to a synthetically produced peptide composed of mostly positively charged amino acid residues, in particular lysine and/or arginine residues. A peptide is composed of mostly positively charged amino acid residues if at least about 20, 30, 40, 50, 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term, "antimicrobial peptide" (AMP) as used herein refers to any peptide that has microbicidal and/or microbistatic activity. Thus, the term "antimicrobial peptide" as used herein refers in particular to any peptide having anti-bacterial, anti-fungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties.

The term "defensin" as used herein refers to a peptide present within animals, preferably mammals, more preferably humans, wherein the defensin plays a role in the innate host defense system as the destruction of foreign substances such as infectious bacteria and/or infectious viruses and/or fungi. A defensin is a non-antibody microbicidal and/or tumoricidal protein, peptide or polypeptide. Examples for "defensins" are "mammalian defensins," alpha-defensins, beta-defensins, indolicidin and magainins. The term "defensins" as used herein refers both to an isolated form from animal cells or to a synthetically produced form, and refers also to variants which substantially retain the cytotoxic activities of their parent proteins, but whose sequences have been altered by insertion or deletion of one or more amino acid residues.

The term "sushi peptide" as used herein refers to complement control proteins (CCP) having short consensus repeats. The sushi module of sushi peptides functions as a protein-protein interaction domain in many different proteins. Peptides containing a Sushi domain have been shown to have antimicrobial activities.

The term "amphipathic peptide" as used herein refers to peptides having both hydrophilic and hydrophobic functional groups. Preferably, the term "amphipathic peptide" as used herein refers to a peptide having a defined arrangement of hydrophilic and hydrophobic groups e.g. amphipatic peptides may be e.g. alpha helical, having predominantly non polar side chains along one side of the helix and polar residues along the remainder of its surface.

The term "hydrophobic group" as used herein refers to chemical groups such as amino acid side chains which are substantially water insoluble, but soluble in an oil phase, with the solubility in the oil phase being higher than that in water or in an aqueous phase. In water, amino acid residues having a hydrophobic side chain interact with one another to generate a nonaqueous environment. Examples of amino acid residues with hydrophobic side chains are valine, isoleucine, leucine, methionine, phenylalanine, tryptophan, cysteine, alanine, tyrosine, histidine, threonin, serine, proline and glycine residues.

The present invention relates to new antibacterial agents against Gram-negative bacteria. In particular the present invention relates to a polypeptide comprising an amino acid sequence according to SEQ ID NO: 1 or fragments or derivatives thereof. The polypeptide comprising an amino acid sequence according to SEQ ID NO: 1 is preferably encoded by a nucleotide sequence according to SEQ ID NO: 3.

The endolysin OBPgpLYS having an amino acid sequence according to SEQ ID NO: 1 has a length of 328 amino acids. It comprises a N-terminal cell wall binding domain (CBD) and a C-terminal enzymatic active domain (EAD). The N-terminal CBD is a peptidoglycan binding domain (PGB, aa 7-96) having an amino acid sequence according to SEQ ID NO: 4. The C-terminal EAD is a catalytic domain (aa 126-292) complying with the catalytic domain of the lysozyme-like superfamily and having an amino acid sequence according to SEQ ID NO: 5. The PGB and the catalytic domain of the endolysin OBPgpLYS are connected by a domain linker.

Thus, preferred fragments of the polypeptide according to the present invention are polypeptides comprising an amino acid sequence according to SEQ ID NO: 4 and/or according to SEQ ID NO: 5. Another preferred fragment of the polypeptide according to the present invention comprises an amino acid sequence according to SEQ ID NO: 69. The fragment having an amino acid sequence according to SEQ ID NO: 69 differs from the polypeptide having an amino acid sequence according to SEQ ID NO: 1 in that the starting methionine residue has been deleted.

The derivatives according to the present invention are polypeptides comprising an amino acid sequence according to SEQ ID NO: 1, 4, 5 and/or 69 but having additional modification and/or alterations. Said modifications and/or alterations can be mutations in particular deletions, insertions, additions, substitutions or any combinations thereof and/or chemical changes of the amino acid residues, e.g. biotinylation, acetylation, pegylation, chemical changes of the amino-, SH- or carboxyl-groups. Said derivatives according to the present invention exhibit the lytic activity of the OBPgpLYS (SEQ ID NO: 1) and/or the activity of the fragments according to the present invention. Said activity can be about 10, 20, 30, 40, 50, 60, 70, 80, 90, 100, 110, 120, 130, 140, 150, 160, 170, 180, 190 or about 200% of the activity of the OBPgpLYS and/or the activity of the fragments according to the present invention. The activity can be measured by assays well known in the art by a person skilled in the art as e.g. the plate lysis assay or the liquid lysis assay which are e.g. described in (Briers et al., *J. Biochem. Biophys Methods* 70: 531-533, (2007)).

Preferred derivatives according to the present invention are polypeptides comprising an amino acid sequence according to SEQ ID NO: 86 and 87. Said derivatives differ from the polypeptides having an amino acid sequence according to SEQ ID NO: 1 and SEQ ID NO: 69, respectively, in that the leucine residue has been substituted by a histidine residue at positions 325 and 324, respectively. The polypeptide comprising an amino acid sequence according to SEQ ID NO: 86 is preferably encoded by a nucleotide sequence according to SEQ ID NO: 101.

In a preferred embodiment of the present invention the polypeptide, fragment and/or derivative according to the present invention comprises additionally a tag such as a $His_6$-tag, Strep-tag, Avi-tag, Myc-tag, Gst-tag, JS-tag, cystein-tag, FLAG-tag or other tags known in the art at the N-terminus or at the C-terminus. In a preferred embodiment of the present invention said tag is linked to the polypeptide, fragment and/or derivative according to the present invention at the C-terminus. Said tag may be linked to said polypeptide, fragment and/or derivative over additional amino acid residues. Said additional amino acid residues may be consist of at least 1, 2, 3, 4, 5, 6, 7, 8, 9 or 10 additional amino acid residues. In a preferred embodiment of the present invention the tag is linked to the polypeptide, fragment and/or derivative according to the present invention by the additional amino acid residues Leu-Glu or Lys-Gly.

In a preferred embodiment the present invention relates to polypeptides comprising an amino acid sequence according to SEQ ID NO: 47 or SEQ ID NO: 88. The polypeptide having an amino acid sequence according to SEQ ID NO: 47 and SEQ ID NO: 88, respectively, comprises in comparison to the polypeptide having an amino acid sequence according to SEQ ID NO: 1 and SEQ ID NO: 86, respectively, an additional C-terminal $His_6$-tag linked to the C-terminus of the polypeptide having an amino acid sequence according to SEQ ID NO: 1 and SEQ ID NO: 86, respectively, by the additional amino acid residues lysine and glycine (Lys-Gly). The polypeptide comprising an amino acid sequence according to SEQ ID NO: 47 is preferably encoded by a nucleotide sequence according to SEQ ID NO: 48. The polypeptide comprising an amino acid sequence according to SEQ ID NO: 88 is preferably encoded by a nucleotide sequence according to SEQ ID NO: 89.

A further aspect of the present invention are fusion proteins composed of an polypeptide, fragment and/or derivative according to the present invention and a peptide stretch fused to the polypeptide, fragment and/or derivative according to the present invention at the N- or C-terminus.

The peptide stretch of the fusion protein according to the present invention is preferably covalently bound to the polypeptide, fragment and/or derivative according to the present invention. Preferably, said peptide stretch consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100 amino acid residues. Especially preferred is a peptide stretch comprising about 5 to about 100 amino acid residues, about 5 to about 50 or about 5 to about 30 amino acid residues. More preferred is a peptide stretch comprising about 6 to about 42 amino acid residues, about 6 to about 39 amino acid residues, about 6 to about 38 amino acid residues, about 6 to about 31 amino acid residues, about 6 to about 25 amino acid residues, about 6 to about 24 amino acid residues, about 6 to about 22 amino acid residues, about 6 to about 21 amino acid residues, about 6 to about 20 amino acid residues, about 6 to about 19 amino acid residues, about 6 to about 16 amino acid residues, about 6 to about 14 amino acid residues, about 6 to about 12 amino acid residues, about 6 to about 10 amino acid residues or about 6 to about 9 amino acid residues. Preferably, the peptide stretch is no tag such as a $His_6$-tag, Strep-tag, Avi-tag, Myc-tag, Gst-tag, JS-tag, cystein-tag, FLAG-tag or other tags known in the art and no thioredoxin or maltose binding proteins (MBP). However, the peptide stretch may comprise in addition such tag or tags or the like, which are used to purify or locate proteins.

Figure 5B:
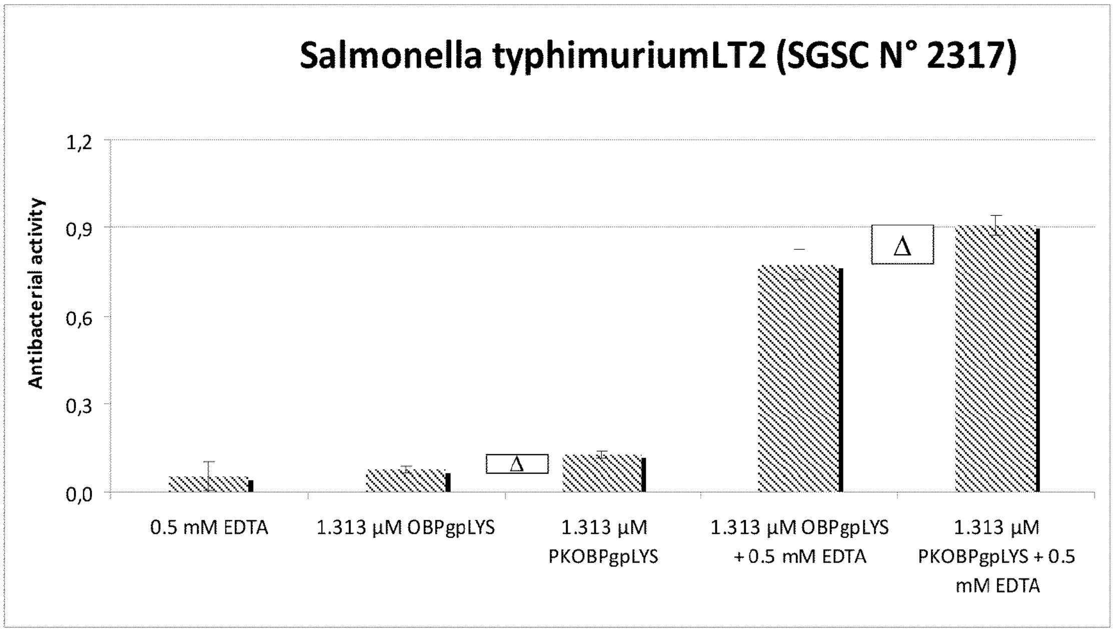
Figure 5C:
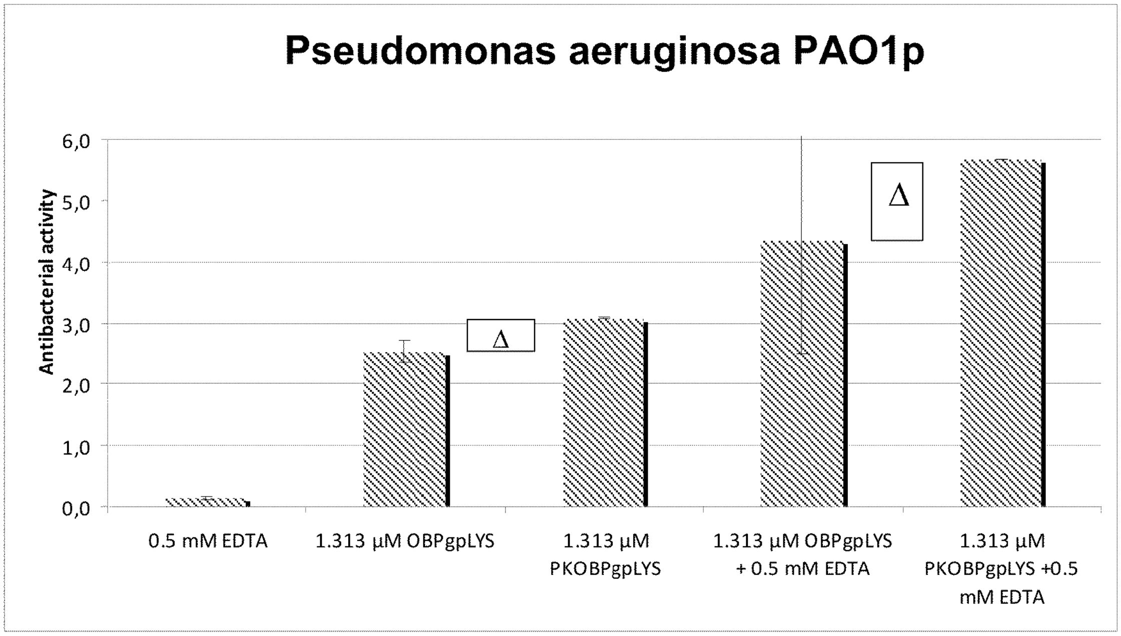
Figure 5D:
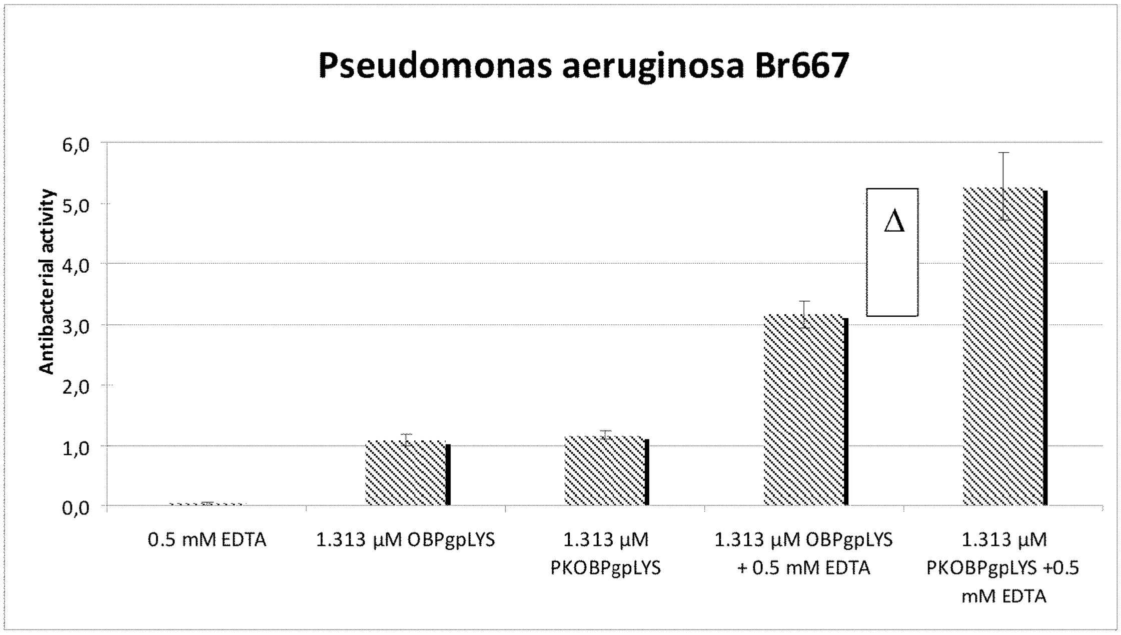
Figure 5E:
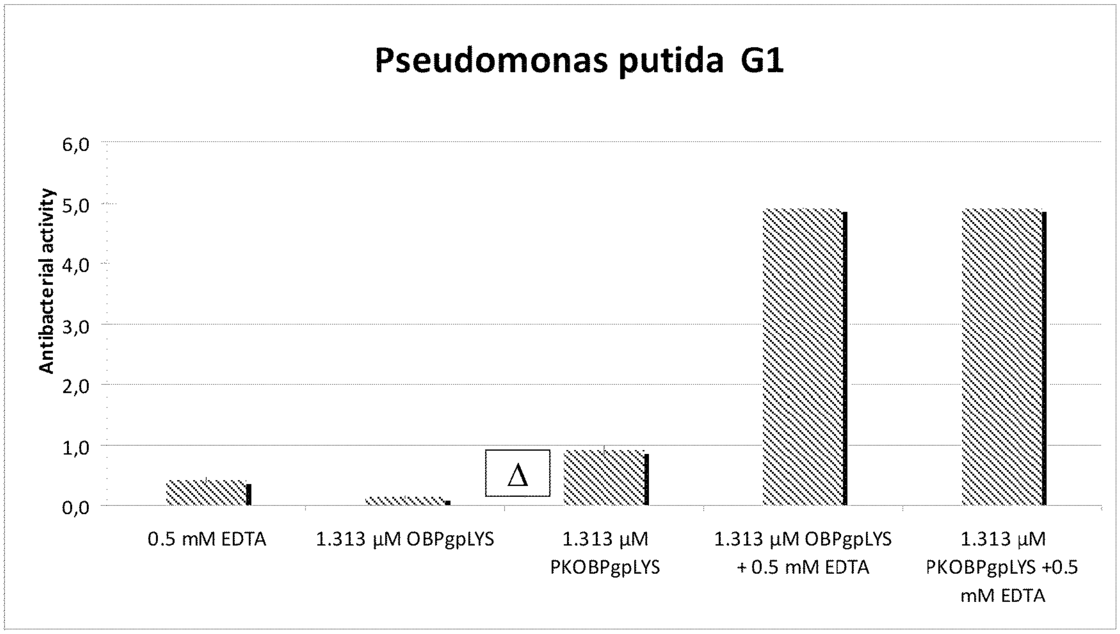
Figure 5F:
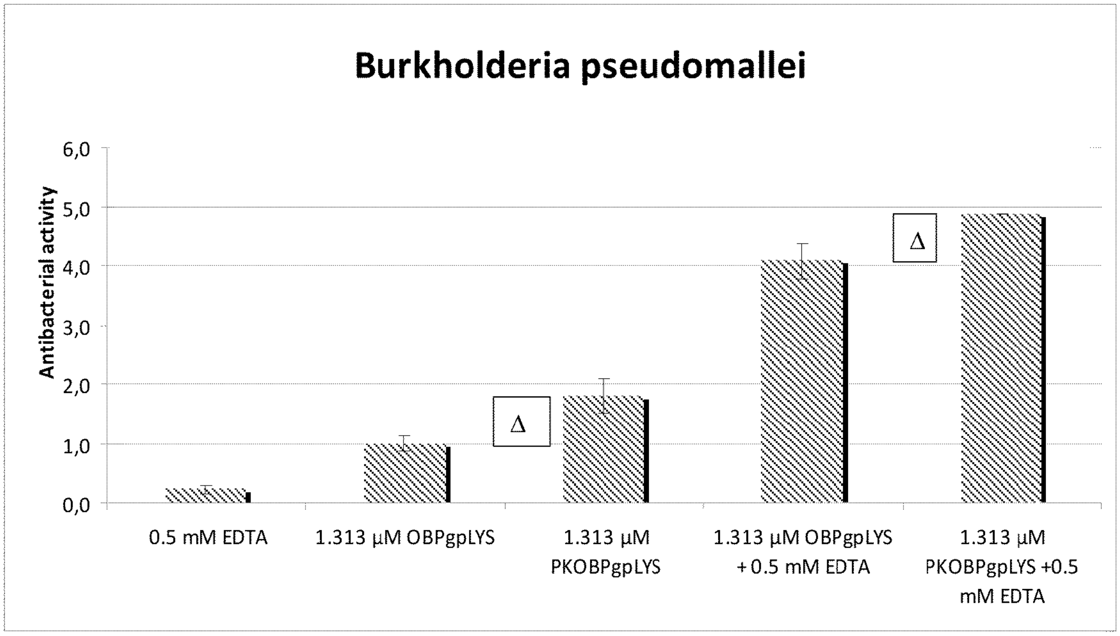
Figure 6:
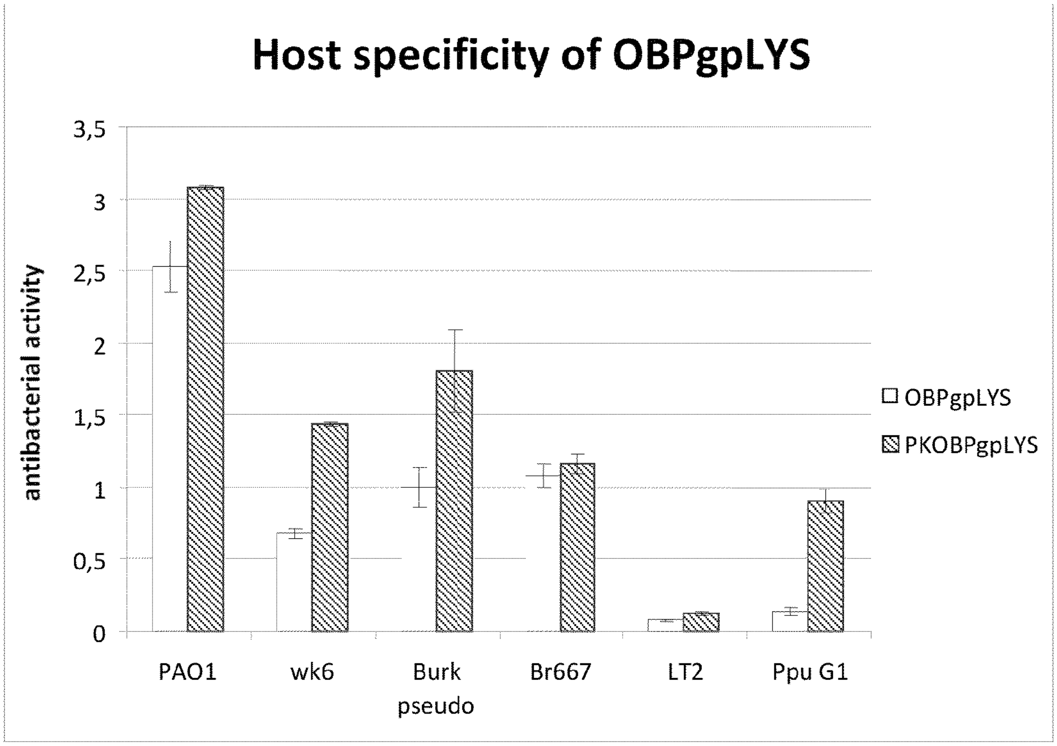
FIG. 6 shows in a graphic representation the host specificity of the unmodified OBPgpLYS (SEQ ID NO: 47) and the modified PKOBPgpLYS (SEQ ID NO: 49). Each species of Gram-negative bacteria was incubated for 30 minutes with a composition comprising each 1.315 μM unmodified OBPgpLYS or modified PKOBPgpLYS. The bar chart gives the antibacterial activities of the unmodified OBPgpLYS and modified OBPgpLYS on *Pseudomonas aeruginosa* PAO1p cells (PAO1), *Escherichia coli* WK6 cells (wk6), *Burkholderia pseudomallei* cells (Burk pseudo), *Pseudomonas aeruginosa* Br667 cells (Br667), *Salmonella typhimurium* LT2 cells (LT2) and *Pseudomonas putida* G1 cells (Ppu G1). The error bars indicate the standard deviations of the mean.

Preferably, the peptide stretch has the function to lead the fusion protein according to the present invention through the outer membrane of Gram-negative bacteria but has no or only low activity when administered without being fused to the polypeptide, fragment and/or derivative according to the present invention. The function to lead the fusion protein through the outer membrane of Gram-negative bacteria is caused by the potential of the membrane or LPS disrupting activity of said peptide stretch. To determine whether a peptide stretch has membrane or LPS disrupting activity said peptide stretch can be fused to a polypeptide according to the present invention as e.g. described in the Examples of the present invention. Subsequently, the antibacterial activity of the fusion protein consisting of the polypeptide according to the present invention and the peptide stretch to be tested can be compared to the polypeptide according the present invention having no peptide stretch as also described in the Examples of the present invention and e.g. shown in FIGS. 5A-5F and 6. Preferably, said tests may be carried out on *Escherichia coli* WK6 and/or *Pseudomonas aeruginosa* PAO1p cells as used in the Examples of the present invention. In case the fusion protein has an increased antibacterial activity in comparison to the polypeptide according to the present invention without said peptide stretch for at least one of the tested gram-negative bacteria species then said peptide stretch has a membrane or LPS disrupting activity. Preferably, the antibacterial activity (in logarithmic units ($=\log_{10}N_0/N_i$)) of the polypeptide according to the present invention is increased by at least about 5%, more preferably by at least about 10%, by a peptide stretch having membrane or LPS disrupting activity.

In one aspect of the present invention the fused peptide stretch is an amphipathic peptide, which comprises one or more of the positively charged amino acid residues of lysine, arginine and/or histidine, combined to one or more of the hydrophobic amino acid residues of valine, isoleucine, leucine, methionine, phenylalanine, tryptophan, cysteine, alanine, tyrosine, histidine, threonin, serine, proline and/or glycine. Side chains of the amino acid residues are preferably oriented in order that cationic and hydrophobic surfaces are clustered at opposite sides of the peptide. Preferably, more than about 30, 40, 50, 60 or 70% of the amino acids in said peptide are positively charged amino acids. Preferably, more than about 30, 40, 50, 60 or 70% of the amino acid residues in said peptide are hydrophobic amino acid residues. Advantageously, the amphipathic peptide is fused at the N-terminal and/or the C-terminal end of the polypeptide, fragment and/or derivative according to the present invention having cell wall degrading activity, thus enhancing the amphipathicity of the latter proteins.

In a preferred embodiment at least about 30, 40, 50, 60 or 70% of the said amino acid residues of the amphipathic peptide are either arginine or lysine residues and/or at least about 30, 40, 50, 60 or 70% of the said amino acid residues of the amphipathic peptide are of the hydrophobic amino acid residues valine, isoleucine, leucine, methionine, phenylalanine, tryptophan, cysteine, alanine, tyrosine, histidine, threonin, serine, proline and/or glycine.

Preferred amphipatic peptides are Pleurocidin according to SEQ ID NO: 6, Cecropin P1 according to SEQ ID NO: 7, Buforin II according to SEQ ID NO: 8, Buforin I according to SEQ ID NO: 9 and Magainin according to SEQ ID NO: 10. Further preferred amphipatic peptides are Cathelidicine e.g. LL-37 according to SEQ ID NO: 11.

In a further aspect of the present invention the fused peptide stretch is an antimicrobial peptide, which comprises a positive net charge and around 50% hydrophobic amino acid residues. The antimicrobial peptides are amphipathic, with a length of about 12 to about 50 amino acid residues.

Preferred antimicrobial peptides are listed in the following table.

| Peptide | Sequence | |
|---|---|---|
| LL-37 | LLGDFFRKSKEKIGKEFKRIVQRIKDFLRNLVPRTES | SEQ ID NO: 11 |
| SMAP-29 | RGLRRLGRKIAHGVKKYGPTVLRIIRIAG | SEQ ID NO: 12 |
| Indolicidin | ILPWKWPWWPWRR | SEQ ID NO: 13 |
| Protegrin | RGGRLCYCRRRFCVCVGR | SEQ ID NO: 14 |
| Cecropin P1 | SWLSKTAKKLENSAKKRISEGIAIAIQGGPR | SEQ ID NO: 7 |
| Magainin | GIGKFLHSAKKFGKAFVGEIMNS | SEQ ID NO: 10 |
| Pleurocidin | GWGSFFKKAAHVGKHVGKAALTHYL | SEQ ID NO: 6 |
| Cecropin A (*A. aegypti*) | GGLKKLGKKLEGAGKRVFNAAEKALPVVAGAKALRK | SEQ ID NO: 15 |

-continued

| Peptide | Sequence | |
|---|---|---|
| Cecropin A (*D. melanogaster*) | GWLKKIGKKIERVGQHTRDATIQGLGIPQQAANVAATARG | SEQ ID NO: 16 |
| Buforin II | TRSSRAGLQFPVGRVHRLLRK | SEQ ID NO: 8 |
| Sarcotoxin IA | GWLKKIGKKIERVGQHTRDATIQGLGIAQQAANVAATAR | SEQ ID NO: 17 |
| Ascaphine | GIKDWIKGAAKKLIKTVASHIANQ | SEQ ID NO: 50 |
| Apidaecine | ANRPVYIPPPRPPHPRL | SEQ ID NO: 51 |
| Nigrocine | GLLSKVLGVGKKVLCGVSGLVC | SEQ ID NO: 52 |
| Pseudin 1 | GLNTLKKVFQGLHEAIKLINNHVQ | SEQ ID NO: 53 |
| Parasin 1 | KGRGKQGGKVRAKAKTRSS | SEQ ID NO: 72 |
| Lycotoxin | IWLTALKFLGKHAAKKLAKQQLSKL | SEQ ID NO: 73 |
| Ranalexin | FLGGLIVPAMICAVTKKC | SEQ ID NO: 117 |
| Melittin | GIGAVLKVLT TGLPALISWI KRKRQQ | SEQ ID NO: 119 |

In a further aspect of the present invention the fused peptide stretch is a sushi peptide which is described by Ding J L, Li P, Ho B Cell Mol Life Sci. 2008 April; 65(7-8):1202-19. The Sushi peptides: structural characterization and mode of action against Gram-negative bacteria.

Preferred sushi peptides are sushi peptides S1 and S3 and multiples thereof; FASEB J. 2000 September; 14(12): 1801-13.

In a further aspect of the present invention the fused peptide stretch is a defensin, preferably Cathelicidine, Cecropin P1, Cecropin A or Magainin II.

In a further aspect of the present invention the fused peptide stretch is a hydrophobic peptide, preferably having the amino acid sequence Phe-Phe-Val-Ala-Pro (SEQ ID NO:18).

Further preferred peptide stretches are listed in the following table:

| | | |
|---|---|---|
| Alpha 4 | PNRAKRVITTFRT | SEQ ID NO: 68 |
| Artilysin1 | GFFIPAVILPSIAFLIVP | SEQ ID NO: 70 |
| Artilysin2 | GKPGWLIKKALVFKKLIR RPLKRLA | SEQ ID NO: 71 |
| WLBU2 variant | KRWVKRVKRVKRWVKRVV RVVKRWVKR | SEQ ID NO: 118 |

In one aspect of the present invention the fused peptide stretch is an cationic and/or polycationic peptide, which comprises one or more of the positively charged amino acid residues of lysine, arginine and/or histidine, in particular of lysine and/or arginine. Preferably, more than about 20, 30, 40, 50, 60, 70, 75, 80, 85, 90, 95 or 99% of the amino acid residues in said peptide stretch are positively charged amino acid residues, in particular lysine and/or arginine residues. Especially preferred are peptide stretches consisting of about 100% positively charged amino acid residues, in particular arginine and/or lysine residues, wherein preferably about 60% to about 70% of said positively charged amino acid residues are lysine residues and about 30% to about 40% of said positively charged amino acid residues are arginine residues. More preferred is a peptide stretch consisting of about 100% positively charged amino acid residues, in particular arginine and/or lysine residues, wherein preferably about 64% to about 68% of said positively charged amino acid residues are lysine and about 32% to about 36% of said positively charged amino acid residues are arginine. Peptide stretches consisting of either only arginine or only lysine are also preferred.

Especially preferred are cationic and/or polycationic peptide stretches comprising at least one motif according to SEQ ID NO: 19 (KRKKRK). In particular cationic peptide stretches comprising at least 2, 3, 4, 5, 6, 7, 8, 9, 10, 11, 12, 13, 14, 15, 16 or 17 motifs according to SEQ ID NO: 19 (KRKKRK) are preferred. More preferred are cationic peptide stretches comprising at least one KRK motif (lys-arg-lys), preferable at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 KRK motifs.

In another preferred embodiment of the present invention the cationic peptide stretch comprises beside the positively charged amino acid residues, in particular lysine and/or arginine residues, neutrally charged amino acid residues, in particular glycine and/or serine residues. Preferred are cationic peptide stretches consisting of about 70% to about 100%, or about 80% to about 95%, or about 85% to about 90% positively charged amino acid residues, in particular lysine and/or arginine residues and of about 0% to about 30%, or about 5% to about 20%, or about 10% to about 20% neutrally charged amino acid residues, in particular glycine and/or serine residues. Preferred are polypeptide stretches consisting of about 4% to about 8% serine residues, of about 33% to about 36% arginine residues and of about 56% to about 63% lysine residues. Especially preferred are polypeptide stretches comprising at least one motif according to SEQ ID NO: 40 (KRXKR), wherein X is any other amino acid residue than lysine, arginine and histidine. Especially preferred are polypeptide stretches comprising at least one motif according to SEQ ID NO: 41 (KRSKR). More preferred are cationic stretches comprising at least about 2, 3, 4, 5, 6, 7, 8, 9, 10, 11, 12, 13, 14, 15, 16, 17, 18, 19 or about 20 motifs according to SEQ ID NO: 40 (KRXKR) or SEQ ID NO: 41 (KRSKR).

Also preferred are polypeptide stretches consisting of about 9 to about 16% glycine residues, of about 4 to about 11% serine residues, of about 26 to about 32% arginine residues and of about 47 to about 55% lysine residues. Especially preferred are polypeptide stretches comprising at least one motif according to SEQ ID NO: 42 (KRGSG). More preferred are cationic stretches comprising at least about 2, 3, 4, 5, 6, 7, 8, 9, 10, 11, 12, 13, 14, 15, 16, 17, 18, 19 or about 20 motifs according to SEQ ID NO: 42 (KRGSG).

In another preferred embodiment of the present invention the cationic peptide stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, histidine, threonin, serine, proline and/or glycine residues. Preferred are cationic peptide stretches consisting of about 70% to about 100%, or about 80% to about 95%, or about 85% to about 90% positively charged amino acid residues, in particular lysine and/or arginine residues and of about 0% to about 30%, or about 5% to about 20%, or about 10% to about 20% hydrophobic amino acid residues in particular valine, isoleucine, leucine, methionine, phenylalanine, tryptophan, cysteine, alanine, tyrosine, histidine, threonin, serine, proline and/or glycine residues.

Especially preferred are peptide stretches selected from the group consisting of the following sequences:

| Peptide stretch | length | SEQ ID NO: |
|---|---|---|
| KRKKRK | 6 | SEQ ID NO: 19 |
| KRKKRKKRK | 9 | SEQ ID NO: 20 |
| RRRRRRRRR | 9 | SEQ ID NO: 21 |
| KKKKKKKK | 8 | SEQ ID NO: 22 |
| KRKKRKKRKK | 10 | SEQ ID NO: 23 |
| KRKKRKKRKKRK | 12 | SEQ ID NO: 24 |
| KRKKRKKRKKRKKR | 14 | SEQ ID NO: 25 |
| KKKKKKKKKKKKKKKK | 16 | SEQ ID NO: 26 |
| KRKKRKKRKKRKKRKKRKK | 19 | SEQ ID NO: 27 |
| RRRRRRRRRRRRRRRRRRR | 19 | SEQ ID NO: 28 |
| KKKKKKKKKKKKKKKKKKK | 19 | SEQ ID NO: 29 |
| KRKKRKKRKRSKRKKRKKRK | 20 | SEQ ID NO: 30 |
| KRKKRKKRKRSKRKKRKKRKK | 21 | SEQ ID NO: 31 |
| KRKKRKKRKKRKKRKKRKKRK | 21 | SEQ ID NO: 32 |
| KRKKRKKRKRGSGKRKKRKKRK | 22 | SEQ ID NO: 33 |
| KRKKRKKRKRGSGSGKRKKRKKRK | 24 | SEQ ID NO: 34 |
| KRKKRKKRKKRKKRKKRKKRKKRKK | 25 | SEQ ID NO: 35 |
| KRKKRKKRKRSKRKKRKKRKRSKRKKRKKRK | 31 | SEQ ID NO: 36 |
| KRKKRKKRKRGSGSGKRKKRKKRKGSGSGKRKKRKKRK | 38 | SEQ ID NO: 37 |
| KRKKRKKRKKRKKRKKRKKRKKRKKRKKRKKRKKRKKRK | 39 | SEQ ID NO: 38 |
| KRKKRKKRKRSKRKKRKKRKRSKRKKRKKRKRSKRKKRKKRK | 42 | SEQ ID NO: 39 |

Especially preferred is a fusion protein comprising a polypeptide, fragment and/or derivative according to the present invention and a peptide stretch having an amino acid sequence according to SEQ ID NO: 20. More preferred are fusion proteins having an amino acid sequence according to SEQ ID NO: 43 and SEQ ID NO: 115. Also preferred are fusion proteins an amino acid sequence according to SEQ ID NO: 49 and SEQ ID NO: 116. The fusion proteins having an amino acid sequence according to SEQ ID NO: 49 and SEQ ID NO: 116, respectively, comprises in comparison to the fusion proteins having an amino acid sequence according to SEQ ID NO: 43 and SEQ ID NO: 115, respectively, an additional C-terminal $His_6$-tag linked to the C-terminus of the fusion protein having an amino acid sequence according to SEQ ID NO: 43 and SEQ ID NO: 115, respectively, by the additional amino acid residues lysine and glycine (Lys-Gly). The fusion proteins having an amino acid sequence according to SEQ ID NO: 43 and SEQ ID NO: 115 and SEQ ID NO: 49 and SEQ ID NO: 116, respectively, differ in that the fusion proteins having an amino acid sequence according to SEQ ID NO: 115 and SEQ ID NO: 116 has each a substitution of the leucine residue to a histidine residue at position 336.

In another preferred embodiment of the present invention the peptide stretches of the fusion protein according to the present invention comprise modifications and/or alterations of the amino acid sequences. Such alterations and/or modifications may comprise mutations such as deletions, insertions and additions, substitutions or combinations thereof and/or chemical changes of the amino acid residues, e.g. biotinylation, acetylation, peglyation, chemical changes of the amino-, SH- or carboxyl-groups.

A fusion protein according to the present invention as already outlined above is composed of (a) an polypeptide, fragment and/or derivative according to the present invention, and (b) a peptide stretch fused to said polypeptide, fragment and/or derivative at the N- or C-Terminus, and optionally (c) a tag, such as a $His_6$-tags, Strep-tags, Avi-tags, Myc-tags, Gst-tags, JS-tags, cystein-tags, FLAG-tags or other tags known in the art at the N- or C-Terminus.

In case the peptide stretch is fused to the polypeptide, fragment and/or derivative according to the present invention at the C-Terminus, the fusion protein comprises the additional tag preferably at the N-terminus. In an especially preferred embodiment of the present invention the peptide stretch is fused to the polypeptide, fragment and/or derivative according to the present invention at the N-Terminus. In case said fusion protein comprises an additional tag said tag is preferably at the C-terminus.

The two and three components of the fusion protein, respectively, as outlined above may be linked to each other over additional amino acid residues e.g. due to cloning reasons. Moreover, the peptide stretch may be linked to the starting methionine residue of the fusion protein by additional amino acid residues. Said additional amino acid residues may be consist of at least 1, 2, 3, 4, 5, 6, 7, 8, 9 or 10 additional amino acid residues. In a preferred embodiment of the present invention the peptide stretch is linked to the polypeptide, fragment and/or derivative according to the present invention by the additional amino acid residues Gly-Ser or Gly-Gly-Ser. The additional amino acid residues linking the starting methionine residue and the peptide stretch are preferably Gly-Ser. In case the fusion protein additionally comprises a tag, the polypeptide, fragment and/or derivative according to the present invention is preferably linked to said tag by the additional amino acid residues Leu-Glu or Lys-Gly.

The following table exemplifies the above outlined assembly of specifically preferred fusion proteins according to the present invention listed in the first column starting with the starting methionine residue at the N-terminus in the second column and ending with the optional tag at the C-terminus in the last column:

| Fusion protein according to the present invention (SEQ ID NO:) | First amino acid residue (N-term) | additional amino acid residues | peptide stretch (SEQ ID NO:) | additional amino acid residues | polypeptide, fragment, derivative according to the present invention (SEQ ID NO:) | additional amino acid residues | tag (C-term) |
|---|---|---|---|---|---|---|---|
| SEQ: 43 | Met | — | SEQ: 20 | Gly-Ser | SEQ: 69 | — | — |
| SEQ: 49 | Met | — | SEQ: 20 | Gly-Ser | SEQ: 69 | Lys-Gly | $HIS_6$-tag |
| SEQ: 54 | Met | — | SEQ: 50 | Gly-Ser | SEQ: 87 | — | — |
| SEQ: 55 | Met | — | SEQ: 50 | Gly-Ser | SEQ: 87 | Leu-Glu | $HIS_6$-tag |
| SEQ: 56 | Met | — | SEQ: 51 | Gly-Ser | SEQ: 87 | — | — |
| SEQ: 57 | Met | — | SEQ: 51 | Gly-Ser | SEQ: 87 | Leu-Glu | $HIS_6$-tag |
| SEQ: 58 | Met | — | SEQ: 52 | Gly-Ser | SEQ: 87 | — | — |
| SEQ: 59 | Met | — | SEQ: 52 | Gly-Ser | SEQ: 87 | Leu-Glu | $HIS_6$-tag |
| SEQ: 60 | Met | — | SEQ: 53 | Gly-Ser | SEQ: 87 | — | — |
| SEQ: 61 | Met | — | SEQ: 53 | Gly-Ser | SEQ: 87 | Leu-Glu | $HIS_6$-tag |
| SEQ: 62 | Met | — | SEQ: 17 | Gly-Ser | SEQ: 87 | — | — |
| SEQ: 63 | Met | — | SEQ: 17 | Gly-Ser | SEQ: 87 | Leu-Glu | $HIS_6$-tag |
| SEQ: 64 | Met | — | SEQ: 12 | Gly-Ser | SEQ: 87 | — | — |
| SEQ: 65 | Met | — | SEQ: 12 | Gly-Ser | SEQ: 87 | Leu-Glu | $HIS_6$-tag |
| SEQ: 66 | Met | — | SEQ: 15 | Gly-Ser | SEQ: 87 | — | — |
| SEQ: 67 | Met | — | SEQ: 15 | Gly-Ser | SEQ: 87 | Leu-Glu | $HIS_6$-tag |
| SEQ: 74 | Met | Gly-Ser | SEQ: 68 | Gly-Ser-Ser | SEQ: 87 | — | — |
| SEQ: 75 | Met | Gly-Ser | SEQ: 68 | Gly-Ser-Ser | SEQ: 87 | Lys-Gly | $HIS_6$-tag |
| SEQ: 76 | Met | Gly-Ser | SEQ: 69 | Gly-Ser-Ser | SEQ: 87 | — | — |
| SEQ: 77 | Met | Gly-Ser | SEQ: 69 | Gly-Ser-Ser | SEQ: 87 | Lys-Gly | $HIS_6$-tag |
| SEQ: 78 | Met | Gly-Ser | SEQ: 70 | Gly-Ser-Ser | SEQ: 87 | — | — |
| SEQ: 79 | Met | Gly-Ser | SEQ: 70 | Gly-Ser-Ser | SEQ: 87 | Lys-Gly | $HIS_6$-tag |
| SEQ: 80 | Met | Gly-Ser | SEQ: 71 | Gly-Ser-Ser | SEQ: 87 | — | — |
| SEQ: 81 | Met | Gly-Ser | SEQ: 71 | Gly-Ser-Ser | SEQ: 87 | Lys-Gly | $HIS_6$-tag |
| SEQ: 82 | Met | Gly-Ser | SEQ: 72 | Gly-Ser-Ser | SEQ: 87 | — | — |
| SEQ: 83 | Met | Gly-Ser | SEQ: 72 | Gly-Ser-Ser | SEQ: 87 | Lys-Gly | $HIS_6$-tag |
| SEQ: 84 | Met | Gly-Ser | SEQ: 73 | Gly-Ser-Ser | SEQ: 87 | — | — |
| SEQ: 85 | Met | Gly-Ser | SEQ: 73 | Gly-Ser-Ser | SEQ: 87 | Lys-Gly | $HIS_6$-tag |
| SEQ: 115 | Met | — | SEQ: 20 | Gly-Ser | SEQ: 87 | — | — |
| SEQ: 116 | Met | — | SEQ: 20 | Gly-Ser | SEQ: 87 | Lys-Gly | $HIS_6$-tag |

The present invention further relates to an isolated nucleic acid molecule encoding the polypeptide, fragment, derivative and/or fusion protein according to the present invention. Especially preferred isolated nucleic acid molecules according to the present invention comprise a nucleic acid sequence according to SEQ ID NO: 2, 3, 48, 89 or 101. The present invention further relates to a vector comprising the nucleic acid molecule according to the present invention. Said vector may provide for the constitutive or inducible expression of said polypeptide, fragment, derivative and/or fusion protein according to the present invention.

The invention also relates to a method for obtaining said polypeptide, fragment, derivative and/or fusion proteins from a micro-organism, such as a genetically modified suitable host cell which expresses said polypeptide, fragment, derivative and/or fusion proteins. Said host cell may be a microorganism such as bacteria or yeast or an animal cell as e.g. a mammalian cell, in particular a human cell. In one embodiment of the present invention the host cell is an *Escherichia coli* cell. The host may be selected due to mere biotechnological reasons, e.g. yield, solubility, costs, etc. but may be also selected from a medical point of view, e.g. a non-pathological bacteria or yeast or human cells. Another aspect of the present invention is related to a method for genetically transforming a suitable host cell in order to obtain the expression of the polypeptide, fragment, derivative and/or fusion proteins according to the present invention, wherein the host cell is genetically modified by the introduction of a genetic material encoding said polypeptide, fragment, derivative and/or fusion proteins into the host cell and obtain their translation and expression by genetic engineering methods well known by the man skilled in the art.

In a further aspect the present invention relates to a composition, preferably a pharmaceutical composition, comprising a polypeptide, fragment, derivative and/or fusion protein according to the present invention and/or a host transformed with a nucleic acid molecule or a vector comprising a nucleotide sequence encoding a polypeptide, fragment, derivative and/or fusion protein according to the present invention.

In a preferred embodiment of the present invention the composition comprises additionally agents permeabilizing the outer membrane of Gram-negative bacteria such metal chelators as e.g. EDTA, TRIS, lactic acid, lactoferrin, polymyxin, citric acid and/or other substances as described e.g. by Vaara (Agents that increase the permeability of the outer membrane. Vaara M. Microbiol Rev. 1992 September; 56(3): 395-441). Also preferred are compositions comprising combinations of the above mentioned permeabilizing agents. Especially preferred is a composition comprising about 10 μM to about 100 mM EDTA, more preferably about 50 μM to about 10 mM EDTA, more preferably about 0.5 mM to about 10 mM EDTA, more preferably about 0.5 mM to about 2 mM EDTA, more preferably about 0.5 mM to about 1 mM EDTA. Also preferred is a composition comprising about 0.5 mM to about 2 mM EDTA, more preferably about 1 mM EDTA and additionally about 10 to about 100 mM TRIS.

The present invention also relates to a polypeptide, fragment, derivative and/or fusion protein according to the present invention and/or a host transformed with a nucleic acid comprising a nucleotide sequence encoding a polypeptide, fragment, derivative and/or fusion protein according to the present invention for use as a medicament. In a further aspect the present invention relates to the use of a polypeptide, fragment, derivative and/or fusion protein according to the present invention and/or a host transformed with a vector comprising a nucleic acid molecule comprising a nucleotide sequence encoding a polypeptide, fragment, derivative and/or fusion protein according to the present invention in the manufacture of a medicament for the treatment and/or prevention of a disorder, disease or condition associated with Gram-negative bacteria. In particular the treatment and/or prevention of the disorder, disease or condition may be caused by Gram-negative bacteria of bacterial groups, families, genera or species comprising strains pathogenic for humans or animals like Enterobacteriaceae (*Escherichia*, especially *E. coli, Salmonella, Shigella, Citrobacter, Edwardsiella, Enterobacter, Hafnia, Klebsiella*, especially *K. pneumoniae, Morganella, Proteus, Providencia, Serratia, Yersinia*), Pseudomonadaceae (*Pseudomonas*, especially *P. aeruginosa, Burkholderia, Stenotrophomonas, Shewanella, Sphingomonas, Comamonas*), *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella*, Spirochaetaceae (*Treponema* and *Borrelia*), Leptospiraceae, *Campylobacter, Helicobacter, Spirillum, Streptobacillus*, Bacteroidaceae (*Bacteroides, Fusobacterium, Prevotella, Porphyromonas*), *Acinetobacter*, especially *A. baumanii*. In particular, the treatment and/or prevention of the disorder, disease or condition may be caused by *Pseudomonas aeruginosa, Pseudomonas putida, Burkholderia pseudomallei, E. coli* and/or *Salmonella typhimurium*.

The present invention further relates to a medicament comprising a polypeptide, fragment, derivative and/or fusion protein according to the present invention and/or a host transformed with a nucleic acid comprising a nucleotide sequence encoding a polypeptide, fragment, derivative and/or fusion protein according to the present invention.

In a further aspect the present invention relates to a method of treating a disorder, disease or condition in a subject in need of treatment and/or prevention, which method comprises administering to said subject an effective amount of a polypeptide, fragment, derivative and/or fusion protein according to the present invention and/or an effective amount of a host transformed with a nucleic acid comprising a nucleotide sequence encoding a polypeptide, fragment, derivative and/or fusion protein according to the present invention or a composition according to the present invention. The subject may be a human or an animal.

In particular said method of treatment may be for the treatment and/or prevention of infections of the skin, of soft tissues, the respiratory system, the lung, the digestive tract, the eye, the ear, the teeth, the nasopharynx, the mouth, the bones, the vagina, of wounds of bacteraemia and/or endocarditis caused by Gram-negative bacteria, in particular by the Gram-negative bacteria as listed above.

The dosage and route of administration used in a method of treatment (or prophylaxis) according to the present invention depends on the specific disease/site of infection to be treated. The route of administration may be for example oral, topical, nasopharyngeal, parenteral, intravenous, rectal or any other route of administration.

For application of a polypeptide, fragment, derivative and/or fusion protein according to the present invention and/or an effective amount of a host transformed with a nucleic acid comprising a nucleotide sequence encoding a polypeptide, fragment, derivative and/or fusion protein according to the present invention or a composition according to the present invention to a site of infection (or site endangered to be infected) a formulation may be used that protects the active compounds from environmental influences such as proteases, oxidation, immune response etc., until it reaches the site of infection. Therefore, the formulation may be capsule, dragee, pill, suppository, injectable solution or any other medical reasonable galenic formulation. Preferably, the galenic formulation may comprise suitable carriers, stabilizers, flavourings, buffers or other suitable reagents. For example, for topical application the formulation may be a lotion or plaster, for nasopharyngeal application the formulation may be saline solution to be applied via a spray to the nose.

Preferably, a polypeptide, fragment, derivative and/or fusion protein according to the present invention is used for medical treatment, if the infection to be treated (or prevented) is caused by multiresistant bacterial strains, in particular by strains resistant against one or more of the following antibiotics: streptomycin, tetracycline, cephalothin, gentamicin, cefotaxime, cephalosporin, ceftazidime or imipenem. Furthermore, a polypeptide, fragment, derivative and/or fusion protein according to the present invention can be used in methods of treatment by administering it in combination with conventional antibacterial agents, such as antibiotics, lantibiotics, bacteriocins or endolysins, etc.

The present invention also relates to a pharmaceutical pack comprising one or more compartments, wherein at least one compartment comprises one or more polypeptide, fragment, derivative and/or fusion protein according to the present invention and/or one or more hosts transformed with a nucleic acid comprising a nucleotide sequence encoding a polypeptide, fragment, derivative and/or fusion protein according to the present invention or a composition according to the present invention.

In another aspect the present invention relates to a process of preparation of a pharmaceutical composition, said process comprising admixing one or more polypeptide, fragment, derivative and/or fusion protein according to the present invention and/or one or more hosts transformed with a nucleic acid comprising a nucleotide sequence encoding a polypeptide, fragment, derivative and/or fusion protein according to the present invention with a pharmaceutically acceptable diluent, excipient or carrier.

In an even further aspect the composition according to the present invention is a cosmetic composition. Several bacterial species can cause irritations on environmentally exposed surfaces of the patient's body such as the skin. In order to prevent such irritations or in order to eliminate minor manifestations of said bacterial pathogens, special cosmetic preparations may be employed, which comprise sufficient amounts of the polypeptide, fragment, derivative and/or fusion protein according to the present invention in order to degrade already existing or freshly settling pathogenic Gram-negative bacteria.

In a further aspect the present invention relates to the polypeptide, fragment, derivative and/or fusion protein according to the present invention for use as diagnostic means in medicinal, food or feed or environmental diagnostics, in particular as a diagnostic means for the diagnostic of bacteria infection caused in particular by Gram-negative bacteria. In this respect the polypeptide, fragment, derivative and/or fusion protein according to the present invention may be used as a tool to specifically degrade pathogenic bacteria, in particular Gram-negative pathogenic bacteria. The degradation of the bacterial cells by the polypeptide, fragment, derivative and/or fusion protein according to the present invention can be supported by the addition of detergents like Triton X-100 or other additives which weaken the bacterial cell envelope like polymyxin B. Specific cell degradation is needed as an initial step for subsequent specific detection of bacteria using nucleic acid based methods like PCR, nucleic acid hybridization or NASBA (Nucleic Acid Sequence Based Amplification), immunological methods like IMS, immunofluorescence or ELISA techniques, or other methods relying on the cellular content of the bacterial cells like enzymatic assays using proteins specific for distinct bacterial groups or species (e.g. β-galactosidase for enterobacteria, coagulase for coagulase positive strains).

In a further aspect the present invention relates to the use of the polypeptide, fragment, derivative and/or fusion protein according to the present invention for the treatment or prevention of Gram-negative bacterial contamination of foodstuff, of food processing equipment, of food processing plants, of surfaces coming into contact with foodstuff such as shelves and food deposit areas and in all other situations, where pathogenic, facultative pathogenic or other undesirable bacteria can potentially infest food material, of medical devices and of all kind of surfaces in hospitals and surgeries.

In particular, a polypeptide, fragment, derivative and/or fusion protein of the present invention may be used prophylactically as sanitizing agent. Said sanitizing agent may be used before or after surgery, or for example during hemodialysis. Moreover, premature infants and immunocompromised persons, or those subjects with need for prosthetic devices may be treated with a fusion protein according to the present invention. Said treatment may be either prophylactically or during acute infection. In the same context, nosocomial infections, especially by antibiotic resistant strains like *Pseudomonas aeruginosa* (FQRP), *Acinetobacter* species and Enterobacteriaceae such as *E. coli, Salmonella, Shigella, Citrobacter, Edwardsiella, Enterobacter, Hafnia, Klebsiella, Morganella, Proteus, Providencia, Serratia* and *Yersinia* species may be treated prophylactically or during acute phase with a polypeptide, fragment, derivative and/or fusion protein of the present invention. Therefore, a polypeptide, fragment, derivative and/or fusion protein according to the present invention may be used as a disinfectant also in combination with other ingredients useful in a disinfecting solution like detergents, tensids, solvents, antibiotics, lantibiotics, or bacteriocins.

The following examples explain the present invention but are not considered to be limiting. Unless indicated differently, molecular biological standard methods were used, as e.g., described by Sambrock et al., 1989, Molecular Cloning: A Laboratory Manual, 2nd edition, Cold Spring Harbor Laboratory Press, Cold Spring Harbor, N.Y.

EXAMPLE 1

Modified Endolysin Variants of *Pseudomonas putida* Phage OBP

OBPgpLYS having an amino acid sequence according to SEQ ID NO: 1 is a modular endolysin of 332 amino acid residues originating from *Pseudomonas putida* phage OBP with a putative N-terminal peptidoglycan binding domain and a C-terminal catalytic chitinase domain. OPBgpLYS having an amino acid sequence according to SEQ ID NO: 47 comprises in comparison to OBPgpLYS having an amino acid sequence according to SEQ ID NO: 1 an additional C-terminal $His_6$-tag linked to the C-terminus by the additional amino acid residues lysin and glycin (Lys-Gly)

Purified genomic DNA of phage OBP was used as a template for the amplification of the open reading frame (ORF) of OBPgpLYS in standard PCR reaction with Pfu polymerase (Fermentas, Ontario, Canada) using the following PCR parameters:

95° C. 2′ ←
95° C. 30″ ↑
56° C. 30″ | 35 cycles
72° C. 2′30″ →
72° C. 10′
4° C. ∞

Therefore a standard 5' primer (5' ATGAAAAATAGC-GAGAAGAAT 3' (SEQ ID NO: 44)) and a standard 3' primer (5' AACTATTCCGAGTGCTTTCTTTGT 3' (SEQ ID NO: 45)) was used. To extend the 5' end of the ORF which encodes OBPgpLYS with a gene fragment encoding the polycationic 9-mer peptide Lys-Arg-Lys-Lys-Arg-Lys-Lys-Arg-Lys-(SEQ ID NO: 20) a tail PCR (with same parameters as standard PCR above) with an extended 5' primer (5' ATGGGATC-CAAACGCAAGAAACGTAAGAAACG-CAAAAAAAATAGCGAG AAGAAT 3' (SEQ ID NO: 46)) and the standard 3' primer according to SEQ ID NO: 45 was applied. Both the original unmodified OBPgpLYS PCR fragment and the extended fragment were ligated in the pEXP5CT/TOPO® expression vector (Invitrogen, Carlsbad, Calif., USA) by following the TA-cloning protocol of the manufacturer.

Recombinant expression of OBPgpLYS having an amino acid sequence according to SEQ ID NO: 47 and PKOBPgpLYS having an amino acid sequence according to SEQ ID NO: 49 is performed in exponentially growing *E. coli* BL21 (XDE3) pLysS cells (Invitrogen) after induction with 1 mM IPTG (isopropylthiogalactoside) at 37° C. for a period of 4 hours. Both proteins were purified by $Ni^{2+}$ affinity chromatography (Akta FPLC, GE Healthcare) using the C-terminal 6× His-tag, encoded by the pEXP5CT/TOPO® expression vector. The $Ni^{2+}$ affinity chromatography is performed in 4 subsequent steps, all on room temperature:

1. Equilibration of the Histrap HP 1 ml column (GE Healthcare) with 10 column volumes of Washing Buffer (60 mM imidazole, 0.5 mM NaCl and 20 mM $NaH_2P0_4$-NaOH on pH 7.4) at a flow rate of 0.5 ml/min.
2. Loading of the total lysate (with wanted endolysin) on the Histrap HP 1 ml column at a flow rate of 0.5 ml/min.
3. Washing of the column with 15 column volumes of Washing Buffer at a flow rate of 1 ml/min.
4. Elution of bounded endolysin from the column with 10 column volumes of Elution Buffer (500 mM imidazole, 0.5 M NaCl and 20 mM $NaH_2P0_4$-NaOH on pH 7.4) at a flow rate of 0.5 ml/min The total yields of both purified recombinant proteins per liter *E. coli* expression culture is shown in Table 1. The values were determined by spectrophotometric measurement of the protein concentration and the total volume of the purified stock solution at a wavelength of 280 nm. Purified stock solutions consisting of OBPgpLYS and PKOBPgpLYS, respectively, in Elution Buffer (20 mM $NaH_2P0_4$-NaOH pH7.4; 0.5 M NaCl; 500 mM imidazole) were at least 90% pure as determined visually on SDS-PAGE gels.

TABLE 1

Yields of purified recombinant OBPgpLYS endolysin and its PK-modified PKOBPgpLYS per liter *E. coli* expression culture.

| Endolysins | Expression yield |
|---|---|
| OBPgpLYS (SEQ ID NO: 47) | 3.3 mg |
| PKOBPgpLYS (SEQ ID NO: 49) | 4.7 mg |

To determine the anti-Gram-negative spectrum of the endolysins OBPgpLYS according to SEQ ID NO: 47 and PKOBPgpLYS according to SEQ ID NO: 49, a combination of 1.313 μM of each endolysin and 0.5 mM EDTA was tested on the clinical multiresistant *P. aeruginosa* strain Br667, *Pseudomonas putida* G1 (host of phage OBP) and a range of other Gram-negative pathogens (*P. aeruginosa* PAO1p, *P. aeruginosa* Br667, *P. putida* G1, *Burkholderia pseudomallei, Escherichia coli* WK6 and *Salmonella typhimurium*) (see Table 3). Exponential growing bacterial cells ($OD_{600\ nm}$ of 0.6) were 100-fold diluted to a final density of about $10^6$ cells/ml of each strain was incubated for 30 minutes at room temperature without shaking with unmodified endolysin OBPgpLYS (SEQ ID NO: 47) and modified endolysin PKOBPgpLYS (SEQ ID NO: 49) each in combination without and with 0.5 mM EDTA. For incubation, the endolysins were used each in buffer (20 mM $NaH_2P0_4$-NaOH pH7.4; 0.5 M NaCl; 0.5 M imidazole) and the incubation took place at a final concentration of endolysin of 1,313 μM. As a control each strain was also incubated for 30 minutes with 0.5 mM EDTA (in same buffer as outlined above) but no endolysin. After incubation cell suspensions were diluted three times (respectively $10^5$-$10^4$-$10^3$ cells/ml) and 100 μl of each dilution was plated out on LB-medium. The residual colonies were counted after an overnight incubation at 37° C. Based on the counted cell numbers the antibacterial activity as the relative inactivation in logarithmic units ($=\log_{10}N_0/N_i$ with $N_0$=number of untreated cells and $N_i$=number of treated cells, both counted after incubation) was calculated (Table 2). All samples were replicated in threefold. Averages +/− standard deviations are represented. The maximal reduction observed is dependent on the detection level of 10 cells/ml and the initial cell density.

TABLE 2

Antibacterial activity of unmodified endolysin (OBPgpLYS) and its modified endolysin variant (PKOBPgpLYS) with and without EDTA-$Na_2$ on different exponential growing Gram-negative species in logarithmic units.

| | 0.5 mM EDTA | 1.313 μM OBPgpLYS | 1.313 μM PKOBPgpLYS | 1.313 μM OBPgpLYS + 0.5 mM EDTA | 1.313 μM PKOBPgpLYS + 0.5 mM EDTA |
|---|---|---|---|---|---|
| *P. aeruginosa* PAO1p | 0.130 +/− 0.023 | 2.531 +/− 0.173 | 3.079 +/− 0.015 | 4.357 +/− 1.857 | >5.687 |
| *P. aeruginosa* Br667 | 0.031 +/− 0.023 | 1.082 +/− 0.083 | 1.163 +/− 0.063 | 3.144 +/− 0.223 | 5.272 +/− 0.573 |
| *P. putida* G1 | 0.412 +/− 0.055 | 0.141 +/− 0.027 | 0.904 +/− 0.079 | 4.891 +/− 0.000 | >4.891 |

TABLE 2-continued

Antibacterial activity of unmodified endolysin (OBPgpLYS) and its modified endolysin variant (PKOBPgpLYS) with and without EDTA-$Na_2$ on different exponential growing Gram-negative species in logarithmic units.

| | 0.5 mM EDTA | 1.313 μM OBPgpLYS | 1.313 μM PKOBPgpLYS | 1.313 μM OBPgpLYS + 0.5 mM EDTA | 1.313 μM PKOBPgpLYS + 0.5 mM EDTA |
|---|---|---|---|---|---|
| *Burkholderia pseudomallei* | 0.220 +/− 0.081 | 0.997 +/− 0.131 | 1.806 +/− 0.287 | 4.08 +/− 0.301 | >4.861 |
| *Escherichia coli* WK6 | 0.592 +/− 0.113 | 0.681 +/− 0.032 | 1.434 +/− 0.018 | 1.179 +/− 0.200 | 1.695 +/− 0.147 |
| *Salmonella typhimurium* | 0.054 +/− 0.048 | 0.076 +/− 0.011 | 0.127 +/− 0.013 | 0.774 +/− 0.052 | 0.908 +/− 0.037 |

While the global efficacy of the OBPgpLYS treatment is species dependent, the results in Table 2 show an added effect of the PKOBPgpLYS compared to unmodified OBPgpLYS for all bacterial species tested, both in the absence as the presence of 0.5 mM EDTA. For *Pseudomonas* and *Burkholderia* species, a clear synergistic effect with EDTA is observed for the PKOBPgpLYS activity.

TABLE 3

List of used Gram-negative strains

| Gram-negative strain | Source | Reference |
|---|---|---|
| *Pseudomonas aeruginosa* PAO1p | Burn wound isolate, Queen Astrid Hospital, Brussels | Pirnay et al., 2003* |
| *Pseudomonas aeruginosa* Br667 | Burn wound isolate, Queen Astrid Hospital, Brussels | Pirnay et al., 2003* |
| *Pseudomonas putida* G1 | Soil isolate, Moskow | Prof V. Krylov** |
| *Burkholderia pseudomallei* | Clinical isolate, UZ Gasthuisberg, Leuven | Prof J. Verhaegen*** |
| *Escherichia coli* WK6 | Standard laboratory expression strain | Stratagene**** |
| *Salmonella typhimurium* LT2 | SGSC No 2317 | Prof C. Michiels***** |

*Pirnay J P, De Vos D, Cochez C, Bilocq F, Pirson J, Struelens M, Duinslaeger L, Cornelis P, Zizi M, Vanderkelen A. (2003). Molecular epidemiology of *Pseudomonas aeruginosa* colonization in a burn unit: persistence of a multidrug-resistant clone and a silver sulfadiazine-resistant clone. J Clin Microbiol, 41(3): 1192-1202.

**State Research Institute for Genetics and Selection of Industrial Microorganisms, Moscow 113545, 1st Dorozhnii projezd, 1, Russia

***Afd. Experiment. Laboratoriumgeneesk., UZ Herestraat 49 - bus 7003, 3000 Leuven, Belgium

****STANSSENS, P., OPSOMER, C., MCKEOWNY, M., KRAMER, W., ZABEAU, M. and FRITZ, H.-J. (1989). Efficient oligonucleotide-directed construction of mutations in expression vectors by the gapped duplex D N A method using alternating selectable markers. NucleiC Acids Research 17, 4441-4454.

*****Centr. Levensmidd.- & Microb. Technol., Kasteelpark Arenberg 23 - bus 2457, 3001 Heverlee, Belgium

EXAMPLE 2

Effect of Different EDTA Concentrations on the Antibacterial Activity of OBPgpLYS and PKOBPgpLYS To determine the influence of EDTA on the antibacterial activity of unmodified and modified endolysins the antibacterial activity of the unmodified OBPgpLYS endolysin (SEQ ID NO: 47) and the PKOBPgpLYS endolysin (SEQ ID NO: 49) was tested on *Pseudomonas aeruginosa* PAO1p cells (Pirnay J P et al. *J Clin Microbiol.,* 41(3):1192-1202 (2003)) using different concentrations of EDTA and endolysins. Exponential growing bacterial cells ($OD_{600\ nm}$ of 0.6) were 100-fold diluted to a final density of about $10^6$ cells/ml and incubated for 30 minutes at room temperature without shaking with unmodified endolysin OBPgpLYS (SEQ ID NO: 47) and modified endolysin PKOBPgpLYS (SEQ ID NO: 49). For incubation, the endolysins were used each in buffer (20 mM $NaH_2P0_4$-NaOH pH7.4; 0.5 M NaCl; 0.5 M imidazole) at final concentrations of endolysin of 0.013 μM, 0.131 μM and 1.315 μM. Thereby, the following different EDTA concentrations were used: 0 mM, 0.05 mM, 0.5 mM and 10 mM.

As a control one sample was also incubated for 30 minutes with no endolysin, instead of there was buffer (20 mM $NaH_2P0_4$-NaOH pH7.4; 0.5 M NaCl; 0.5 M imidazole) added. After incubation cell suspensions were diluted three times (respectively $10^5$-$10^4$-$10^3$ cells/ml) and 100 μl of each dilution was plated out on LB-medium. The residual colonies were counted after an overnight incubation at 37° C. Based on the counted cell numbers the antibacterial activity as the relative inactivation in logarithmic units ($=\log_{10}N_0/N_i$ with $N_0$=number of untreated cells and $N_i$=number of treated cells, both counted after incubation) was calculated (Table 4). All samples were replicated in threefold. Averages +/− standard deviations are represented. The maximal reduction observed (5.69 log units) is dependent on the detection level of 10 cells/ml and the initial cell density. "Δ" gives the difference of activity between the respective OBPgpLYS and PKOBPgpLYS samples.

TABLE 4

Antibacterial activity of unmodified endolysin (OBPgpLYS) and its modified endolysin variant (PKOBPgpLYS) in combination with different EDTA-$Na_2$ concentrations on exponential growing *Pseudomonas aeruginosa* PAO1p cells in logarithmic units

| | Concentration of EDTA-$Na_2$ (in mM) | | | |
|---|---|---|---|---|
| | 0 | 0.05 | 0.5 | 10 |
| No endolysin | / | 0.028 +/− 0.008 | 0.130 +/− 0.023 | 1.827 +/− 0.052 |
| 0.013 μM OBPgpLYS | 0.956 +/− 0.110 | / | 4.626 +/− 0.287 | / |
| 0.013 μM PKOBPgpLYS | 0.992 +/− 0.181 | / | 5.204 +/− 0.000 | / |
| Δ | 0.036 | | 0.578 | |
| 0.131 μM OBPgpLYS | 2.158 +/− 0.027 | / | 4.599 +/− 0.275 | / |
| 0.131 μM PKOBPgpLYS | 2.529 +/− 0.184 | / | 5.671 +/− 0.000 | / |
| Δ | 0.371 | | 1.072 | |
| 1.315 μM OBPgpLYS | 2.531 +/− 0.173 | 2.762 +/− 0.091 | 4.357 +/− 1.857 | 4.888 +/− 0.275 |
| 1.315 μM PKOBPgpLYS | 3.079 +/− 0.015 | 4.145 +/− 0.015 | >5.687 | >5.687 |
| Δ | 0.548 | 1.383 | >1.330 | >0.799 |

As shown in Table 4 unmodified endolysin OBPgpLYS reduces cell numbers significantly with more than 2.5 log units for 1.315 μM and with +/−1 log unit for 0.013 μM, compared to the negative control. Modified endolysin PKOBPgpLYS results in an added 0.5 log units reduction for exponentially growing PAO1p cells. The observed antibacterial effect can be increased to more as 5.69 log units reduction (beneath the detection level) by combining PKOBPgpLYS with the outer membrane permeabilizer EDTA-$Na_2$ at a concentration of 0.5 and 10 mM EDTA. The difference in activity between the unmodified OBPgpLYS and the PK-modified OBPgpLYS increases by raising the amount of added endolysin (from 0.013-1.315 μM endolysin).

EXAMPLE 3

Cloning, Expression and Purification of an OBPgpLYS Derivative Modified with Various Peptide Stretches on the N-Terminus of the Endolysin The OBPgpLYS derivative according to SEQ ID NO:86 is a modular endolysin originating from *Pseudomonas putida* phage OBP with an N-terminal peptidoglycan binding and C-terminal catalytic domain. The OBPgpLYS derivative is encoded by the nucleic acid molecule according to SEQ ID NO: 101. Purified Plasmid DNA (see Example 1) was used to produce a nucleic acid molecule according to SEQ ID NO: 101 with a BamH I (5'-GGA TCC-3') restriction site at the 5'-end of the nucleic acid molecule and an Xho I (5'-CTC GAG-3') restriction site at the 3'-end of the nucleic acid molecule.

The following peptide stretches in table 5 were used for production of fusion proteins with the endolysin OBPgpLYS derivative. The resulting fusion proteins are also listed in table 5.

TABLE 5

Peptide stretches and their respective nucleic acid sequence for production of specific fusion proteins

| Peptide stretch | Nucleic acid molecule encoding the peptide stretch | Amino acid sequence of resulting fusion protein |
|---|---|---|
| Ascaphine (SEQ ID NO: 50) | SEQ ID NO: 90 | SEQ ID NO: 55 |
| Apidaecine (SEQ ID NO: 51) | SEQ ID NO: 91 | SEQ ID NO: 57 |
| Sarcotoxin IA (SEQ ID NO: 17) | SEQ ID NO: 92 | SEQ ID NO: 63 |
| SMAP-29 (SEQ ID NO: 12) | SEQ ID NO: 93 | SEQ ID NO: 65 |
| Cecropin A (*A. aegypti*) (SEQ ID NO: 15) | SEQ ID NO: 94 | SEQ ID NO: 67 |

The nucleic acid molecules encoding the respective peptide stretches were synthetically produced with a Nde I (5'-CAT ATG-3') restriction site at the 5'-end of the nucleic acid molecule and a BamH I (5'-GGA TCC-3') restriction site at the 3'-end of the nucleic acid molecule.

Fusion proteins are constructed by linking at least two nucleic acid sequences using standard cloning techniques as described e.g. by Sambrook et al. 2001, Molecular Cloning: A Laboratory Manual. Therefore the nucleic acid molecules encoding the peptide stretches were cleaved in a digest with the respective restriction enzymes Nde I and BamH I. Subsequently the cleaved nucleic acids encoding the peptide stretches were ligated into the pET21 b expression vector (Novagen, Darmstadt, Germany), which was also cleaved in a digest with the respective restriction enzymes Nde I and BamH I before.

Afterwards, the nucleic acid molecule encoding the endolysin OBPgpLYS derivative was cleaved in a digest with the restriction enzyme BamH I and Xho I, so that the endolysin could be ligated into the pET21b expression vector (Novagen, Darmstadt, Germany).

Thus, the nucleic acid molecule encoding the peptide stretch is ligated into the respective vector at the 5'-end of the nucleic acid molecule encoding the endolysin OBPgpLYS derivative. Moreover, the nucleic acid molecule encoding the endolysin OBPgpLYS derivative is ligated into the respective plasmid, so that a nucleic acid molecule encoding a $His_6$-tag consisting of six histidine residues is associated at the 3'-end of the nucleic acid molecule encoding the endolysin.

The sequence of the endolysin-peptide-fusions was controlled via DNA-sequencing and correct clones were transformed into *E. coli* T7 Express lysY/Iq (New England Biolabs, Frankfurt, Germany) for protein expression.

Recombinant expression of the fusion proteins according to SEQ ID NO: 55, 57, 63, 65, 67 is performed in *E. coli* T7 Express lysY/Iq (New England Biolabs, Frankfurt, Germany). The cells were growing until an optical density of OD600 nm of 0.5-0.8 was reached. Then the expression of the fusion protein was induced with 0.5 mM IPTG (isopropylthiogalactoside) and the expression was performed at 37° C. for a period of 4 hours.

Cells were harvested by centrifugation for 15 min at 4000 g and disrupted via sonication on ice. Soluble and insoluble fraction of the *E. coli* crude extract were separated by centrifugation (Sorvall, SS34, 30 min, 15000 rpm). All proteins were purified by $Ni^{2+}$ affinity chromatography (Äkta FPLC, GE Healthcare) using the C-terminal 6× His-tag, encoded by the pET21b vector.

The $Ni^{2+}$ affinity chromatography is performed in 4 subsequent steps, all at room temperature:

1. Equilibration of the Histrap FF 5 ml column (GE Healthcare) with up to 10 column volumes of Washing Buffer (20 mM imidazole, 1 M NaCl and 20 mM Hepes on pH 7.4) at a flow rate of 3-5 ml/min.
2. Loading of the total lysate (with wanted fusion protein) on the Histrap FF 5 ml column at a flow rate of 3-5 ml/min.
3. Washing of the column with up to 10 column volumes of Washing Buffer to remove unbound sample followed by a second washing step with 10% Elution buffer (500 mM imidazole, 0.5 M NaCl and 20 mM Hepes on pH 7.4) at a flow rate of 3-5 ml/min.
4. Elution of bounded fusion proteins from the column with a linear gradient of 4 column volumes of Elution Buffer (500 mM imidazole, 0.5 M NaCl and 20 mM Hepes on pH 7.4) to 100% at a flow rate of 3-5 ml/min.

Purified stock solutions of fusion proteins in Elution Buffer (20 mM Hepes pH 7.4; 0.5 M NaCl; 500 mM imidazole) were at least 60% pure as determined visually on SDS-PAGE gels (data not shown).

EXAMPLE 4

Antimicrobial Activity of the Endolysin OBPgpLYS Derivative Modified with Various Peptide Stretches on the N-Terminus

*Acinetobacter baumannii* DSMZ 30007 and *Pseudomonas aeruginosa* PAO1p cells (Burn wound isolate, Queen Astrid Hospital, Brussels; Pirnay J P et al. (2003), world-wide-web at ncbi.nlm.nih.gov/pubmed/12624051?ordinalpos=3&itool=EntrezSystem2.PEntrez.Pubmed.Pubmed_ResultsPanel.Pubmed_DefaultReportPanel.Pubmed_RVDocSum *J Clin Microbiol.*, 41(3):1192-1202) were used as test strains. Overnight cultures were diluted 10-fold in fresh LB medium and grown to $OD_{600}$=0.6. The culture was spun down and diluted 10-fold in dilution buffer (10 mM HEPES, 0.5 mM EDTA; pH 7.4). Bacteria were incubated at room temperature with each 10 µg undialyzed fusion protein at a final concentration of 100 µg/ml in buffer (20 mM $NaH_2P0_4$—NaOH pH 7.4; 0.5 M NaCl; 0.5 M imidazole). After 1 hour cell dilution series were made in PBS and plated on LB. Additionally, a negative control was plated using buffer (20 mM $NaH_2P0_4$—NaOH pH 7.4; 0.5 M NaCl; 0.5 M imidazole). The residual colonies were counted after an overnight incubation at 37° C. Based on the counted cell numbers the antibacterial activity as logarithmic units (=$\log_{10}N_0/N_i$ with $N_0$=number of untreated cells and $N_i$=number of treated cells) was calculated (Table 5). All samples were replicated at least in four fold.

TABLE 6

Antimicrobial activity of the OBPgpLYS derivative modified with various peptide stretches against gram-negative bacteria

| Fusion protein | Enzyme part | Peptide stretch (N-terminal unless otherwise indicated) | Activity against *Acinetobacter baumannii* DSMZ 30007 | Activity against *Pseudomonas aeruginosa* PAO1p cells |
|---|---|---|---|---|
| SEQ ID NO: 88 | SEQ ID NO: 87 | — | ++ | + |
| SEQ ID NO: 55 | SEQ ID NO: 87 | Ascaphine (SEQ ID NO: 50) | +++ | Not determined |
| SEQ ID NO: 57 | SEQ ID NO: 87 | Apidaecine (SEQ ID NO: 51) | +++ | Not determined |
| SEQ ID NO: 63 | SEQ ID NO: 87 | Sarcotoxin IA (SEQ ID NO: 17) | +++ | ++ |
| SEQ ID NO: 65 | SEQ ID NO: 87 | SMAP-29 (SEQ ID NO: 12) | +++ | ++ |
| SEQ ID NO: 67 | SEQ ID NO: 87 | Cecropin A (SEQ ID NO: 15) | +++ | +++ |

Abreviations: +: 1 log; ++: 2-3 log; +++: 4 or more logs; not determined means that this strain was not tested with the respective fusion protein.

The fusion proteins in Table 6 without any tag and linker were also tested with the activity assays described above. They all showed antimicrobial activity against the used bacterial strains in Table 6.

EXAMPLE 5

N-Terminal Antibacterial Peptide Fusion to Endolysin of *Pseudomonas putida* Phage OBP OBPgpLys derivative, the modular endolysin of *P. putida* phage OBP, was N-terminally fused to a set of natural antibacterial peptide tags (Table 7) in order to investigate its anti Gram-negative activity.

TABLE 7

List of antibacterial peptide tags which were fused to the OBPgpLYS derivative

| Tag | Description + size | Amino acid sequence | Nucleic acid sequence | Reference |
|---|---|---|---|---|
| α4-helix of T4-lysozyme | Amphipathic helix (13 aa) | PNRAKRVITTFRT (SEQ ID NO: 68) | SEQ ID NO: 95 | Matthews et al., 1974* |
| Pentapeptide (designed) | Hydrophobic (5 aa) | FFVAP (SEQ ID NO: 18) | SEQ ID NO: 96 | Briers Y (not published |
| Artilysin1 (designed) | Hydrophobic (18 aa) | GFFIPAVILPSIAFLIVP (SEQ ID NO: 70) | SEQ ID NO: 97 | Walmagh, M. (Not published) |
| Artilysin 2 (designed) | Amphipathic helix (25 aa) | GKPGWLIKKALVFKKLIRRPLKRLA (SEQ ID NO: 71) | SEQ ID NO: 98 | Walmagh, M (Not published) |
| Parasin 1 | Alpha-helical peptide (19 aa) | KGRGKQGGKVRAKAKTRSS (SEQ ID NO: 72) | SEQ ID NO: 99 | Park, Y et al., 1998** |
| Lycotoxin 1 | Amphiphatic helix (25 aa) | IWLTALKFLGKHAAKKLAKQQLSKL (SEQ ID NO: 73) | SEQ ID NO: 100 | Yan & Adams, 1988*** |

*Matthews, B. W. and Remington, S. J. (1974). The three dimensional structure of the lysozyme from bacteriophage T4. *Proc. Natl. Acad. Sci. U.S.A.*, 71: 4178-4182

**In Yup Park, Chan Bae Park, Mi Sun Kim, Sun Chang Kim (1998). Parasin I, an antimicrobial peptide derived from histone H2A in the cat¢sh, *Parasilurus asotus*. FEBS Letters 437 258-262

***Yan, L and Adams, M. A. (1998). Lycotoxins, Antimicrobial Peptides from Venom of the Wolf Spider, *Lycosa carolinensis J. Biol. Chem*, 273: 2059-2066.

Methodology of Tag Modification of the OBPgpLys Derivative

Except for the pentapeptide tag, all antibacterial peptide tags were fused to the ORF which encodes for the OBPgpLYS derivative using an adapted version of the Ligation Independent Cloning (LIC) as e.g. described in Berrow et al. 2007. Here fore, an unique Ecl136II restriction site was inserted in front of the WT endolysin gene by a tail PCR with a specific designed 5' primer (5'-GGAATGGGGAGCTCCTC-CAAAAATAGCGAGAAG-3'; SEQ ID NO:102) and the standard OBPgpLys derivative reverse primer (5'-AACTAT-TCCGTGTGCTTTCTTTGT-3'; SEQ ID NO:103) on pure genomic DNA of phage OBP. This extended fragment was then ligated in the pEXP5CT/TOPO® expression vector (Invitrogen, Carlsbad, Calif., USA) by following the TA cloning protocol of the manufacturer. Pure plasmid was cutted once in an Ecl136II restriction digest and hybridized peptide cassettes (created by hybridization of primer pairs, see Table 8) were inserted into the cutted plasmid without a necessary ligation step (LIC). For the N-terminal pentapeptide tag fusion a tail PCR with an extended 5' primer which encodes for this pentapeptide (5'-ATGGGATCCTTCTTCGTAGCA CCGGGCTCCTCCAAAAATAGCGAGAAG-3'; SEQ ID NO:104) and the standard OBPgpLys derivative reverse primer (5'-AACTATTCCGTGTGCTTTCTTTGT-3'; SEQ ID NO:103) was applied on phage OBP genomic DNA. Correct insertion of the fragments in the expression vector was verified by sequencing analysis before introducing the construct into a suitable *Escherichia coli* BL21(DE3)pLysS expression strain.

TABLE 8

Used primer pairs for hybridization of antibacterial peptide tags to ORF encoding the OBPgpLys derivative

| Tag | forward primer | reverse primer |
|---|---|---|
| α4-helix of T4-lysozyme | 5' TTGGAATGGGGAGCCCGAACCGTGCAAAACG TGTAATCA 3'; SEQ ID NO: 105 | 5' TATTTTTGGAGGAGCCGGTACGGAAGGTGGTGAT TACACGTT 3'; SEQ ID NO: 106 |
| Artilysin1 (designed) | 5' TTATGGGCTTCTTCATCCCGGCAGTAATCCTGC CCTCCA 3'; SEQ ID NO: 107 | 5' TATTTTTGGATCTGCCGCCCGGTACGATCAGGAAT GCGATGGAGGGCAGGATT 3'; SEQ ID NO: 108 |

TABLE 8 -continued

| Used primer pairs for hybridization of antibacterial peptide tags to ORF encoding the OBPgpLys derivative | | |
|---|---|---|
| Tag | forward primer | reverse primer |
| Artilysin 2 (designed) | 5' TTATGGGCAAACCGGGCTGGCTGATCAAAAG GCACTGGTATTCAAGA 3'; SEQ ID NO: 109 | 5' TATTTTTGGATCTGCCGCCTGCCAGTCTCTTCAGC GGACGACGGATCAGTTTCTTGAATACCAG 3'; SEQ ID NO: 110 |
| Parasin 1 | 5' TTGGAATGGGGAGCAAAGGCCGTGGCAAGCA GGGAGGCAAAGTACGTG 3'; SEQ ID NO: 111 | 5' TATTTTTGGAGGAGCCTGAGGAACGGGTCTTTGCT TTTGCACGTACTTTGC 3'; SEQ ID NO: 112 |
| Lycotoxin 1 | 5' GGAATGGGGAGCATCTGGCTGACCGCACTGA AATTCCTCGGCAAACACGCCGCAA 3'; SEQ ID NO: 113 | 5' TATTTTTGGAGGAGCCCAGTTTGGATAATTGCTGT TTTGCCAGTTTCTTTGCGGCGTGTT 3'; SEQ ID NO: 114 |

Large Scale Recombinant Expression of Modified OBPgpLYS Derivative Fusion Variants Standard expression is performed in Lysogeny Broth (LB) in exponentially growing cells (OD600 nm=0.6) induced with 1 mM isopropyl-beta-D-thiogalactopyranoside. Expression parameters like temperature, time and expression strain varied on a protein specific basis in order to optimize the soluble expression levels of the modified endolysins (see Table 9).

For purification, cells from an expression culture (500-600 ml) are harvested (4500 rpm, 30 min, 4° C.) and resuspended in 1/25 volumes of lysis buffer (10 mM imidazole, 20 mM NaH2PO4, 0.5 M NaCl, pH 7.4). This suspension is frozen/thawed three times prior to sonication (8×30 s, amplitude 40% on a Vibra Cell™, Sonics, Dandurry, Conn., USA) and filtered through 0.45 and 0.22 μm Durapore membrane filters (Millipore, Billerica, Mass., USA). Purification of the His-tagged fusion protein was performed by a one-step protocol employing Ni2+—affinity chromatography (HisTrap HP 1 ml column, GE Healthcare, Buckinghamshire, UK) according to the manufacturer's instructions. The Ni2+ affinity chromatography is performed in 4 subsequent steps, all on room temperature:

1. Equilibration of the Histrap HP 1 ml column (GE Healthcare) with 10 column volumes of Washing Buffer (60 mM imidazole, 0.5 mM NaCl and 20 mM NaH2P04-NaOH on pH 7.4) at a flow rate of 0.5 ml/min.
2. Loading of the total lysate (with wanted endolysin) on the Histrap HP 1 ml column at a flow rate of 0.5 ml/min.
3. Washing of the column with 15 column volumes of Washing Buffer at a flow rate of 1 ml/min.
4. Elution of bounded endolysin from the column with 10 column volumes of Elution Buffer (500 mM imidazole, 0.5 M NaCl and 20 mM NaH2P04-NaOH on pH 7.4) at a flow rate of 0.5 ml/min The wash buffer included a low imidazole concentration which varied on protein specific base to ensure higher purity of the protein (see Table 9). The total yields of recombinant proteins per liter *E. coli* expression culture is also shown in Table 3. The values were determined by spectrophotometric measurement of the protein concentration and the total volume of the purified stock solution at a wavelength of 280 nm. Purified stock solutions were at least 60% pure as determined visually on SDS-PAGE gels.

TABLE 9

Expression parameters and obtained protein yields per liter expression culture of N-terminal modified endolysins. RP = *E. coli* BL21(DE3)pLysS Codon min RP strain, RIL = *E. coli* BL21(DE3)pLysS Codon Plus RIL strain

| Modified endolysin | Temperature/time | Protein Yield (in mg/l) | [imidazole] (in mM) |
|---|---|---|---|
| α4-OBPgpLys (SEQ ID NO: 75) | 16/overnight | 1.28 | 60 |
| Pentapeptide-OBPgpLys (SEQ ID NO: 77) | 16/overnight | 1.10 | 65 |
| Artilysin1-OBPgpLys (SEQ ID NO: 79) | 16/overnight | <0.1 | 50 |
| Artilysin2-OBPgpLys (SEQ ID NO: 81) | 16/overnight | 1.32 | 50 |
| Parasin1-OBPgpLys (SEQ ID NO: 83) | 16/overnight | 0.38 | 50 |
| Lycotoxin1-OBPgpLys (SEQ ID NO: 85) | 16/overnight | 1.71 | 50 |

In Vitro Antibacterial Activity and Host Range of Modified OBPgpLys Derivative Variants Exponential growing Gram-negative bacterial cells (OD600 nm=0.6) were 100-fold diluted to a final density of about 106 cells/ml and incubated for 30 minutes at room temperature without shaking with the different modified OBPgpLYS derivative variants. After incubation cell suspensions were diluted three times (respectively 105-104-103 cells/ml) and 100 μl of each dilution was plated out on LB-medium. The residual colonies were counted after an overnight incubation on 37° C. Based on the counted cell numbers the antibacterial activity as the relative inactivation in logarithmic units (=log $10N_0/N_i$ with $N_0$=number of untreated cells and $N_i$=number of treated cells, both counted after incubation) is calculated (Table 10). All samples were replicated in threefold. Averages +/− standard deviations are represented.

TABLE 10

In vitro antibacterial activity of different modified OBPgpLYS derivative variants on a range of exponential growing Gram-negative species with 0.5 mM EDTA. Initial density is $10^6$ cells/ml and incubation proceeds for 30 minutes without shaking at RT. Protein concentration is 1500 nM, except for Artilys1-OBPgplys (800 nM).

| | *P. aeruginosa* PAO1p | *P. putida* G1 | *E. coli* Xl-1 | *Salmonella typhimurium* LT2 |
|---|---|---|---|---|
| 1500 nM α4-OBPgpLys (SEQ ID NO: 75) | ++ | ++ | ++ | + |
| 1500 nM Pentapeptide-OBPgpLys (SEQ ID NO: 77) | ++ | +++ | ++ | + |
| 800 nM Artilysin1-OBPgpLys (SEQ ID NO: 79) | Not determined | ++ | + | + |
| 1500 nM Artilysin2-OBPgpLys (SEQ ID NO: 81) | ++ | ++ | ++ | + |
| 1500 nM Parasin1-OBPgpLys (SEQ ID NO: 83) | +++ | +++ | +++ | ++ |
| 1500 nM Lycotoxin1-OBPgpLys (SEQ ID NO: 85) | ++ | +++ | ++ | + |
| 1500 nM OBPgpLYS (SEQ ID NO: 88) | + | + | + | + |

Abreviations: +: about 0.5 log; ++: 1-2 log; +++: 3-4 or more logs; not determined means that this strain was not tested with the respective fusion protein.

The invention claimed is:

1. A vector comprising a polynucleotide encoding a polypeptide and a nucleic acid that is heterologous to the polynucleotide, wherein the polypeptide comprises the amino acid sequence of SEQ ID NO: 1, or a fragment thereof, wherein the fragment comprises an amino acid sequence selected from the group consisting of SEQ ID NO: 4 and 5, or comprises the amino acid sequences of SEQ ID NO: 4 and 5.

2. An isolated host cell comprising the vector according to claim 1.

3. A composition comprising the vector of claim 1.

4. A vector comprising a polynucleotide encoding a fusion protein and a nucleic acid that is heterologous to the polynucleotide, wherein the fusion protein comprises (i) a polypeptide comprising the amino acid sequence of SEQ ID NO: 1, or a fragment thereof, wherein the fragment comprises an amino acid sequence selected from the group consisting of SEQ ID NO: 4 and 5, or comprises the amino acid sequences of SEQ ID NO: 4 and 5, and (ii) a peptide fused to said polypeptide at the N- or C-terminus, wherein said peptide is a cationic peptide, polycationic peptide, amphipathic peptide, sushi peptide, defensin, hydrophobic peptide and/or an antimicrobial peptide.

5. An isolated host cell comprising the vector according to claim 4.

6. The vector according to claim 4, wherein said peptide comprises 5 to 100 amino acid residues, 5 to 50 amino acid residues, or 5 to 30 amino acid residues.

7. The vector according to claim 4, wherein said peptide is a cationic and/or polycationic peptide, wherein said cationic and/or polycationic peptide comprises at least one amino acid residue selected from the group consisting of arginine, histidine and lysine residues, optionally wherein at least 70% of the amino acid residues in said peptide are arginine, histidine and/or lysine residues.

8. The vector according to claim 4, wherein the peptide is an amphipathic peptide, wherein said amphipathic peptide comprises at least one positively charged amino acid residue selected from the group consisting of lysine, arginine and histidine residues, combined to at least one hydrophobic amino acid residue selected from the group consisting of valine, isoleucine, leucine, methionine, phenylalanine, tryptophan, cysteine, alanine, tyrosine, histidine, threonine, serine, proline and glycine residues, optionally wherein at least 70% of the amino acid residues in said amphipathic peptide are either arginine or lysine residues and at least 30% of the amino acid residues in said amphipathic peptide are valine, isoleucine, leucine, methionine, phenylalanine, tryptophan, cysteine, alanine, tyrosine, histidine, threonine, serine, proline or glycine residues.

9. The vector according to claim 4, wherein the peptide comprises an amino acid sequence selected from the group consisting of SEQ ID NO: 6-38 and 39.

10. The vector according to claim 4, wherein said fusion protein comprises an amino acid sequence selected from the group consisting of SEQ ID NO: 43 and 49.

11. A composition comprising the vector according to claim 4.

12. The vector according to claim 1, wherein the polypeptide comprises a fragment of the amino acid sequence of SEQ ID NO: 1, wherein the fragment comprises an amino acid sequence selected from the group consisting of SEQ ID NO: 4 and 5, or comprises the amino acid sequences of SEQ ID NO: 4 and 5.

13. A vector comprising a polynucleotide encoding a polypeptide and a nucleic acid that is heterologous to the polynucleotide, wherein the polypeptide comprises the amino acid sequence of SEQ ID NO: 86 or 87.

14. The vector according to claim 1, wherein the polypeptide further comprises a tag, optionally wherein the tag is a $His_6$-tag.

15. The vector according to claim 14, wherein said polypeptide comprises the amino acid sequence according to SEQ ID NO: 47.

* * * * *

SEQUENCE LISTING

```
<160> NUMBER OF SEQ ID NOS: 119

<210> SEQ ID NO 1
<211> LENGTH: 328
<212> TYPE: PRT
<213> ORGANISM: unknown
<220> FEATURE:
<223> OTHER INFORMATION: OBPgpLYS

<400> SEQUENCE: 1

Met Lys Asn Ser Glu Lys Asn Ala Ser Ile Ile Met Ser Ile Gln Arg
1               5                   10                  15

Thr Leu Ala Ser Leu Ser Leu Tyr Gly Gly Arg Ile Asp Gly Leu Phe
            20                  25                  30

Gly Glu Lys Cys Arg Gly Ala Ile Ile Leu Met Leu Asn Lys Val Tyr
        35                  40                  45

Pro Asn Phe Ser Thr Asn Lys Leu Pro Ser Asn Thr Tyr Glu Ala Glu
    50                  55                  60

Ser Val Phe Thr Phe Leu Gln Thr Ala Leu Ala Gly Val Gly Leu Tyr
65                  70                  75                  80

Thr Ile Thr Ile Asp Gly Lys Trp Gly Gly Thr Ser Gln Gly Ala Ile
                85                  90                  95

Asp Ala Leu Val Lys Ser Tyr Arg Gln Ile Thr Glu Ala Glu Arg Ala
            100                 105                 110

Gly Ser Thr Leu Pro Leu Gly Leu Ala Thr Val Met Ser Lys His Met
        115                 120                 125

Ser Ile Glu Gln Leu Arg Ala Met Leu Pro Thr Asp Arg Gln Gly Tyr
    130                 135                 140

Ala Glu Val Tyr Ile Asp Pro Leu Asn Glu Thr Met Asp Ile Phe Glu
145                 150                 155                 160

Ile Asn Thr Pro Leu Arg Ile Ala His Phe Met Ala Gln Ile Leu His
                165                 170                 175
```

-continued

```
Glu Thr Ala Cys Phe Lys Tyr Thr Glu Glu Leu Ala Ser Gly Lys Ala
            180                 185                 190

Tyr Glu Gly Arg Ala Asp Leu Gly Asn Thr Arg Pro Gly Asp Gly Pro
        195                 200                 205

Leu Phe Lys Gly Arg Gly Leu Leu Gln Ile Thr Gly Arg Leu Asn Tyr
    210                 215                 220

Val Lys Cys Gln Val Tyr Leu Arg Glu Lys Leu Lys Asp Pro Thr Phe
225                 230                 235                 240

Asp Ile Thr Ser Ser Val Thr Cys Ala Gln Gln Leu Ser Glu Ser Pro
                245                 250                 255

Leu Leu Ala Ala Leu Ala Ser Gly Tyr Phe Trp Arg Phe Ile Lys Pro
            260                 265                 270

Lys Leu Asn Glu Thr Ala Asp Lys Asp Asp Ile Tyr Trp Val Ser Val
        275                 280                 285

Tyr Val Asn Gly Tyr Ala Lys Gln Ala Asn Pro Tyr Tyr Pro Asn Arg
    290                 295                 300

Asp Lys Glu Pro Asn His Met Lys Glu Arg Val Gln Met Leu Ala Val
305                 310                 315                 320

Thr Lys Lys Ala Leu Gly Ile Val
                325
```

<210> SEQ ID NO 2
<211> LENGTH: 987
<212> TYPE: DNA
<213> ORGANISM: Bacteriophage OBP

<400> SEQUENCE: 2

```
atgaaaaata gcgagaagaa tgcatcgata attatgtcga tacagagaac gctcgcttca     60

ctctcactct atggaggccg catcgacggc ctctttggag agaagtgtcg tggggctatc    120

atcttgatgc tgaataaggt ctatcctaat ttcagcacca acaaacttcc gagtaacaca    180

tatgaagcgg aatccgtgtt cacgtttctc cagactgctt tggctggtgt tggtctttat    240

accattacta ttgatggtaa atggggtggt acttctcaag gtgctattga cgccctcgtc    300

aagtcttacc gtcaaattac cgaagcggag cgagctgggt cgacgttgcc attaggtctt    360

gctactgtga tgtctaagca tatgtctatt gaacagttga gagcaatgct ccctaccgat    420

agacaaggat atgctgaagt ttatatcgat cctttaaatg agacgatgga tatatttgaa    480

ataaatactc cattacgaat tgctcatttc atggcccaaa tcctccacga aacggcgtgt    540

tttaaatata ccgaagaact ggcgagcggt aaggcttatg agggtcgtgc tgatttaggt    600

aatactcgac caggtgatgg accactgttt aaaggtcgtg gattattaca aattaccggg    660

cgactgaatt atgtgaaatg ccaagtgtat ttgagagaga agttaaagga ccctactttc    720

gacattacgt cgtctgtaac ttgtgcccaa cagctctccg aaagtccact tcttgctgca    780

ttggcatcgg gctacttctg gagattcatc aaacctaaac tcaatgaaac ggctgataaa    840

gacgatatct attgggtttc tgtttatgtc aatggttacg ctaaacaagc gaatccttat    900

taccctaacc gggataagga acccaaccat atgaaagaac gtgtccaaat gcttgcagtg    960

acaaagaaag cactcggaat agtttaa                                         987
```

<210> SEQ ID NO 3
<211> LENGTH: 984
<212> TYPE: DNA
<213> ORGANISM: unknown
<220> FEATURE:

<223> OTHER INFORMATION: OBPgpLYS

<400> SEQUENCE: 3

```
atgaaaaata gcgagaagaa tgcatcgata attatgtcga tacagagaac gctcgcttca     60
ctctcactct atggaggccg catcgacggc ctctttggag agaagtgtcg tggggctatc    120
atcttgatgc tgaataaggt ctatcctaat ttcagcacca acaaacttcc gagtaacaca    180
tatgaagcgg aatccgtgtt cacgtttctc cagactgctt tggctggtgt tggtctttat    240
accattacta ttgatggtaa atggggtggt acttctcaag gtgctattga cgccctcgtc    300
aagtcttacc gtcaaattac cgaagcggag cgagctgggt cgacgttgcc attaggtctt    360
gctactgtga tgtctaagca tatgtctatt gaacagttga gagcaatgct ccctaccgat    420
agacaaggat atgctgaagt ttatatcgat cctttaaatg agacgatgga tatatttgaa    480
ataaatactc cattacgaat tgctcatttc atggcccaaa tcctccacga aacggcgtgt    540
tttaaatata ccgaagaact ggcgagcggt aaggcttatg agggtcgtgc tgatttaggt    600
aatactcgac caggtgatgg accactgttt aaaggtcgtg gattattaca aattaccggg    660
cgactgaatt atgtgaaatg ccaagtgtat ttgagagaga agttaaagga ccctactttc    720
gacattacgt cgtctgtaac ttgtgcccaa cagctctccg aaagtccact tcttgctgca    780
ttggcatcgg gctacttctg gagattcatc aaacctaaac tcaatgaaac ggctgataaa    840
gacgatatct attgggtttc tgtttatgtc aatggttacg ctaaacaagc gaatccttat    900
taccctaacc gggataagga acccaaccat atgaaagaac gtgtccaaat gcttgcagtg    960
acaaagaaag cactcggaat agtt                                           984
```

<210> SEQ ID NO 4
<211> LENGTH: 90
<212> TYPE: PRT
<213> ORGANISM: unknown
<220> FEATURE:
<223> OTHER INFORMATION: PGB of OBPgpLYS

<400> SEQUENCE: 4

```
Asn Ala Ser Ile Ile Met Ser Ile Gln Arg Thr Leu Ala Ser Leu Ser
1               5                   10                  15

Leu Tyr Gly Gly Arg Ile Asp Gly Leu Phe Gly Glu Lys Cys Arg Gly
            20                  25                  30

Ala Ile Ile Leu Met Leu Asn Lys Val Tyr Pro Asn Phe Ser Thr Asn
        35                  40                  45

Lys Leu Pro Ser Asn Thr Tyr Glu Ala Glu Ser Val Phe Thr Phe Leu
    50                  55                  60

Gln Thr Ala Leu Ala Gly Val Gly Leu Tyr Thr Ile Thr Ile Asp Gly
65                  70                  75                  80

Lys Trp Gly Gly Thr Ser Gln Gly Ala Ile
                85                  90
```

<210> SEQ ID NO 5
<211> LENGTH: 167
<212> TYPE: PRT
<213> ORGANISM: unknown
<220> FEATURE:
<223> OTHER INFORMATION: EAD of OBPgpLYS

<400> SEQUENCE: 5

```
Lys His Met Ser Ile Glu Gln Leu Arg Ala Met Leu Pro Thr Asp Arg
1               5                   10                  15
```

-continued

```
Gln Gly Tyr Ala Glu Val Tyr Ile Asp Pro Leu Asn Glu Thr Met Asp
            20                  25                  30

Ile Phe Glu Ile Asn Thr Pro Leu Arg Ile Ala His Phe Met Ala Gln
        35                  40                  45

Ile Leu His Glu Thr Ala Cys Phe Lys Tyr Thr Glu Glu Leu Ala Ser
    50                  55                  60

Gly Lys Ala Tyr Glu Gly Arg Ala Asp Leu Gly Asn Thr Arg Pro Gly
65                  70                  75                  80

Asp Gly Pro Leu Phe Lys Gly Arg Gly Leu Leu Gln Ile Thr Gly Arg
                85                  90                  95

Leu Asn Tyr Val Lys Cys Gln Val Tyr Leu Arg Glu Lys Leu Lys Asp
            100                 105                 110

Pro Thr Phe Asp Ile Thr Ser Ser Val Thr Cys Ala Gln Gln Leu Ser
        115                 120                 125

Glu Ser Pro Leu Leu Ala Ala Leu Ala Ser Gly Tyr Phe Trp Arg Phe
    130                 135                 140

Ile Lys Pro Lys Leu Asn Glu Thr Ala Asp Lys Asp Asp Ile Tyr Trp
145                 150                 155                 160

Val Ser Val Tyr Val Asn Gly
                165


<210> SEQ ID NO 6
<211> LENGTH: 25
<212> TYPE: PRT
<213> ORGANISM: unknown
<220> FEATURE:
<223> OTHER INFORMATION: amphiphatic peptide Pleurocidin

<400> SEQUENCE: 6

Gly Trp Gly Ser Phe Phe Lys Lys Ala Ala His Val Gly Lys His Val
1               5                   10                  15

Gly Lys Ala Ala Leu Thr His Tyr Leu
            20                  25


<210> SEQ ID NO 7
<211> LENGTH: 31
<212> TYPE: PRT
<213> ORGANISM: unknown
<220> FEATURE:
<223> OTHER INFORMATION: amphiphatic peptide Cecropin P1

<400> SEQUENCE: 7

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30


<210> SEQ ID NO 8
<211> LENGTH: 21
<212> TYPE: PRT
<213> ORGANISM: unknown
<220> FEATURE:
<223> OTHER INFORMATION: amphiphatic peptide Buforin II

<400> SEQUENCE: 8

Thr Arg Ser Ser Arg Ala Gly Leu Gln Phe Pro Val Gly Arg Val His
1               5                   10                  15

Arg Leu Leu Arg Lys
            20
```

-continued

<210> SEQ ID NO 9
<211> LENGTH: 39
<212> TYPE: PRT
<213> ORGANISM: unknown
<220> FEATURE:
<223> OTHER INFORMATION: amphiphatic peptide Buforin I

<400> SEQUENCE: 9

```
Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35
```

<210> SEQ ID NO 10
<211> LENGTH: 23
<212> TYPE: PRT
<213> ORGANISM: unknown
<220> FEATURE:
<223> OTHER INFORMATION: amphiphatic peptide Magainin

<400> SEQUENCE: 10

```
Gly Ile Gly Lys Phe Leu His Ser Ala Lys Lys Phe Gly Lys Ala Phe
1               5                   10                  15

Val Gly Glu Ile Met Asn Ser
            20
```

<210> SEQ ID NO 11
<211> LENGTH: 37
<212> TYPE: PRT
<213> ORGANISM: unknown
<220> FEATURE:
<223> OTHER INFORMATION: amphiphatic peptide LL-37

<400> SEQUENCE: 11

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35
```

<210> SEQ ID NO 12
<211> LENGTH: 29
<212> TYPE: PRT
<213> ORGANISM: unknown
<220> FEATURE:
<223> OTHER INFORMATION: antimicrobial peptide SMAP-29

<400> SEQUENCE: 12

```
Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25
```

<210> SEQ ID NO 13
<211> LENGTH: 13
<212> TYPE: PRT
<213> ORGANISM: unknown
<220> FEATURE:
<223> OTHER INFORMATION: antimicrobial peptide Indolicidin

<400> SEQUENCE: 13

-continued

Ile Leu Pro Trp Lys Trp Pro Trp Trp Pro Trp Arg Arg
1 5 10

<210> SEQ ID NO 14
<211> LENGTH: 18
<212> TYPE: PRT
<213> ORGANISM: unknown
<220> FEATURE:
<223> OTHER INFORMATION: antimicrobial peptide Protegrin

<400> SEQUENCE: 14

Arg Gly Gly Arg Leu Cys Tyr Cys Arg Arg Arg Phe Cys Val Cys Val
1 5 10 15

Gly Arg

<210> SEQ ID NO 15
<211> LENGTH: 36
<212> TYPE: PRT
<213> ORGANISM: unknown
<220> FEATURE:
<223> OTHER INFORMATION: antimicrobial peptide Cecropin A (A.aegypti)

<400> SEQUENCE: 15

Gly Gly Leu Lys Lys Leu Gly Lys Lys Leu Glu Gly Ala Gly Lys Arg
1 5 10 15

Val Phe Asn Ala Ala Glu Lys Ala Leu Pro Val Val Ala Gly Ala Lys
20 25 30

Ala Leu Arg Lys
35

<210> SEQ ID NO 16
<211> LENGTH: 40
<212> TYPE: PRT
<213> ORGANISM: unknown
<220> FEATURE:
<223> OTHER INFORMATION: antimicrobial peptide Cecropin A (D. melanogaster)

<400> SEQUENCE: 16

Gly Trp Leu Lys Lys Ile Gly Lys Lys Ile Glu Arg Val Gly Gln His
1 5 10 15

Thr Arg Asp Ala Thr Ile Gln Gly Leu Gly Ile Pro Gln Gln Ala Ala
20 25 30

Asn Val Ala Ala Thr Ala Arg Gly
35 40

<210> SEQ ID NO 17
<211> LENGTH: 39
<212> TYPE: PRT
<213> ORGANISM: unknown
<220> FEATURE:
<223> OTHER INFORMATION: antimicrobial peptide Sarcotoxin IA

<400> SEQUENCE: 17

Gly Trp Leu Lys Lys Ile Gly Lys Lys Ile Glu Arg Val Gly Gln His
1 5 10 15

Thr Arg Asp Ala Thr Ile Gln Gly Leu Gly Ile Ala Gln Gln Ala Ala
20 25 30

Asn Val Ala Ala Thr Ala Arg
35

<210> SEQ ID NO 18
<211> LENGTH: 5

<212> TYPE: PRT
<213> ORGANISM: unknown
<220> FEATURE:
<223> OTHER INFORMATION: synthetic peptide

<400> SEQUENCE: 18

Phe Phe Val Ala Pro
1 5

<210> SEQ ID NO 19
<211> LENGTH: 6
<212> TYPE: PRT
<213> ORGANISM: unknown
<220> FEATURE:
<223> OTHER INFORMATION: synthetic peptide

<400> SEQUENCE: 19

Lys Arg Lys Lys Arg Lys
1 5

<210> SEQ ID NO 20
<211> LENGTH: 9
<212> TYPE: PRT
<213> ORGANISM: unknown
<220> FEATURE:
<223> OTHER INFORMATION: synthetic peptide

<400> SEQUENCE: 20

Lys Arg Lys Lys Arg Lys Lys Arg Lys
1 5

<210> SEQ ID NO 21
<211> LENGTH: 9
<212> TYPE: PRT
<213> ORGANISM: unknown
<220> FEATURE:
<223> OTHER INFORMATION: synthetic peptide

<400> SEQUENCE: 21

Arg Arg Arg Arg Arg Arg Arg Arg Arg
1 5

<210> SEQ ID NO 22
<211> LENGTH: 8
<212> TYPE: PRT
<213> ORGANISM: unknown
<220> FEATURE:
<223> OTHER INFORMATION: synthetic peptide

<400> SEQUENCE: 22

Lys Lys Lys Lys Lys Lys Lys Lys
1 5

<210> SEQ ID NO 23
<211> LENGTH: 10
<212> TYPE: PRT
<213> ORGANISM: unknown
<220> FEATURE:
<223> OTHER INFORMATION: synthetic peptide

<400> SEQUENCE: 23

Lys Arg Lys Lys Arg Lys Lys Arg Lys Lys
1 5 10

<210> SEQ ID NO 24
<211> LENGTH: 12
<212> TYPE: PRT

<213> ORGANISM: unknown
<220> FEATURE:
<223> OTHER INFORMATION: synthetic peptide

<400> SEQUENCE: 24

Lys Arg Lys Lys Arg Lys Lys Arg Lys Lys Arg Lys
1 5 10

<210> SEQ ID NO 25
<211> LENGTH: 14
<212> TYPE: PRT
<213> ORGANISM: unknown
<220> FEATURE:
<223> OTHER INFORMATION: synthetic peptide

<400> SEQUENCE: 25

Lys Arg Lys Lys Arg Lys Lys Arg Lys Lys Arg Lys Lys Arg
1 5 10

<210> SEQ ID NO 26
<211> LENGTH: 16
<212> TYPE: PRT
<213> ORGANISM: unknown
<220> FEATURE:
<223> OTHER INFORMATION: synthetic peptide

<400> SEQUENCE: 26

Lys Lys Lys Lys Lys Lys Lys Lys Lys Lys Lys Lys Lys Lys Lys Lys
1 5 10 15

<210> SEQ ID NO 27
<211> LENGTH: 19
<212> TYPE: PRT
<213> ORGANISM: unknown
<220> FEATURE:
<223> OTHER INFORMATION: synthetic peptide

<400> SEQUENCE: 27

Lys Arg Lys Lys Arg Lys Lys Arg Lys Lys Arg Lys Lys Arg Lys Lys
1 5 10 15

Arg Lys Lys

<210> SEQ ID NO 28
<211> LENGTH: 19
<212> TYPE: PRT
<213> ORGANISM: unknown
<220> FEATURE:
<223> OTHER INFORMATION: synthetic peptide

<400> SEQUENCE: 28

Arg Arg Arg Arg Arg Arg Arg Arg Arg Arg Arg Arg Arg Arg Arg Arg
1 5 10 15

Arg Arg Arg

<210> SEQ ID NO 29
<211> LENGTH: 19
<212> TYPE: PRT
<213> ORGANISM: unknown
<220> FEATURE:
<223> OTHER INFORMATION: synthetic peptide

<400> SEQUENCE: 29

Lys Lys Lys Lys Lys Lys Lys Lys Lys Lys Lys Lys Lys Lys Lys Lys
1 5 10 15

Lys Lys Lys

<210> SEQ ID NO 30
<211> LENGTH: 20
<212> TYPE: PRT
<213> ORGANISM: unknown
<220> FEATURE:
<223> OTHER INFORMATION: synthetic peptide

<400> SEQUENCE: 30

Lys Arg Lys Lys Arg Lys Lys Arg Lys Arg Ser Lys Arg Lys Lys Arg
1 5 10 15

Lys Lys Arg Lys
20

<210> SEQ ID NO 31
<211> LENGTH: 21
<212> TYPE: PRT
<213> ORGANISM: unknown
<220> FEATURE:
<223> OTHER INFORMATION: synthetic peptide

<400> SEQUENCE: 31

Lys Arg Lys Lys Arg Lys Lys Arg Lys Arg Ser Lys Arg Lys Lys Arg
1 5 10 15

Lys Lys Arg Lys Lys
20

<210> SEQ ID NO 32
<211> LENGTH: 21
<212> TYPE: PRT
<213> ORGANISM: unknown
<220> FEATURE:
<223> OTHER INFORMATION: synthetic peptide

<400> SEQUENCE: 32

Lys Arg Lys Lys Arg Lys Lys Arg Lys Lys Arg Lys Lys Arg Lys Lys
1 5 10 15

Arg Lys Lys Arg Lys
20

<210> SEQ ID NO 33
<211> LENGTH: 22
<212> TYPE: PRT
<213> ORGANISM: unknown
<220> FEATURE:
<223> OTHER INFORMATION: synthetic peptide

<400> SEQUENCE: 33

Lys Arg Lys Lys Arg Lys Lys Arg Lys Arg Gly Ser Gly Lys Arg Lys
1 5 10 15

Lys Arg Lys Lys Arg Lys
20

<210> SEQ ID NO 34
<211> LENGTH: 24
<212> TYPE: PRT
<213> ORGANISM: unknown
<220> FEATURE:
<223> OTHER INFORMATION: synthetic peptide

<400> SEQUENCE: 34

Lys Arg Lys Lys Arg Lys Lys Arg Lys Arg Gly Ser Gly Ser Gly Lys
1 5 10 15

Arg Lys Lys Arg Lys Lys Arg Lys

20

<210> SEQ ID NO 35
<211> LENGTH: 25
<212> TYPE: PRT
<213> ORGANISM: unknown
<220> FEATURE:
<223> OTHER INFORMATION: synthetic peptide

<400> SEQUENCE: 35

```
Lys Arg Lys Lys Arg Lys Lys Arg Lys Lys Arg Lys Lys Arg Lys Lys
1               5                   10                  15

Arg Lys Lys Arg Lys Lys Arg Lys Lys
            20                  25
```

<210> SEQ ID NO 36
<211> LENGTH: 31
<212> TYPE: PRT
<213> ORGANISM: unknown
<220> FEATURE:
<223> OTHER INFORMATION: synthetic peptide

<400> SEQUENCE: 36

```
Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
            20                  25                  30
```

<210> SEQ ID NO 37
<211> LENGTH: 38
<212> TYPE: PRT
<213> ORGANISM: unknown
<220> FEATURE:
<223> OTHER INFORMATION: synthetic peptide

<400> SEQUENCE: 37

```
Lys Arg Lys Lys Arg Lys Lys Arg Lys Arg Gly Ser Gly Ser Gly Lys
1               5                   10                  15

Arg Lys Lys Arg Lys Lys Arg Lys Gly Ser Gly Ser Gly Lys Arg Lys
            20                  25                  30

Lys Arg Lys Lys Arg Lys
        35
```

<210> SEQ ID NO 38
<211> LENGTH: 39
<212> TYPE: PRT
<213> ORGANISM: unknown
<220> FEATURE:
<223> OTHER INFORMATION: synthetic peptide

<400> SEQUENCE: 38

```
Lys Arg Lys Lys Arg Lys Lys Arg Lys Lys Arg Lys Lys Arg Lys Lys
1               5                   10                  15

Arg Lys Lys Arg Lys Lys Arg Lys Lys Arg Lys Lys Arg Lys Lys Arg
            20                  25                  30

Lys Lys Arg Lys Lys Arg Lys
        35
```

<210> SEQ ID NO 39
<211> LENGTH: 42
<212> TYPE: PRT
<213> ORGANISM: unknown
<220> FEATURE:
<223> OTHER INFORMATION: synthetic peptide

<400> SEQUENCE: 39

Lys Arg Lys Lys Arg Lys Lys Arg Lys Arg Ser Lys Arg Lys Lys Arg
1 5 10 15

Lys Lys Arg Lys Arg Ser Lys Arg Lys Lys Arg Lys Lys Arg Lys Arg
20 25 30

Ser Lys Arg Lys Lys Arg Lys Lys Arg Lys
35 40

<210> SEQ ID NO 40
<211> LENGTH: 5
<212> TYPE: PRT
<213> ORGANISM: unknown
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: wherein Xaa is any other amino acid residue than lysine, arginine and histidine

<400> SEQUENCE: 40

Lys Arg Xaa Lys Arg
1 5

<210> SEQ ID NO 41
<211> LENGTH: 5
<212> TYPE: PRT
<213> ORGANISM: unknown
<220> FEATURE:
<223> OTHER INFORMATION: synthetic peptide

<400> SEQUENCE: 41

Lys Arg Ser Lys Arg
1 5

<210> SEQ ID NO 42
<211> LENGTH: 5
<212> TYPE: PRT
<213> ORGANISM: unknown
<220> FEATURE:
<223> OTHER INFORMATION: synthetic peptide

<400> SEQUENCE: 42

Lys Arg Gly Ser Gly
1 5

<210> SEQ ID NO 43
<211> LENGTH: 339
<212> TYPE: PRT
<213> ORGANISM: unknown
<220> FEATURE:
<223> OTHER INFORMATION: PKOBPgpLYS

<400> SEQUENCE: 43

Met Gly Ser Lys Arg Lys Lys Arg Lys Lys Arg Lys Lys Asn Ser Glu
1 5 10 15

Lys Asn Ala Ser Ile Ile Met Ser Ile Gln Arg Thr Leu Ala Ser Leu
20 25 30

Ser Leu Tyr Gly Gly Arg Ile Asp Gly Leu Phe Gly Glu Lys Cys Arg
35 40 45

Gly Ala Ile Ile Leu Met Leu Asn Lys Val Tyr Pro Asn Phe Ser Thr
50 55 60

Asn Lys Leu Pro Ser Asn Thr Tyr Glu Ala Glu Ser Val Phe Thr Phe

```
65                  70                  75                  80

Leu Gln Thr Ala Leu Ala Gly Val Gly Leu Tyr Thr Ile Thr Ile Asp
                85                  90                  95

Gly Lys Trp Gly Gly Thr Ser Gln Gly Ala Ile Asp Ala Leu Val Lys
            100                 105                 110

Ser Tyr Arg Gln Ile Thr Glu Ala Glu Arg Ala Gly Ser Thr Leu Pro
        115                 120                 125

Leu Gly Leu Ala Thr Val Met Ser Lys His Met Ser Ile Glu Gln Leu
    130                 135                 140

Arg Ala Met Leu Pro Thr Asp Arg Gln Gly Tyr Ala Glu Val Tyr Ile
145                 150                 155                 160

Asp Pro Leu Asn Glu Thr Met Asp Ile Phe Glu Ile Asn Thr Pro Leu
                165                 170                 175

Arg Ile Ala His Phe Met Ala Gln Ile Leu His Glu Thr Ala Cys Phe
            180                 185                 190

Lys Tyr Thr Glu Glu Leu Ala Ser Gly Lys Ala Tyr Glu Gly Arg Ala
        195                 200                 205

Asp Leu Gly Asn Thr Arg Pro Gly Asp Gly Pro Leu Phe Lys Gly Arg
    210                 215                 220

Gly Leu Leu Gln Ile Thr Gly Arg Leu Asn Tyr Val Lys Cys Gln Val
225                 230                 235                 240

Tyr Leu Arg Glu Lys Leu Lys Asp Pro Thr Phe Asp Ile Thr Ser Ser
                245                 250                 255

Val Thr Cys Ala Gln Gln Leu Ser Glu Ser Pro Leu Leu Ala Ala Leu
            260                 265                 270

Ala Ser Gly Tyr Phe Trp Arg Phe Ile Lys Pro Lys Leu Asn Glu Thr
        275                 280                 285

Ala Asp Lys Asp Asp Ile Tyr Trp Val Ser Val Tyr Val Asn Gly Tyr
    290                 295                 300

Ala Lys Gln Ala Asn Pro Tyr Tyr Pro Asn Arg Asp Lys Glu Pro Asn
305                 310                 315                 320

His Met Lys Glu Arg Val Gln Met Leu Ala Val Thr Lys Lys Ala Leu
                325                 330                 335

Gly Ile Val
```

<210> SEQ ID NO 44
<211> LENGTH: 21
<212> TYPE: DNA
<213> ORGANISM: Artificial Sequence
<220> FEATURE:
<223> OTHER INFORMATION: OBPgpLYS forward primer

<400> SEQUENCE: 44
atgaaaaata gcgagaagaa t 21

<210> SEQ ID NO 45
<211> LENGTH: 24
<212> TYPE: DNA
<213> ORGANISM: Artificial Sequence
<220> FEATURE:
<223> OTHER INFORMATION: OBPgpLYS reverse primer

<400> SEQUENCE: 45
aactattccg agtgctttct ttgt 24

<210> SEQ ID NO 46
<211> LENGTH: 54

<212> TYPE: DNA
<213> ORGANISM: Artificial Sequence
<220> FEATURE:
<223> OTHER INFORMATION: PKOBPgpLYS forward primer

<400> SEQUENCE: 46
atgggatcca aacgcaagaa acgtaagaaa cgcaaaaaaa atagcgagaa gaat 54

<210> SEQ ID NO 47
<211> LENGTH: 336
<212> TYPE: PRT
<213> ORGANISM: unknown
<220> FEATURE:
<223> OTHER INFORMATION: OBPgpLYS with His-tag

<400> SEQUENCE: 47

Met Lys Asn Ser Glu Lys Asn Ala Ser Ile Ile Met Ser Ile Gln Arg
1 5 10 15

Thr Leu Ala Ser Leu Ser Leu Tyr Gly Gly Arg Ile Asp Gly Leu Phe
20 25 30

Gly Glu Lys Cys Arg Gly Ala Ile Ile Leu Met Leu Asn Lys Val Tyr
35 40 45

Pro Asn Phe Ser Thr Asn Lys Leu Pro Ser Asn Thr Tyr Glu Ala Glu
50 55 60

Ser Val Phe Thr Phe Leu Gln Thr Ala Leu Ala Gly Val Gly Leu Tyr
65 70 75 80

Thr Ile Thr Ile Asp Gly Lys Trp Gly Gly Thr Ser Gln Gly Ala Ile
85 90 95

Asp Ala Leu Val Lys Ser Tyr Arg Gln Ile Thr Glu Ala Glu Arg Ala
100 105 110

Gly Ser Thr Leu Pro Leu Gly Leu Ala Thr Val Met Ser Lys His Met
115 120 125

Ser Ile Glu Gln Leu Arg Ala Met Leu Pro Thr Asp Arg Gln Gly Tyr
130 135 140

Ala Glu Val Tyr Ile Asp Pro Leu Asn Glu Thr Met Asp Ile Phe Glu
145 150 155 160

Ile Asn Thr Pro Leu Arg Ile Ala His Phe Met Ala Gln Ile Leu His
165 170 175

Glu Thr Ala Cys Phe Lys Tyr Thr Glu Glu Leu Ala Ser Gly Lys Ala
180 185 190

Tyr Glu Gly Arg Ala Asp Leu Gly Asn Thr Arg Pro Gly Asp Gly Pro
195 200 205

Leu Phe Lys Gly Arg Gly Leu Leu Gln Ile Thr Gly Arg Leu Asn Tyr
210 215 220

Val Lys Cys Gln Val Tyr Leu Arg Glu Lys Leu Lys Asp Pro Thr Phe
225 230 235 240

Asp Ile Thr Ser Ser Val Thr Cys Ala Gln Gln Leu Ser Glu Ser Pro
245 250 255

Leu Leu Ala Ala Leu Ala Ser Gly Tyr Phe Trp Arg Phe Ile Lys Pro
260 265 270

Lys Leu Asn Glu Thr Ala Asp Lys Asp Asp Ile Tyr Trp Val Ser Val
275 280 285

Tyr Val Asn Gly Tyr Ala Lys Gln Ala Asn Pro Tyr Tyr Pro Asn Arg
290 295 300

Asp Lys Glu Pro Asn His Met Lys Glu Arg Val Gln Met Leu Ala Val
305 310 315 320

-continued

```
Thr Lys Lys Ala Leu Gly Ile Val Lys Gly His His His His His His
                325                 330                 335


<210> SEQ ID NO 48
<211> LENGTH: 1011
<212> TYPE: DNA
<213> ORGANISM: unknown
<220> FEATURE:
<223> OTHER INFORMATION: OBPgpLYS with additional His-tag

<400> SEQUENCE: 48

atgaaaaata gcgagaagaa tgcatcgata attatgtcga tacagagaac gctcgcttca      60

ctctcactct atggaggccg catcgacggc ctctttggag agaagtgtcg tggggctatc     120

atcttgatgc tgaataaggt ctatcctaat ttcagcacca acaaacttcc gagtaacaca     180

tatgaagcgg aatccgtgtt cacgtttctc cagactgctt tggctggtgt tggtctttat     240

accattacta ttgatggtaa atggggtggt acttctcaag gtgctattga cgccctcgtc     300

aagtcttacc gtcaaattac cgaagcggag cgagctgggt cgacgttgcc attaggtctt     360

gctactgtga tgtctaagca tatgtctatt gaacagttga gagcaatgct ccctaccgat     420

agacaaggat atgctgaagt ttatatcgat cctttaaatg agacgatgga tatatttgaa     480

ataaatactc cattacgaat tgctcatttc atggcccaaa tcctccacga aacggcgtgt     540

tttaaatata ccgaagaact ggcgagcggt aaggcttatg agggtcgtgc tgatttaggt     600

aatactcgac caggtgatgg accactgttt aaaggtcgtg gattattaca aattaccggg     660

cgactgaatt atgtgaaatg ccaagtgtat ttgagagaga agttaaagga ccctactttc     720

gacattacgt cgtctgtaac ttgtgcccaa cagctctccg aaagtccact tcttgctgca     780

ttggcatcgg gctacttctg gagattcatc aaacctaaac tcaatgaaac ggctgataaa     840

gacgatatct attgggtttc tgtttatgtc aatggttacg ctaaacaagc gaatccttat     900

taccctaacc gggataagga acccaaccat atgaaagaac gtgtccaaat gcttgcagtg     960

acaaagaaag cactcggaat agttaagggt catcatcacc atcaccattg a             1011


<210> SEQ ID NO 49
<211> LENGTH: 347
<212> TYPE: PRT
<213> ORGANISM: unknown
<220> FEATURE:
<223> OTHER INFORMATION: PKOBPgpLYS with additional His-tag

<400> SEQUENCE: 49

Met Gly Ser Lys Arg Lys Lys Arg Lys Lys Arg Lys Lys Asn Ser Glu
1               5                   10                  15

Lys Asn Ala Ser Ile Ile Met Ser Ile Gln Arg Thr Leu Ala Ser Leu
            20                  25                  30

Ser Leu Tyr Gly Gly Arg Ile Asp Gly Leu Phe Gly Glu Lys Cys Arg
        35                  40                  45

Gly Ala Ile Ile Leu Met Leu Asn Lys Val Tyr Pro Asn Phe Ser Thr
    50                  55                  60

Asn Lys Leu Pro Ser Asn Thr Tyr Glu Ala Glu Ser Val Phe Thr Phe
65                  70                  75                  80

Leu Gln Thr Ala Leu Ala Gly Val Gly Leu Tyr Thr Ile Thr Ile Asp
                85                  90                  95

Gly Lys Trp Gly Gly Thr Ser Gln Gly Ala Ile Asp Ala Leu Val Lys
            100                 105                 110

Ser Tyr Arg Gln Ile Thr Glu Ala Glu Arg Ala Gly Ser Thr Leu Pro
```

```
        115                 120                 125

Leu Gly Leu Ala Thr Val Met Ser Lys His Met Ser Ile Glu Gln Leu
    130                 135                 140

Arg Ala Met Leu Pro Thr Asp Arg Gln Gly Tyr Ala Glu Val Tyr Ile
145                 150                 155                 160

Asp Pro Leu Asn Glu Thr Met Asp Ile Phe Glu Ile Asn Thr Pro Leu
                165                 170                 175

Arg Ile Ala His Phe Met Ala Gln Ile Leu His Glu Thr Ala Cys Phe
            180                 185                 190

Lys Tyr Thr Glu Glu Leu Ala Ser Gly Lys Ala Tyr Glu Gly Arg Ala
        195                 200                 205

Asp Leu Gly Asn Thr Arg Pro Gly Asp Gly Pro Leu Phe Lys Gly Arg
    210                 215                 220

Gly Leu Leu Gln Ile Thr Gly Arg Leu Asn Tyr Val Lys Cys Gln Val
225                 230                 235                 240

Tyr Leu Arg Glu Lys Leu Lys Asp Pro Thr Phe Asp Ile Thr Ser Ser
                245                 250                 255

Val Thr Cys Ala Gln Gln Leu Ser Glu Ser Pro Leu Leu Ala Ala Leu
            260                 265                 270

Ala Ser Gly Tyr Phe Trp Arg Phe Ile Lys Pro Lys Leu Asn Glu Thr
        275                 280                 285

Ala Asp Lys Asp Asp Ile Tyr Trp Val Ser Val Tyr Val Asn Gly Tyr
    290                 295                 300

Ala Lys Gln Ala Asn Pro Tyr Tyr Pro Asn Arg Asp Lys Glu Pro Asn
305                 310                 315                 320

His Met Lys Glu Arg Val Gln Met Leu Ala Val Thr Lys Lys Ala Leu
                325                 330                 335

Gly Ile Val Lys Gly His His His His His His
            340                 345
```

<210> SEQ ID NO 50
<211> LENGTH: 24
<212> TYPE: PRT
<213> ORGANISM: unknown
<220> FEATURE:
<223> OTHER INFORMATION: antimicrobial peptide ascaphine

<400> SEQUENCE: 50

```
Gly Ile Lys Asp Trp Ile Lys Gly Ala Ala Lys Lys Leu Ile Lys Thr
1               5                   10                  15

Val Ala Ser His Ile Ala Asn Gln
            20
```

<210> SEQ ID NO 51
<211> LENGTH: 17
<212> TYPE: PRT
<213> ORGANISM: unknown
<220> FEATURE:
<223> OTHER INFORMATION: antimicrobial peptide apidaecine

<400> SEQUENCE: 51

```
Ala Asn Arg Pro Val Tyr Ile Pro Pro Pro Arg Pro Pro His Pro Arg
1               5                   10                  15

Leu
```

<210> SEQ ID NO 52
<211> LENGTH: 22
<212> TYPE: PRT

<213> ORGANISM: unknown
<220> FEATURE:
<223> OTHER INFORMATION: antimicrobial peptide Nigrocine

<400> SEQUENCE: 52

Gly Leu Leu Ser Lys Val Leu Gly Val Gly Lys Lys Val Leu Cys Gly
1 5 10 15

Val Ser Gly Leu Val Cys
20

<210> SEQ ID NO 53
<211> LENGTH: 24
<212> TYPE: PRT
<213> ORGANISM: unknown
<220> FEATURE:
<223> OTHER INFORMATION: antimicrobial peptide Pseudin

<400> SEQUENCE: 53

Gly Leu Asn Thr Leu Lys Lys Val Phe Gln Gly Leu His Glu Ala Ile
1 5 10 15

Lys Leu Ile Asn Asn His Val Gln
20

<210> SEQ ID NO 54
<211> LENGTH: 354
<212> TYPE: PRT
<213> ORGANISM: unknown
<220> FEATURE:
<223> OTHER INFORMATION: Ascaphine5-OBPgpLYS

<400> SEQUENCE: 54

Met Gly Ile Lys Asp Trp Ile Lys Gly Ala Ala Lys Lys Leu Ile Lys
1 5 10 15

Thr Val Ala Ser His Ile Ala Asn Gln Gly Ser Lys Asn Ser Glu Lys
20 25 30

Asn Ala Ser Ile Ile Met Ser Ile Gln Arg Thr Leu Ala Ser Leu Ser
35 40 45

Leu Tyr Gly Gly Arg Ile Asp Gly Leu Phe Gly Glu Lys Cys Arg Gly
50 55 60

Ala Ile Ile Leu Met Leu Asn Lys Val Tyr Pro Asn Phe Ser Thr Asn
65 70 75 80

Lys Leu Pro Ser Asn Thr Tyr Glu Ala Glu Ser Val Phe Thr Phe Leu
85 90 95

Gln Thr Ala Leu Ala Gly Val Gly Leu Tyr Thr Ile Thr Ile Asp Gly
100 105 110

Lys Trp Gly Gly Thr Ser Gln Gly Ala Ile Asp Ala Leu Val Lys Ser
115 120 125

Tyr Arg Gln Ile Thr Glu Ala Glu Arg Ala Gly Ser Thr Leu Pro Leu
130 135 140

Gly Leu Ala Thr Val Met Ser Lys His Met Ser Ile Glu Gln Leu Arg
145 150 155 160

Ala Met Leu Pro Thr Asp Arg Gln Gly Tyr Ala Glu Val Tyr Ile Asp
165 170 175

Pro Leu Asn Glu Thr Met Asp Ile Phe Glu Ile Asn Thr Pro Leu Arg
180 185 190

Ile Ala His Phe Met Ala Gln Ile Leu His Glu Thr Ala Cys Phe Lys
195 200 205

Tyr Thr Glu Glu Leu Ala Ser Gly Lys Ala Tyr Glu Gly Arg Ala Asp
210 215 220

Leu Gly Asn Thr Arg Pro Gly Asp Gly Pro Leu Phe Lys Gly Arg Gly
225 230 235 240

Leu Leu Gln Ile Thr Gly Arg Leu Asn Tyr Val Lys Cys Gln Val Tyr
245 250 255

Leu Arg Glu Lys Leu Lys Asp Pro Thr Phe Asp Ile Thr Ser Ser Val
260 265 270

Thr Cys Ala Gln Gln Leu Ser Glu Ser Pro Leu Leu Ala Ala Leu Ala
275 280 285

Ser Gly Tyr Phe Trp Arg Phe Ile Lys Pro Lys Leu Asn Glu Thr Ala
290 295 300

Asp Lys Asp Asp Ile Tyr Trp Val Ser Val Tyr Val Asn Gly Tyr Ala
305 310 315 320

Lys Gln Ala Asn Pro Tyr Tyr Pro Asn Arg Asp Lys Glu Pro Asn His
325 330 335

Met Lys Glu Arg Val Gln Met Leu Ala Val Thr Lys Lys Ala His Gly
340 345 350

Ile Val

<210> SEQ ID NO 55
<211> LENGTH: 362
<212> TYPE: PRT
<213> ORGANISM: unknown
<220> FEATURE:
<223> OTHER INFORMATION: Ascaphine5-OBPgpLYS with additional His-tag

<400> SEQUENCE: 55

Met Gly Ile Lys Asp Trp Ile Lys Gly Ala Ala Lys Lys Leu Ile Lys
1 5 10 15

Thr Val Ala Ser His Ile Ala Asn Gln Gly Ser Lys Asn Ser Glu Lys
20 25 30

Asn Ala Ser Ile Ile Met Ser Ile Gln Arg Thr Leu Ala Ser Leu Ser
35 40 45

Leu Tyr Gly Gly Arg Ile Asp Gly Leu Phe Gly Glu Lys Cys Arg Gly
50 55 60

Ala Ile Ile Leu Met Leu Asn Lys Val Tyr Pro Asn Phe Ser Thr Asn
65 70 75 80

Lys Leu Pro Ser Asn Thr Tyr Glu Ala Glu Ser Val Phe Thr Phe Leu
85 90 95

Gln Thr Ala Leu Ala Gly Val Gly Leu Tyr Thr Ile Thr Ile Asp Gly
100 105 110

Lys Trp Gly Gly Thr Ser Gln Gly Ala Ile Asp Ala Leu Val Lys Ser
115 120 125

Tyr Arg Gln Ile Thr Glu Ala Glu Arg Ala Gly Ser Thr Leu Pro Leu
130 135 140

Gly Leu Ala Thr Val Met Ser Lys His Met Ser Ile Glu Gln Leu Arg
145 150 155 160

Ala Met Leu Pro Thr Asp Arg Gln Gly Tyr Ala Glu Val Tyr Ile Asp
165 170 175

Pro Leu Asn Glu Thr Met Asp Ile Phe Glu Ile Asn Thr Pro Leu Arg
180 185 190

Ile Ala His Phe Met Ala Gln Ile Leu His Glu Thr Ala Cys Phe Lys
195 200 205

Tyr Thr Glu Glu Leu Ala Ser Gly Lys Ala Tyr Glu Gly Arg Ala Asp
210 215 220

```
Leu Gly Asn Thr Arg Pro Gly Asp Gly Pro Leu Phe Lys Gly Arg Gly
225                 230                 235                 240

Leu Leu Gln Ile Thr Gly Arg Leu Asn Tyr Val Lys Cys Gln Val Tyr
                245                 250                 255

Leu Arg Glu Lys Leu Lys Asp Pro Thr Phe Asp Ile Thr Ser Ser Val
            260                 265                 270

Thr Cys Ala Gln Gln Leu Ser Glu Ser Pro Leu Leu Ala Ala Leu Ala
        275                 280                 285

Ser Gly Tyr Phe Trp Arg Phe Ile Lys Pro Lys Leu Asn Glu Thr Ala
    290                 295                 300

Asp Lys Asp Asp Ile Tyr Trp Val Ser Val Tyr Val Asn Gly Tyr Ala
305                 310                 315                 320

Lys Gln Ala Asn Pro Tyr Tyr Pro Asn Arg Asp Lys Glu Pro Asn His
                325                 330                 335

Met Lys Glu Arg Val Gln Met Leu Ala Val Thr Lys Lys Ala His Gly
            340                 345                 350

Ile Val Leu Glu His His His His His His
        355                 360


<210> SEQ ID NO 56
<211> LENGTH: 347
<212> TYPE: PRT
<213> ORGANISM: unknown
<220> FEATURE:
<223> OTHER INFORMATION: Apidaecine-OBPgpLYS

<400> SEQUENCE: 56

Met Ala Asn Arg Pro Val Tyr Ile Pro Pro Pro Arg Pro Pro His Pro
1               5                   10                  15

Arg Leu Gly Ser Lys Asn Ser Glu Lys Asn Ala Ser Ile Ile Met Ser
            20                  25                  30

Ile Gln Arg Thr Leu Ala Ser Leu Ser Leu Tyr Gly Gly Arg Ile Asp
        35                  40                  45

Gly Leu Phe Gly Glu Lys Cys Arg Gly Ala Ile Ile Leu Met Leu Asn
    50                  55                  60

Lys Val Tyr Pro Asn Phe Ser Thr Asn Lys Leu Pro Ser Asn Thr Tyr
65                  70                  75                  80

Glu Ala Glu Ser Val Phe Thr Phe Leu Gln Thr Ala Leu Ala Gly Val
                85                  90                  95

Gly Leu Tyr Thr Ile Thr Ile Asp Gly Lys Trp Gly Gly Thr Ser Gln
            100                 105                 110

Gly Ala Ile Asp Ala Leu Val Lys Ser Tyr Arg Gln Ile Thr Glu Ala
        115                 120                 125

Glu Arg Ala Gly Ser Thr Leu Pro Leu Gly Leu Ala Thr Val Met Ser
    130                 135                 140

Lys His Met Ser Ile Glu Gln Leu Arg Ala Met Leu Pro Thr Asp Arg
145                 150                 155                 160

Gln Gly Tyr Ala Glu Val Tyr Ile Asp Pro Leu Asn Glu Thr Met Asp
                165                 170                 175

Ile Phe Glu Ile Asn Thr Pro Leu Arg Ile Ala His Phe Met Ala Gln
            180                 185                 190

Ile Leu His Glu Thr Ala Cys Phe Lys Tyr Thr Glu Glu Leu Ala Ser
        195                 200                 205

Gly Lys Ala Tyr Glu Gly Arg Ala Asp Leu Gly Asn Thr Arg Pro Gly
    210                 215                 220
```

```
Asp Gly Pro Leu Phe Lys Gly Arg Gly Leu Leu Gln Ile Thr Gly Arg
225                 230                 235                 240

Leu Asn Tyr Val Lys Cys Gln Val Tyr Leu Arg Glu Lys Leu Lys Asp
                245                 250                 255

Pro Thr Phe Asp Ile Thr Ser Ser Val Thr Cys Ala Gln Gln Leu Ser
            260                 265                 270

Glu Ser Pro Leu Leu Ala Ala Leu Ala Ser Gly Tyr Phe Trp Arg Phe
        275                 280                 285

Ile Lys Pro Lys Leu Asn Glu Thr Ala Asp Lys Asp Asp Ile Tyr Trp
    290                 295                 300

Val Ser Val Tyr Val Asn Gly Tyr Ala Lys Gln Ala Asn Pro Tyr Tyr
305                 310                 315                 320

Pro Asn Arg Asp Lys Glu Pro Asn His Met Lys Glu Arg Val Gln Met
                325                 330                 335

Leu Ala Val Thr Lys Lys Ala His Gly Ile Val
            340                 345


<210> SEQ ID NO 57
<211> LENGTH: 355
<212> TYPE: PRT
<213> ORGANISM: unknown
<220> FEATURE:
<223> OTHER INFORMATION: Apidaecine-OBPgpLYS with additional His-tag

<400> SEQUENCE: 57

Met Ala Asn Arg Pro Val Tyr Ile Pro Pro Pro Arg Pro Pro His Pro
1               5                   10                  15

Arg Leu Gly Ser Lys Asn Ser Glu Lys Asn Ala Ser Ile Ile Met Ser
            20                  25                  30

Ile Gln Arg Thr Leu Ala Ser Leu Ser Leu Tyr Gly Gly Arg Ile Asp
        35                  40                  45

Gly Leu Phe Gly Glu Lys Cys Arg Gly Ala Ile Ile Leu Met Leu Asn
    50                  55                  60

Lys Val Tyr Pro Asn Phe Ser Thr Asn Lys Leu Pro Ser Asn Thr Tyr
65                  70                  75                  80

Glu Ala Glu Ser Val Phe Thr Phe Leu Gln Thr Ala Leu Ala Gly Val
                85                  90                  95

Gly Leu Tyr Thr Ile Thr Ile Asp Gly Lys Trp Gly Gly Thr Ser Gln
            100                 105                 110

Gly Ala Ile Asp Ala Leu Val Lys Ser Tyr Arg Gln Ile Thr Glu Ala
        115                 120                 125

Glu Arg Ala Gly Ser Thr Leu Pro Leu Gly Leu Ala Thr Val Met Ser
    130                 135                 140

Lys His Met Ser Ile Glu Gln Leu Arg Ala Met Leu Pro Thr Asp Arg
145                 150                 155                 160

Gln Gly Tyr Ala Glu Val Tyr Ile Asp Pro Leu Asn Glu Thr Met Asp
                165                 170                 175

Ile Phe Glu Ile Asn Thr Pro Leu Arg Ile Ala His Phe Met Ala Gln
            180                 185                 190

Ile Leu His Glu Thr Ala Cys Phe Lys Tyr Thr Glu Glu Leu Ala Ser
        195                 200                 205

Gly Lys Ala Tyr Glu Gly Arg Ala Asp Leu Gly Asn Thr Arg Pro Gly
    210                 215                 220

Asp Gly Pro Leu Phe Lys Gly Arg Gly Leu Leu Gln Ile Thr Gly Arg
225                 230                 235                 240
```

```
Leu Asn Tyr Val Lys Cys Gln Val Tyr Leu Arg Glu Lys Leu Lys Asp
                245                 250                 255

Pro Thr Phe Asp Ile Thr Ser Ser Val Thr Cys Ala Gln Gln Leu Ser
            260                 265                 270

Glu Ser Pro Leu Leu Ala Ala Leu Ala Ser Gly Tyr Phe Trp Arg Phe
        275                 280                 285

Ile Lys Pro Lys Leu Asn Glu Thr Ala Asp Lys Asp Asp Ile Tyr Trp
    290                 295                 300

Val Ser Val Tyr Val Asn Gly Tyr Ala Lys Gln Ala Asn Pro Tyr Tyr
305                 310                 315                 320

Pro Asn Arg Asp Lys Glu Pro Asn His Met Lys Glu Arg Val Gln Met
                325                 330                 335

Leu Ala Val Thr Lys Lys Ala His Gly Ile Val Leu Glu His His His
            340                 345                 350

His His His
        355


<210> SEQ ID NO 58
<211> LENGTH: 352
<212> TYPE: PRT
<213> ORGANISM: unknown
<220> FEATURE:
<223> OTHER INFORMATION: Nigrocine 2-OBPgpLYS

<400> SEQUENCE: 58

Met Gly Leu Leu Ser Lys Val Leu Gly Val Gly Lys Lys Val Leu Cys
1               5                   10                  15

Gly Val Ser Gly Leu Val Cys Gly Ser Lys Asn Ser Glu Lys Asn Ala
            20                  25                  30

Ser Ile Ile Met Ser Ile Gln Arg Thr Leu Ala Ser Leu Ser Leu Tyr
        35                  40                  45

Gly Gly Arg Ile Asp Gly Leu Phe Gly Glu Lys Cys Arg Gly Ala Ile
    50                  55                  60

Ile Leu Met Leu Asn Lys Val Tyr Pro Asn Phe Ser Thr Asn Lys Leu
65                  70                  75                  80

Pro Ser Asn Thr Tyr Glu Ala Glu Ser Val Phe Thr Phe Leu Gln Thr
                85                  90                  95

Ala Leu Ala Gly Val Gly Leu Tyr Thr Ile Thr Ile Asp Gly Lys Trp
            100                 105                 110

Gly Gly Thr Ser Gln Gly Ala Ile Asp Ala Leu Val Lys Ser Tyr Arg
        115                 120                 125

Gln Ile Thr Glu Ala Glu Arg Ala Gly Ser Thr Leu Pro Leu Gly Leu
    130                 135                 140

Ala Thr Val Met Ser Lys His Met Ser Ile Glu Gln Leu Arg Ala Met
145                 150                 155                 160

Leu Pro Thr Asp Arg Gln Gly Tyr Ala Glu Val Tyr Ile Asp Pro Leu
                165                 170                 175

Asn Glu Thr Met Asp Ile Phe Glu Ile Asn Thr Pro Leu Arg Ile Ala
            180                 185                 190

His Phe Met Ala Gln Ile Leu His Glu Thr Ala Cys Phe Lys Tyr Thr
        195                 200                 205

Glu Glu Leu Ala Ser Gly Lys Ala Tyr Glu Gly Arg Ala Asp Leu Gly
    210                 215                 220

Asn Thr Arg Pro Gly Asp Gly Pro Leu Phe Lys Gly Arg Gly Leu Leu
225                 230                 235                 240
```

-continued

```
Gln Ile Thr Gly Arg Leu Asn Tyr Val Lys Cys Gln Val Tyr Leu Arg
            245                 250                 255

Glu Lys Leu Lys Asp Pro Thr Phe Asp Ile Thr Ser Ser Val Thr Cys
            260                 265                 270

Ala Gln Gln Leu Ser Glu Ser Pro Leu Leu Ala Ala Leu Ala Ser Gly
        275                 280                 285

Tyr Phe Trp Arg Phe Ile Lys Pro Lys Leu Asn Glu Thr Ala Asp Lys
    290                 295                 300

Asp Asp Ile Tyr Trp Val Ser Val Tyr Val Asn Gly Tyr Ala Lys Gln
305                 310                 315                 320

Ala Asn Pro Tyr Tyr Pro Asn Arg Asp Lys Glu Pro Asn His Met Lys
            325                 330                 335

Glu Arg Val Gln Met Leu Ala Val Thr Lys Lys Ala His Gly Ile Val
            340                 345                 350


<210> SEQ ID NO 59
<211> LENGTH: 360
<212> TYPE: PRT
<213> ORGANISM: unknown
<220> FEATURE:
<223> OTHER INFORMATION: Nigrocine 2-OBPgpLYS with additional His-tag

<400> SEQUENCE: 59

Met Gly Leu Leu Ser Lys Val Leu Gly Val Gly Lys Lys Val Leu Cys
1               5                   10                  15

Gly Val Ser Gly Leu Val Cys Gly Ser Lys Asn Ser Glu Lys Asn Ala
            20                  25                  30

Ser Ile Ile Met Ser Ile Gln Arg Thr Leu Ala Ser Leu Ser Leu Tyr
        35                  40                  45

Gly Gly Arg Ile Asp Gly Leu Phe Gly Glu Lys Cys Arg Gly Ala Ile
    50                  55                  60

Ile Leu Met Leu Asn Lys Val Tyr Pro Asn Phe Ser Thr Asn Lys Leu
65                  70                  75                  80

Pro Ser Asn Thr Tyr Glu Ala Glu Ser Val Phe Thr Phe Leu Gln Thr
                85                  90                  95

Ala Leu Ala Gly Val Gly Leu Tyr Thr Ile Thr Ile Asp Gly Lys Trp
            100                 105                 110

Gly Gly Thr Ser Gln Gly Ala Ile Asp Ala Leu Val Lys Ser Tyr Arg
        115                 120                 125

Gln Ile Thr Glu Ala Glu Arg Ala Gly Ser Thr Leu Pro Leu Gly Leu
    130                 135                 140

Ala Thr Val Met Ser Lys His Met Ser Ile Glu Gln Leu Arg Ala Met
145                 150                 155                 160

Leu Pro Thr Asp Arg Gln Gly Tyr Ala Glu Val Tyr Ile Asp Pro Leu
                165                 170                 175

Asn Glu Thr Met Asp Ile Phe Glu Ile Asn Thr Pro Leu Arg Ile Ala
            180                 185                 190

His Phe Met Ala Gln Ile Leu His Glu Thr Ala Cys Phe Lys Tyr Thr
        195                 200                 205

Glu Glu Leu Ala Ser Gly Lys Ala Tyr Glu Gly Arg Ala Asp Leu Gly
    210                 215                 220

Asn Thr Arg Pro Gly Asp Gly Pro Leu Phe Lys Gly Arg Gly Leu Leu
225                 230                 235                 240

Gln Ile Thr Gly Arg Leu Asn Tyr Val Lys Cys Gln Val Tyr Leu Arg
                245                 250                 255
```

```
Glu Lys Leu Lys Asp Pro Thr Phe Asp Ile Thr Ser Ser Val Thr Cys
            260                 265                 270

Ala Gln Gln Leu Ser Glu Ser Pro Leu Leu Ala Ala Leu Ala Ser Gly
        275                 280                 285

Tyr Phe Trp Arg Phe Ile Lys Pro Lys Leu Asn Glu Thr Ala Asp Lys
    290                 295                 300

Asp Asp Ile Tyr Trp Val Ser Val Tyr Val Asn Gly Tyr Ala Lys Gln
305                 310                 315                 320

Ala Asn Pro Tyr Tyr Pro Asn Arg Asp Lys Glu Pro Asn His Met Lys
                325                 330                 335

Glu Arg Val Gln Met Leu Ala Val Thr Lys Lys Ala His Gly Ile Val
            340                 345                 350

Leu Glu His His His His His His
        355                 360


<210> SEQ ID NO 60
<211> LENGTH: 354
<212> TYPE: PRT
<213> ORGANISM: unknown
<220> FEATURE:
<223> OTHER INFORMATION: Pseudin 1-OBPgpLYS

<400> SEQUENCE: 60

Met Gly Leu Asn Thr Leu Lys Lys Val Phe Gln Gly Leu His Glu Ala
1               5                   10                  15

Ile Lys Leu Ile Asn Asn His Val Gln Gly Ser Lys Asn Ser Glu Lys
            20                  25                  30

Asn Ala Ser Ile Ile Met Ser Ile Gln Arg Thr Leu Ala Ser Leu Ser
        35                  40                  45

Leu Tyr Gly Gly Arg Ile Asp Gly Leu Phe Gly Glu Lys Cys Arg Gly
    50                  55                  60

Ala Ile Ile Leu Met Leu Asn Lys Val Tyr Pro Asn Phe Ser Thr Asn
65                  70                  75                  80

Lys Leu Pro Ser Asn Thr Tyr Glu Ala Glu Ser Val Phe Thr Phe Leu
                85                  90                  95

Gln Thr Ala Leu Ala Gly Val Gly Leu Tyr Thr Ile Thr Ile Asp Gly
            100                 105                 110

Lys Trp Gly Gly Thr Ser Gln Gly Ala Ile Asp Ala Leu Val Lys Ser
        115                 120                 125

Tyr Arg Gln Ile Thr Glu Ala Glu Arg Ala Gly Ser Thr Leu Pro Leu
    130                 135                 140

Gly Leu Ala Thr Val Met Ser Lys His Met Ser Ile Glu Gln Leu Arg
145                 150                 155                 160

Ala Met Leu Pro Thr Asp Arg Gln Gly Tyr Ala Glu Val Tyr Ile Asp
                165                 170                 175

Pro Leu Asn Glu Thr Met Asp Ile Phe Glu Ile Asn Thr Pro Leu Arg
            180                 185                 190

Ile Ala His Phe Met Ala Gln Ile Leu His Glu Thr Ala Cys Phe Lys
        195                 200                 205

Tyr Thr Glu Glu Leu Ala Ser Gly Lys Ala Tyr Glu Gly Arg Ala Asp
    210                 215                 220

Leu Gly Asn Thr Arg Pro Gly Asp Gly Pro Leu Phe Lys Gly Arg Gly
225                 230                 235                 240

Leu Leu Gln Ile Thr Gly Arg Leu Asn Tyr Val Lys Cys Gln Val Tyr
                245                 250                 255
```

```
Leu Arg Glu Lys Leu Lys Asp Pro Thr Phe Asp Ile Thr Ser Ser Val
            260                 265                 270

Thr Cys Ala Gln Gln Leu Ser Glu Ser Pro Leu Leu Ala Ala Leu Ala
        275                 280                 285

Ser Gly Tyr Phe Trp Arg Phe Ile Lys Pro Lys Leu Asn Glu Thr Ala
    290                 295                 300

Asp Lys Asp Asp Ile Tyr Trp Val Ser Val Tyr Val Asn Gly Tyr Ala
305                 310                 315                 320

Lys Gln Ala Asn Pro Tyr Tyr Pro Asn Arg Asp Lys Glu Pro Asn His
                325                 330                 335

Met Lys Glu Arg Val Gln Met Leu Ala Val Thr Lys Lys Ala His Gly
            340                 345                 350

Ile Val


<210> SEQ ID NO 61
<211> LENGTH: 362
<212> TYPE: PRT
<213> ORGANISM: unknown
<220> FEATURE:
<223> OTHER INFORMATION: Pseudin 1-OBPgpLYS with additional His-tag

<400> SEQUENCE: 61

Met Gly Leu Asn Thr Leu Lys Lys Val Phe Gln Gly Leu His Glu Ala
1               5                   10                  15

Ile Lys Leu Ile Asn Asn His Val Gln Gly Ser Lys Asn Ser Glu Lys
            20                  25                  30

Asn Ala Ser Ile Ile Met Ser Ile Gln Arg Thr Leu Ala Ser Leu Ser
        35                  40                  45

Leu Tyr Gly Gly Arg Ile Asp Gly Leu Phe Gly Glu Lys Cys Arg Gly
    50                  55                  60

Ala Ile Ile Leu Met Leu Asn Lys Val Tyr Pro Asn Phe Ser Thr Asn
65                  70                  75                  80

Lys Leu Pro Ser Asn Thr Tyr Glu Ala Glu Ser Val Phe Thr Phe Leu
                85                  90                  95

Gln Thr Ala Leu Ala Gly Val Gly Leu Tyr Thr Ile Thr Ile Asp Gly
            100                 105                 110

Lys Trp Gly Gly Thr Ser Gln Gly Ala Ile Asp Ala Leu Val Lys Ser
        115                 120                 125

Tyr Arg Gln Ile Thr Glu Ala Glu Arg Ala Gly Ser Thr Leu Pro Leu
    130                 135                 140

Gly Leu Ala Thr Val Met Ser Lys His Met Ser Ile Glu Gln Leu Arg
145                 150                 155                 160

Ala Met Leu Pro Thr Asp Arg Gln Gly Tyr Ala Glu Val Tyr Ile Asp
                165                 170                 175

Pro Leu Asn Glu Thr Met Asp Ile Phe Glu Ile Asn Thr Pro Leu Arg
            180                 185                 190

Ile Ala His Phe Met Ala Gln Ile Leu His Glu Thr Ala Cys Phe Lys
        195                 200                 205

Tyr Thr Glu Glu Leu Ala Ser Gly Lys Ala Tyr Glu Gly Arg Ala Asp
    210                 215                 220

Leu Gly Asn Thr Arg Pro Gly Asp Gly Pro Leu Phe Lys Gly Arg Gly
225                 230                 235                 240

Leu Leu Gln Ile Thr Gly Arg Leu Asn Tyr Val Lys Cys Gln Val Tyr
                245                 250                 255

Leu Arg Glu Lys Leu Lys Asp Pro Thr Phe Asp Ile Thr Ser Ser Val
```

```
            260                 265                 270

Thr Cys Ala Gln Gln Leu Ser Glu Ser Pro Leu Leu Ala Ala Leu Ala
        275                 280                 285

Ser Gly Tyr Phe Trp Arg Phe Ile Lys Pro Lys Leu Asn Glu Thr Ala
    290                 295                 300

Asp Lys Asp Asp Ile Tyr Trp Val Ser Val Tyr Val Asn Gly Tyr Ala
305                 310                 315                 320

Lys Gln Ala Asn Pro Tyr Tyr Pro Asn Arg Asp Lys Glu Pro Asn His
                325                 330                 335

Met Lys Glu Arg Val Gln Met Leu Ala Val Thr Lys Lys Ala His Gly
            340                 345                 350

Ile Val Leu Glu His His His His His His
        355                 360


<210> SEQ ID NO 62
<211> LENGTH: 369
<212> TYPE: PRT
<213> ORGANISM: unknown
<220> FEATURE:
<223> OTHER INFORMATION: Sarcotoxin IA-OBPgpLYS

<400> SEQUENCE: 62

Met Gly Trp Leu Lys Lys Ile Gly Lys Lys Ile Glu Arg Val Gly Gln
1               5                   10                  15

His Thr Arg Asp Ala Thr Ile Gln Gly Leu Gly Ile Ala Gln Gln Ala
            20                  25                  30

Ala Asn Val Ala Ala Thr Ala Arg Gly Ser Lys Asn Ser Glu Lys Asn
        35                  40                  45

Ala Ser Ile Ile Met Ser Ile Gln Arg Thr Leu Ala Ser Leu Ser Leu
    50                  55                  60

Tyr Gly Gly Arg Ile Asp Gly Leu Phe Gly Glu Lys Cys Arg Gly Ala
65                  70                  75                  80

Ile Ile Leu Met Leu Asn Lys Val Tyr Pro Asn Phe Ser Thr Asn Lys
                85                  90                  95

Leu Pro Ser Asn Thr Tyr Glu Ala Glu Ser Val Phe Thr Phe Leu Gln
            100                 105                 110

Thr Ala Leu Ala Gly Val Gly Leu Tyr Thr Ile Thr Ile Asp Gly Lys
        115                 120                 125

Trp Gly Gly Thr Ser Gln Gly Ala Ile Asp Ala Leu Val Lys Ser Tyr
    130                 135                 140

Arg Gln Ile Thr Glu Ala Glu Arg Ala Gly Ser Thr Leu Pro Leu Gly
145                 150                 155                 160

Leu Ala Thr Val Met Ser Lys His Met Ser Ile Glu Gln Leu Arg Ala
                165                 170                 175

Met Leu Pro Thr Asp Arg Gln Gly Tyr Ala Glu Val Tyr Ile Asp Pro
            180                 185                 190

Leu Asn Glu Thr Met Asp Ile Phe Glu Ile Asn Thr Pro Leu Arg Ile
        195                 200                 205

Ala His Phe Met Ala Gln Ile Leu His Glu Thr Ala Cys Phe Lys Tyr
    210                 215                 220

Thr Glu Glu Leu Ala Ser Gly Lys Ala Tyr Glu Gly Arg Ala Asp Leu
225                 230                 235                 240

Gly Asn Thr Arg Pro Gly Asp Gly Pro Leu Phe Lys Gly Arg Gly Leu
                245                 250                 255

Leu Gln Ile Thr Gly Arg Leu Asn Tyr Val Lys Cys Gln Val Tyr Leu
```

```
            260                 265                 270

Arg Glu Lys Leu Lys Asp Pro Thr Phe Asp Ile Thr Ser Ser Val Thr
        275                 280                 285

Cys Ala Gln Gln Leu Ser Glu Ser Pro Leu Leu Ala Ala Leu Ala Ser
    290                 295                 300

Gly Tyr Phe Trp Arg Phe Ile Lys Pro Lys Leu Asn Glu Thr Ala Asp
305                 310                 315                 320

Lys Asp Asp Ile Tyr Trp Val Ser Val Tyr Val Asn Gly Tyr Ala Lys
                325                 330                 335

Gln Ala Asn Pro Tyr Tyr Pro Asn Arg Asp Lys Glu Pro Asn His Met
            340                 345                 350

Lys Glu Arg Val Gln Met Leu Ala Val Thr Lys Lys Ala His Gly Ile
        355                 360                 365

Val


<210> SEQ ID NO 63
<211> LENGTH: 377
<212> TYPE: PRT
<213> ORGANISM: unknown
<220> FEATURE:
<223> OTHER INFORMATION: Sarcotoxin IA-OBPgpLYS with additional His-tag

<400> SEQUENCE: 63

Met Gly Trp Leu Lys Lys Ile Gly Lys Lys Ile Glu Arg Val Gly Gln
1               5                   10                  15

His Thr Arg Asp Ala Thr Ile Gln Gly Leu Gly Ile Ala Gln Gln Ala
            20                  25                  30

Ala Asn Val Ala Ala Thr Ala Arg Gly Ser Lys Asn Ser Glu Lys Asn
        35                  40                  45

Ala Ser Ile Ile Met Ser Ile Gln Arg Thr Leu Ala Ser Leu Ser Leu
    50                  55                  60

Tyr Gly Gly Arg Ile Asp Gly Leu Phe Gly Glu Lys Cys Arg Gly Ala
65                  70                  75                  80

Ile Ile Leu Met Leu Asn Lys Val Tyr Pro Asn Phe Ser Thr Asn Lys
                85                  90                  95

Leu Pro Ser Asn Thr Tyr Glu Ala Glu Ser Val Phe Thr Phe Leu Gln
            100                 105                 110

Thr Ala Leu Ala Gly Val Gly Leu Tyr Thr Ile Thr Ile Asp Gly Lys
        115                 120                 125

Trp Gly Gly Thr Ser Gln Gly Ala Ile Asp Ala Leu Val Lys Ser Tyr
    130                 135                 140

Arg Gln Ile Thr Glu Ala Glu Arg Ala Gly Ser Thr Leu Pro Leu Gly
145                 150                 155                 160

Leu Ala Thr Val Met Ser Lys His Met Ser Ile Glu Gln Leu Arg Ala
                165                 170                 175

Met Leu Pro Thr Asp Arg Gln Gly Tyr Ala Glu Val Tyr Ile Asp Pro
            180                 185                 190

Leu Asn Glu Thr Met Asp Ile Phe Glu Ile Asn Thr Pro Leu Arg Ile
        195                 200                 205

Ala His Phe Met Ala Gln Ile Leu His Glu Thr Ala Cys Phe Lys Tyr
    210                 215                 220

Thr Glu Glu Leu Ala Ser Gly Lys Ala Tyr Glu Gly Arg Ala Asp Leu
225                 230                 235                 240

Gly Asn Thr Arg Pro Gly Asp Gly Pro Leu Phe Lys Gly Arg Gly Leu
                245                 250                 255
```

```
Leu Gln Ile Thr Gly Arg Leu Asn Tyr Val Lys Cys Gln Val Tyr Leu
            260                 265                 270

Arg Glu Lys Leu Lys Asp Pro Thr Phe Asp Ile Thr Ser Ser Val Thr
        275                 280                 285

Cys Ala Gln Gln Leu Ser Glu Ser Pro Leu Leu Ala Ala Leu Ala Ser
    290                 295                 300

Gly Tyr Phe Trp Arg Phe Ile Lys Pro Lys Leu Asn Glu Thr Ala Asp
305                 310                 315                 320

Lys Asp Asp Ile Tyr Trp Val Ser Val Tyr Val Asn Gly Tyr Ala Lys
                325                 330                 335

Gln Ala Asn Pro Tyr Tyr Pro Asn Arg Asp Lys Glu Pro Asn His Met
            340                 345                 350

Lys Glu Arg Val Gln Met Leu Ala Val Thr Lys Lys Ala His Gly Ile
        355                 360                 365

Val Leu Glu His His His His His His
    370                 375


<210> SEQ ID NO 64
<211> LENGTH: 359
<212> TYPE: PRT
<213> ORGANISM: unknown
<220> FEATURE:
<223> OTHER INFORMATION: Sarcotoxin IA-OBPgpLYS

<400> SEQUENCE: 64

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Asn Ser Glu Lys Asn Ala Ser Ile Ile Met Ser Ile Gln Arg Thr
        35                  40                  45

Leu Ala Ser Leu Ser Leu Tyr Gly Gly Arg Ile Asp Gly Leu Phe Gly
    50                  55                  60

Glu Lys Cys Arg Gly Ala Ile Ile Leu Met Leu Asn Lys Val Tyr Pro
65                  70                  75                  80

Asn Phe Ser Thr Asn Lys Leu Pro Ser Asn Thr Tyr Glu Ala Glu Ser
                85                  90                  95

Val Phe Thr Phe Leu Gln Thr Ala Leu Ala Gly Val Gly Leu Tyr Thr
            100                 105                 110

Ile Thr Ile Asp Gly Lys Trp Gly Gly Thr Ser Gln Gly Ala Ile Asp
        115                 120                 125

Ala Leu Val Lys Ser Tyr Arg Gln Ile Thr Glu Ala Glu Arg Ala Gly
    130                 135                 140

Ser Thr Leu Pro Leu Gly Leu Ala Thr Val Met Ser Lys His Met Ser
145                 150                 155                 160

Ile Glu Gln Leu Arg Ala Met Leu Pro Thr Asp Arg Gln Gly Tyr Ala
                165                 170                 175

Glu Val Tyr Ile Asp Pro Leu Asn Glu Thr Met Asp Ile Phe Glu Ile
            180                 185                 190

Asn Thr Pro Leu Arg Ile Ala His Phe Met Ala Gln Ile Leu His Glu
        195                 200                 205

Thr Ala Cys Phe Lys Tyr Thr Glu Glu Leu Ala Ser Gly Lys Ala Tyr
    210                 215                 220

Glu Gly Arg Ala Asp Leu Gly Asn Thr Arg Pro Gly Asp Gly Pro Leu
225                 230                 235                 240
```

```
Phe Lys Gly Arg Gly Leu Leu Gln Ile Thr Gly Arg Leu Asn Tyr Val
                245                 250                 255

Lys Cys Gln Val Tyr Leu Arg Glu Lys Leu Lys Asp Pro Thr Phe Asp
            260                 265                 270

Ile Thr Ser Ser Val Thr Cys Ala Gln Gln Leu Ser Glu Ser Pro Leu
        275                 280                 285

Leu Ala Ala Leu Ala Ser Gly Tyr Phe Trp Arg Phe Ile Lys Pro Lys
    290                 295                 300

Leu Asn Glu Thr Ala Asp Lys Asp Asp Ile Tyr Trp Val Ser Val Tyr
305                 310                 315                 320

Val Asn Gly Tyr Ala Lys Gln Ala Asn Pro Tyr Tyr Pro Asn Arg Asp
                325                 330                 335

Lys Glu Pro Asn His Met Lys Glu Arg Val Gln Met Leu Ala Val Thr
            340                 345                 350

Lys Lys Ala His Gly Ile Val
        355


<210> SEQ ID NO 65
<211> LENGTH: 367
<212> TYPE: PRT
<213> ORGANISM: unknown
<220> FEATURE:
<223> OTHER INFORMATION: Sarcotoxin IA-OBPgpLYS with additional His-tag

<400> SEQUENCE: 65

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Asn Ser Glu Lys Asn Ala Ser Ile Ile Met Ser Ile Gln Arg Thr
        35                  40                  45

Leu Ala Ser Leu Ser Leu Tyr Gly Gly Arg Ile Asp Gly Leu Phe Gly
    50                  55                  60

Glu Lys Cys Arg Gly Ala Ile Ile Leu Met Leu Asn Lys Val Tyr Pro
65                  70                  75                  80

Asn Phe Ser Thr Asn Lys Leu Pro Ser Asn Thr Tyr Glu Ala Glu Ser
                85                  90                  95

Val Phe Thr Phe Leu Gln Thr Ala Leu Ala Gly Val Gly Leu Tyr Thr
            100                 105                 110

Ile Thr Ile Asp Gly Lys Trp Gly Gly Thr Ser Gln Gly Ala Ile Asp
        115                 120                 125

Ala Leu Val Lys Ser Tyr Arg Gln Ile Thr Glu Ala Glu Arg Ala Gly
    130                 135                 140

Ser Thr Leu Pro Leu Gly Leu Ala Thr Val Met Ser Lys His Met Ser
145                 150                 155                 160

Ile Glu Gln Leu Arg Ala Met Leu Pro Thr Asp Arg Gln Gly Tyr Ala
                165                 170                 175

Glu Val Tyr Ile Asp Pro Leu Asn Glu Thr Met Asp Ile Phe Glu Ile
            180                 185                 190

Asn Thr Pro Leu Arg Ile Ala His Phe Met Ala Gln Ile Leu His Glu
        195                 200                 205

Thr Ala Cys Phe Lys Tyr Thr Glu Glu Leu Ala Ser Gly Lys Ala Tyr
    210                 215                 220

Glu Gly Arg Ala Asp Leu Gly Asn Thr Arg Pro Gly Asp Gly Pro Leu
225                 230                 235                 240
```

```
Phe Lys Gly Arg Gly Leu Leu Gln Ile Thr Gly Arg Leu Asn Tyr Val
                245                 250                 255

Lys Cys Gln Val Tyr Leu Arg Glu Lys Leu Lys Asp Pro Thr Phe Asp
            260                 265                 270

Ile Thr Ser Ser Val Thr Cys Ala Gln Gln Leu Ser Glu Ser Pro Leu
        275                 280                 285

Leu Ala Ala Leu Ala Ser Gly Tyr Phe Trp Arg Phe Ile Lys Pro Lys
    290                 295                 300

Leu Asn Glu Thr Ala Asp Lys Asp Asp Ile Tyr Trp Val Ser Val Tyr
305                 310                 315                 320

Val Asn Gly Tyr Ala Lys Gln Ala Asn Pro Tyr Tyr Pro Asn Arg Asp
                325                 330                 335

Lys Glu Pro Asn His Met Lys Glu Arg Val Gln Met Leu Ala Val Thr
            340                 345                 350

Lys Lys Ala His Gly Ile Val Leu Glu His His His His His His
        355                 360                 365


<210> SEQ ID NO 66
<211> LENGTH: 366
<212> TYPE: PRT
<213> ORGANISM: unknown
<220> FEATURE:
<223> OTHER INFORMATION: Cecropin A (A.aegypti)-OBPgpLYS

<400> SEQUENCE: 66

Met Gly Gly Leu Lys Lys Leu Gly Lys Lys Leu Glu Gly Ala Gly Lys
1               5                   10                  15

Arg Val Phe Asn Ala Ala Glu Lys Ala Leu Pro Val Val Ala Gly Ala
            20                  25                  30

Lys Ala Leu Arg Lys Gly Ser Lys Asn Ser Glu Lys Asn Ala Ser Ile
        35                  40                  45

Ile Met Ser Ile Gln Arg Thr Leu Ala Ser Leu Ser Leu Tyr Gly Gly
    50                  55                  60

Arg Ile Asp Gly Leu Phe Gly Glu Lys Cys Arg Gly Ala Ile Ile Leu
65                  70                  75                  80

Met Leu Asn Lys Val Tyr Pro Asn Phe Ser Thr Asn Lys Leu Pro Ser
                85                  90                  95

Asn Thr Tyr Glu Ala Glu Ser Val Phe Thr Phe Leu Gln Thr Ala Leu
            100                 105                 110

Ala Gly Val Gly Leu Tyr Thr Ile Thr Ile Asp Gly Lys Trp Gly Gly
        115                 120                 125

Thr Ser Gln Gly Ala Ile Asp Ala Leu Val Lys Ser Tyr Arg Gln Ile
    130                 135                 140

Thr Glu Ala Glu Arg Ala Gly Ser Thr Leu Pro Leu Gly Leu Ala Thr
145                 150                 155                 160

Val Met Ser Lys His Met Ser Ile Glu Gln Leu Arg Ala Met Leu Pro
                165                 170                 175

Thr Asp Arg Gln Gly Tyr Ala Glu Val Tyr Ile Asp Pro Leu Asn Glu
            180                 185                 190

Thr Met Asp Ile Phe Glu Ile Asn Thr Pro Leu Arg Ile Ala His Phe
        195                 200                 205

Met Ala Gln Ile Leu His Glu Thr Ala Cys Phe Lys Tyr Thr Glu Glu
    210                 215                 220

Leu Ala Ser Gly Lys Ala Tyr Glu Gly Arg Ala Asp Leu Gly Asn Thr
225                 230                 235                 240
```

```
Arg Pro Gly Asp Gly Pro Leu Phe Lys Gly Arg Gly Leu Leu Gln Ile
                245                 250                 255

Thr Gly Arg Leu Asn Tyr Val Lys Cys Gln Val Tyr Leu Arg Glu Lys
            260                 265                 270

Leu Lys Asp Pro Thr Phe Asp Ile Thr Ser Ser Val Thr Cys Ala Gln
        275                 280                 285

Gln Leu Ser Glu Ser Pro Leu Leu Ala Ala Leu Ala Ser Gly Tyr Phe
    290                 295                 300

Trp Arg Phe Ile Lys Pro Lys Leu Asn Glu Thr Ala Asp Lys Asp Asp
305                 310                 315                 320

Ile Tyr Trp Val Ser Val Tyr Val Asn Gly Tyr Ala Lys Gln Ala Asn
                325                 330                 335

Pro Tyr Tyr Pro Asn Arg Asp Lys Glu Pro Asn His Met Lys Glu Arg
            340                 345                 350

Val Gln Met Leu Ala Val Thr Lys Lys Ala His Gly Ile Val
        355                 360                 365


<210> SEQ ID NO 67
<211> LENGTH: 374
<212> TYPE: PRT
<213> ORGANISM: unknown
<220> FEATURE:
<223> OTHER INFORMATION: Cecropin A (A.aegypti)-OBPgpLYS with additional
      His-tag

<400> SEQUENCE: 67

Met Gly Gly Leu Lys Lys Leu Gly Lys Lys Leu Glu Gly Ala Gly Lys
1               5                   10                  15

Arg Val Phe Asn Ala Ala Glu Lys Ala Leu Pro Val Val Ala Gly Ala
            20                  25                  30

Lys Ala Leu Arg Lys Gly Ser Lys Asn Ser Glu Lys Asn Ala Ser Ile
        35                  40                  45

Ile Met Ser Ile Gln Arg Thr Leu Ala Ser Leu Ser Leu Tyr Gly Gly
    50                  55                  60

Arg Ile Asp Gly Leu Phe Gly Glu Lys Cys Arg Gly Ala Ile Ile Leu
65                  70                  75                  80

Met Leu Asn Lys Val Tyr Pro Asn Phe Ser Thr Asn Lys Leu Pro Ser
                85                  90                  95

Asn Thr Tyr Glu Ala Glu Ser Val Phe Thr Phe Leu Gln Thr Ala Leu
            100                 105                 110

Ala Gly Val Gly Leu Tyr Thr Ile Thr Ile Asp Gly Lys Trp Gly Gly
        115                 120                 125

Thr Ser Gln Gly Ala Ile Asp Ala Leu Val Lys Ser Tyr Arg Gln Ile
    130                 135                 140

Thr Glu Ala Glu Arg Ala Gly Ser Thr Leu Pro Leu Gly Leu Ala Thr
145                 150                 155                 160

Val Met Ser Lys His Met Ser Ile Glu Gln Leu Arg Ala Met Leu Pro
                165                 170                 175

Thr Asp Arg Gln Gly Tyr Ala Glu Val Tyr Ile Asp Pro Leu Asn Glu
            180                 185                 190

Thr Met Asp Ile Phe Glu Ile Asn Thr Pro Leu Arg Ile Ala His Phe
        195                 200                 205

Met Ala Gln Ile Leu His Glu Thr Ala Cys Phe Lys Tyr Thr Glu Glu
    210                 215                 220

Leu Ala Ser Gly Lys Ala Tyr Glu Gly Arg Ala Asp Leu Gly Asn Thr
```

-continued

```
225                 230                 235                 240

Arg Pro Gly Asp Gly Pro Leu Phe Lys Gly Arg Gly Leu Leu Gln Ile
                245                 250                 255

Thr Gly Arg Leu Asn Tyr Val Lys Cys Gln Val Tyr Leu Arg Glu Lys
            260                 265                 270

Leu Lys Asp Pro Thr Phe Asp Ile Thr Ser Ser Val Thr Cys Ala Gln
        275                 280                 285

Gln Leu Ser Glu Ser Pro Leu Leu Ala Ala Leu Ala Ser Gly Tyr Phe
    290                 295                 300

Trp Arg Phe Ile Lys Pro Lys Leu Asn Glu Thr Ala Asp Lys Asp Asp
305                 310                 315                 320

Ile Tyr Trp Val Ser Val Tyr Val Asn Gly Tyr Ala Lys Gln Ala Asn
                325                 330                 335

Pro Tyr Tyr Pro Asn Arg Asp Lys Glu Pro Asn His Met Lys Glu Arg
            340                 345                 350

Val Gln Met Leu Ala Val Thr Lys Lys Ala His Gly Ile Val Leu Glu
        355                 360                 365

His His His His His His
    370


<210> SEQ ID NO 68
<211> LENGTH: 13
<212> TYPE: PRT
<213> ORGANISM: unknown
<220> FEATURE:
<223> OTHER INFORMATION: antimicrobial peptide Alpha 4

<400> SEQUENCE: 68

Pro Asn Arg Ala Lys Arg Val Ile Thr Thr Phe Arg Thr
1               5                   10


<210> SEQ ID NO 69
<211> LENGTH: 327
<212> TYPE: PRT
<213> ORGANISM: unknown
<220> FEATURE:
<223> OTHER INFORMATION: OBPgpLYS fragment

<400> SEQUENCE: 69

Lys Asn Ser Glu Lys Asn Ala Ser Ile Ile Met Ser Ile Gln Arg Thr
1               5                   10                  15

Leu Ala Ser Leu Ser Leu Tyr Gly Gly Arg Ile Asp Gly Leu Phe Gly
            20                  25                  30

Glu Lys Cys Arg Gly Ala Ile Ile Leu Met Leu Asn Lys Val Tyr Pro
        35                  40                  45

Asn Phe Ser Thr Asn Lys Leu Pro Ser Asn Thr Tyr Glu Ala Glu Ser
    50                  55                  60

Val Phe Thr Phe Leu Gln Thr Ala Leu Ala Gly Val Gly Leu Tyr Thr
65                  70                  75                  80

Ile Thr Ile Asp Gly Lys Trp Gly Gly Thr Ser Gln Gly Ala Ile Asp
                85                  90                  95

Ala Leu Val Lys Ser Tyr Arg Gln Ile Thr Glu Ala Glu Arg Ala Gly
            100                 105                 110

Ser Thr Leu Pro Leu Gly Leu Ala Thr Val Met Ser Lys His Met Ser
        115                 120                 125

Ile Glu Gln Leu Arg Ala Met Leu Pro Thr Asp Arg Gln Gly Tyr Ala
    130                 135                 140
```

-continued

```
Glu Val Tyr Ile Asp Pro Leu Asn Glu Thr Met Asp Ile Phe Glu Ile
145                 150                 155                 160

Asn Thr Pro Leu Arg Ile Ala His Phe Met Ala Gln Ile Leu His Glu
                165                 170                 175

Thr Ala Cys Phe Lys Tyr Thr Glu Glu Leu Ala Ser Gly Lys Ala Tyr
            180                 185                 190

Glu Gly Arg Ala Asp Leu Gly Asn Thr Arg Pro Gly Asp Gly Pro Leu
        195                 200                 205

Phe Lys Gly Arg Gly Leu Leu Gln Ile Thr Gly Arg Leu Asn Tyr Val
    210                 215                 220

Lys Cys Gln Val Tyr Leu Arg Glu Lys Leu Lys Asp Pro Thr Phe Asp
225                 230                 235                 240

Ile Thr Ser Ser Val Thr Cys Ala Gln Gln Leu Ser Glu Ser Pro Leu
                245                 250                 255

Leu Ala Ala Leu Ala Ser Gly Tyr Phe Trp Arg Phe Ile Lys Pro Lys
            260                 265                 270

Leu Asn Glu Thr Ala Asp Lys Asp Asp Ile Tyr Trp Val Ser Val Tyr
        275                 280                 285

Val Asn Gly Tyr Ala Lys Gln Ala Asn Pro Tyr Tyr Pro Asn Arg Asp
    290                 295                 300

Lys Glu Pro Asn His Met Lys Glu Arg Val Gln Met Leu Ala Val Thr
305                 310                 315                 320

Lys Lys Ala Leu Gly Ile Val
                325


<210> SEQ ID NO 70
<211> LENGTH: 18
<212> TYPE: PRT
<213> ORGANISM: unknown
<220> FEATURE:
<223> OTHER INFORMATION: antimicropial peptide Artilysin1

<400> SEQUENCE: 70

Gly Phe Phe Ile Pro Ala Val Ile Leu Pro Ser Ile Ala Phe Leu Ile
1               5                   10                  15

Val Pro


<210> SEQ ID NO 71
<211> LENGTH: 25
<212> TYPE: PRT
<213> ORGANISM: unknown
<220> FEATURE:
<223> OTHER INFORMATION: antimicrobial peptide Artilysin2

<400> SEQUENCE: 71

Gly Lys Pro Gly Trp Leu Ile Lys Lys Ala Leu Val Phe Lys Lys Leu
1               5                   10                  15

Ile Arg Arg Pro Leu Lys Arg Leu Ala
            20                  25


<210> SEQ ID NO 72
<211> LENGTH: 19
<212> TYPE: PRT
<213> ORGANISM: unknown
<220> FEATURE:
<223> OTHER INFORMATION: antimicrobial peptide Parasin 1

<400> SEQUENCE: 72

Lys Gly Arg Gly Lys Gln Gly Gly Lys Val Arg Ala Lys Ala Lys Thr
1               5                   10                  15
```

Arg Ser Ser

<210> SEQ ID NO 73
<211> LENGTH: 25
<212> TYPE: PRT
<213> ORGANISM: unknown
<220> FEATURE:
<223> OTHER INFORMATION: antimicrobial peptide Lycotoxin

<400> SEQUENCE: 73

Ile Trp Leu Thr Ala Leu Lys Phe Leu Gly Lys His Ala Ala Lys Lys
1 5 10 15

Leu Ala Lys Gln Gln Leu Ser Lys Leu
20 25

<210> SEQ ID NO 74
<211> LENGTH: 346
<212> TYPE: PRT
<213> ORGANISM: unknown
<220> FEATURE:
<223> OTHER INFORMATION: Alpha4-OBPgpLYS

<400> SEQUENCE: 74

Met Gly Ser Pro Asn Arg Ala Lys Arg Val Ile Thr Thr Phe Arg Thr
1 5 10 15

Gly Ser Ser Lys Asn Ser Glu Lys Asn Ala Ser Ile Ile Met Ser Ile
20 25 30

Gln Arg Thr Leu Ala Ser Leu Ser Leu Tyr Gly Gly Arg Ile Asp Gly
35 40 45

Leu Phe Gly Glu Lys Cys Arg Gly Ala Ile Ile Leu Met Leu Asn Lys
50 55 60

Val Tyr Pro Asn Phe Ser Thr Asn Lys Leu Pro Ser Asn Thr Tyr Glu
65 70 75 80

Ala Glu Ser Val Phe Thr Phe Leu Gln Thr Ala Leu Ala Gly Val Gly
85 90 95

Leu Tyr Thr Ile Thr Ile Asp Gly Lys Trp Gly Gly Thr Ser Gln Gly
100 105 110

Ala Ile Asp Ala Leu Val Lys Ser Tyr Arg Gln Ile Thr Glu Ala Glu
115 120 125

Arg Ala Gly Ser Thr Leu Pro Leu Gly Leu Ala Thr Val Met Ser Lys
130 135 140

His Met Ser Ile Glu Gln Leu Arg Ala Met Leu Pro Thr Asp Arg Gln
145 150 155 160

Gly Tyr Ala Glu Val Tyr Ile Asp Pro Leu Asn Glu Thr Met Asp Ile
165 170 175

Phe Glu Ile Asn Thr Pro Leu Arg Ile Ala His Phe Met Ala Gln Ile
180 185 190

Leu His Glu Thr Ala Cys Phe Lys Tyr Thr Glu Glu Leu Ala Ser Gly
195 200 205

Lys Ala Tyr Glu Gly Arg Ala Asp Leu Gly Asn Thr Arg Pro Gly Asp
210 215 220

Gly Pro Leu Phe Lys Gly Arg Gly Leu Leu Gln Ile Thr Gly Arg Leu
225 230 235 240

Asn Tyr Val Lys Cys Gln Val Tyr Leu Arg Glu Lys Leu Lys Asp Pro
245 250 255

Thr Phe Asp Ile Thr Ser Ser Val Thr Cys Ala Gln Gln Leu Ser Glu
260 265 270

Ser Pro Leu Leu Ala Ala Leu Ala Ser Gly Tyr Phe Trp Arg Phe Ile
        275                 280                 285

Lys Pro Lys Leu Asn Glu Thr Ala Asp Lys Asp Asp Ile Tyr Trp Val
    290                 295                 300

Ser Val Tyr Val Asn Gly Tyr Ala Lys Gln Ala Asn Pro Tyr Tyr Pro
305                 310                 315                 320

Asn Arg Asp Lys Glu Pro Asn His Met Lys Glu Arg Val Gln Met Leu
                325                 330                 335

Ala Val Thr Lys Lys Ala His Gly Ile Val
            340                 345

<210> SEQ ID NO 75
<211> LENGTH: 354
<212> TYPE: PRT
<213> ORGANISM: unknown
<220> FEATURE:
<223> OTHER INFORMATION: Alpha4-OBPgpLYS with additional His-tag

<400> SEQUENCE: 75

Met Gly Ser Pro Asn Arg Ala Lys Arg Val Ile Thr Thr Phe Arg Thr
1               5                   10                  15

Gly Ser Ser Lys Asn Ser Glu Lys Asn Ala Ser Ile Ile Met Ser Ile
            20                  25                  30

Gln Arg Thr Leu Ala Ser Leu Ser Leu Tyr Gly Gly Arg Ile Asp Gly
        35                  40                  45

Leu Phe Gly Glu Lys Cys Arg Gly Ala Ile Ile Leu Met Leu Asn Lys
    50                  55                  60

Val Tyr Pro Asn Phe Ser Thr Asn Lys Leu Pro Ser Asn Thr Tyr Glu
65                  70                  75                  80

Ala Glu Ser Val Phe Thr Phe Leu Gln Thr Ala Leu Ala Gly Val Gly
                85                  90                  95

Leu Tyr Thr Ile Thr Ile Asp Gly Lys Trp Gly Gly Thr Ser Gln Gly
            100                 105                 110

Ala Ile Asp Ala Leu Val Lys Ser Tyr Arg Gln Ile Thr Glu Ala Glu
        115                 120                 125

Arg Ala Gly Ser Thr Leu Pro Leu Gly Leu Ala Thr Val Met Ser Lys
    130                 135                 140

His Met Ser Ile Glu Gln Leu Arg Ala Met Leu Pro Thr Asp Arg Gln
145                 150                 155                 160

Gly Tyr Ala Glu Val Tyr Ile Asp Pro Leu Asn Glu Thr Met Asp Ile
                165                 170                 175

Phe Glu Ile Asn Thr Pro Leu Arg Ile Ala His Phe Met Ala Gln Ile
            180                 185                 190

Leu His Glu Thr Ala Cys Phe Lys Tyr Thr Glu Glu Leu Ala Ser Gly
        195                 200                 205

Lys Ala Tyr Glu Gly Arg Ala Asp Leu Gly Asn Thr Arg Pro Gly Asp
    210                 215                 220

Gly Pro Leu Phe Lys Gly Arg Gly Leu Leu Gln Ile Thr Gly Arg Leu
225                 230                 235                 240

Asn Tyr Val Lys Cys Gln Val Tyr Leu Arg Glu Lys Leu Lys Asp Pro
                245                 250                 255

Thr Phe Asp Ile Thr Ser Ser Val Thr Cys Ala Gln Gln Leu Ser Glu
            260                 265                 270

Ser Pro Leu Leu Ala Ala Leu Ala Ser Gly Tyr Phe Trp Arg Phe Ile
        275                 280                 285

```
Lys Pro Lys Leu Asn Glu Thr Ala Asp Lys Asp Asp Ile Tyr Trp Val
    290                 295                 300

Ser Val Tyr Val Asn Gly Tyr Ala Lys Gln Ala Asn Pro Tyr Tyr Pro
305                 310                 315                 320

Asn Arg Asp Lys Glu Pro Asn His Met Lys Glu Arg Val Gln Met Leu
                325                 330                 335

Ala Val Thr Lys Lys Ala His Gly Ile Val Lys Gly His His His His
            340                 345                 350

His His


<210> SEQ ID NO 76
<211> LENGTH: 338
<212> TYPE: PRT
<213> ORGANISM: unknown
<220> FEATURE:
<223> OTHER INFORMATION: OBPgpLys

<400> SEQUENCE: 76

Met Gly Ser Phe Phe Val Ala Pro Gly Ser Ser Lys Asn Ser Glu Lys
1               5                   10                  15

Asn Ala Ser Ile Ile Met Ser Ile Gln Arg Thr Leu Ala Ser Leu Ser
            20                  25                  30

Leu Tyr Gly Gly Arg Ile Asp Gly Leu Phe Gly Glu Lys Cys Arg Gly
        35                  40                  45

Ala Ile Ile Leu Met Leu Asn Lys Val Tyr Pro Asn Phe Ser Thr Asn
    50                  55                  60

Lys Leu Pro Ser Asn Thr Tyr Glu Ala Glu Ser Val Phe Thr Phe Leu
65                  70                  75                  80

Gln Thr Ala Leu Ala Gly Val Gly Leu Tyr Thr Ile Thr Ile Asp Gly
                85                  90                  95

Lys Trp Gly Gly Thr Ser Gln Gly Ala Ile Asp Ala Leu Val Lys Ser
            100                 105                 110

Tyr Arg Gln Ile Thr Glu Ala Glu Arg Ala Gly Ser Thr Leu Pro Leu
        115                 120                 125

Gly Leu Ala Thr Val Met Ser Lys His Met Ser Ile Glu Gln Leu Arg
    130                 135                 140

Ala Met Leu Pro Thr Asp Arg Gln Gly Tyr Ala Glu Val Tyr Ile Asp
145                 150                 155                 160

Pro Leu Asn Glu Thr Met Asp Ile Phe Glu Ile Asn Thr Pro Leu Arg
                165                 170                 175

Ile Ala His Phe Met Ala Gln Ile Leu His Glu Thr Ala Cys Phe Lys
            180                 185                 190

Tyr Thr Glu Glu Leu Ala Ser Gly Lys Ala Tyr Glu Gly Arg Ala Asp
        195                 200                 205

Leu Gly Asn Thr Arg Pro Gly Asp Gly Pro Leu Phe Lys Gly Arg Gly
    210                 215                 220

Leu Leu Gln Ile Thr Gly Arg Leu Asn Tyr Val Lys Cys Gln Val Tyr
225                 230                 235                 240

Leu Arg Glu Lys Leu Lys Asp Pro Thr Phe Asp Ile Thr Ser Ser Val
                245                 250                 255

Thr Cys Ala Gln Gln Leu Ser Glu Ser Pro Leu Leu Ala Ala Leu Ala
            260                 265                 270

Ser Gly Tyr Phe Trp Arg Phe Ile Lys Pro Lys Leu Asn Glu Thr Ala
        275                 280                 285
```

Asp Lys Asp Asp Ile Tyr Trp Val Ser Val Tyr Val Asn Gly Tyr Ala
    290                 295                 300

Lys Gln Ala Asn Pro Tyr Tyr Pro Asn Arg Asp Lys Glu Pro Asn His
305                 310                 315                 320

Met Lys Glu Arg Val Gln Met Leu Ala Val Thr Lys Lys Ala His Gly
                325                 330                 335

Ile Val

<210> SEQ ID NO 77
<211> LENGTH: 346
<212> TYPE: PRT
<213> ORGANISM: unknown
<220> FEATURE:
<223> OTHER INFORMATION: OBPgpLys with additional His-tag

<400> SEQUENCE: 77

Met Gly Ser Phe Phe Val Ala Pro Gly Ser Ser Lys Asn Ser Glu Lys
1               5                   10                  15

Asn Ala Ser Ile Ile Met Ser Ile Gln Arg Thr Leu Ala Ser Leu Ser
            20                  25                  30

Leu Tyr Gly Gly Arg Ile Asp Gly Leu Phe Gly Glu Lys Cys Arg Gly
        35                  40                  45

Ala Ile Ile Leu Met Leu Asn Lys Val Tyr Pro Asn Phe Ser Thr Asn
    50                  55                  60

Lys Leu Pro Ser Asn Thr Tyr Glu Ala Glu Ser Val Phe Thr Phe Leu
65                  70                  75                  80

Gln Thr Ala Leu Ala Gly Val Gly Leu Tyr Thr Ile Thr Ile Asp Gly
                85                  90                  95

Lys Trp Gly Gly Thr Ser Gln Gly Ala Ile Asp Ala Leu Val Lys Ser
            100                 105                 110

Tyr Arg Gln Ile Thr Glu Ala Glu Arg Ala Gly Ser Thr Leu Pro Leu
        115                 120                 125

Gly Leu Ala Thr Val Met Ser Lys His Met Ser Ile Glu Gln Leu Arg
    130                 135                 140

Ala Met Leu Pro Thr Asp Arg Gln Gly Tyr Ala Glu Val Tyr Ile Asp
145                 150                 155                 160

Pro Leu Asn Glu Thr Met Asp Ile Phe Glu Ile Asn Thr Pro Leu Arg
                165                 170                 175

Ile Ala His Phe Met Ala Gln Ile Leu His Glu Thr Ala Cys Phe Lys
            180                 185                 190

Tyr Thr Glu Glu Leu Ala Ser Gly Lys Ala Tyr Glu Gly Arg Ala Asp
        195                 200                 205

Leu Gly Asn Thr Arg Pro Gly Asp Gly Pro Leu Phe Lys Gly Arg Gly
    210                 215                 220

Leu Leu Gln Ile Thr Gly Arg Leu Asn Tyr Val Lys Cys Gln Val Tyr
225                 230                 235                 240

Leu Arg Glu Lys Leu Lys Asp Pro Thr Phe Asp Ile Thr Ser Ser Val
                245                 250                 255

Thr Cys Ala Gln Gln Leu Ser Glu Ser Pro Leu Leu Ala Ala Leu Ala
            260                 265                 270

Ser Gly Tyr Phe Trp Arg Phe Ile Lys Pro Lys Leu Asn Glu Thr Ala
        275                 280                 285

Asp Lys Asp Asp Ile Tyr Trp Val Ser Val Tyr Val Asn Gly Tyr Ala
    290                 295                 300

Lys Gln Ala Asn Pro Tyr Tyr Pro Asn Arg Asp Lys Glu Pro Asn His

-continued 305 310 315 320

Met Lys Glu Arg Val Gln Met Leu Ala Val Thr Lys Lys Ala His Gly
325 330 335

Ile Val Lys Gly His His His His His His
340 345

<210> SEQ ID NO 78
<211> LENGTH: 351
<212> TYPE: PRT
<213> ORGANISM: unknown
<220> FEATURE:
<223> OTHER INFORMATION: Artilys1-OBPgpLys

<400> SEQUENCE: 78

Met Gly Ser Gly Phe Phe Ile Pro Ala Val Ile Leu Pro Ser Ile Ala
1 5 10 15

Phe Leu Ile Val Pro Gly Ser Ser Lys Asn Ser Glu Lys Asn Ala Ser
20 25 30

Ile Ile Met Ser Ile Gln Arg Thr Leu Ala Ser Leu Ser Leu Tyr Gly
35 40 45

Gly Arg Ile Asp Gly Leu Phe Gly Glu Lys Cys Arg Gly Ala Ile Ile
50 55 60

Leu Met Leu Asn Lys Val Tyr Pro Asn Phe Ser Thr Asn Lys Leu Pro
65 70 75 80

Ser Asn Thr Tyr Glu Ala Glu Ser Val Phe Thr Phe Leu Gln Thr Ala
85 90 95

Leu Ala Gly Val Gly Leu Tyr Thr Ile Thr Ile Asp Gly Lys Trp Gly
100 105 110

Gly Thr Ser Gln Gly Ala Ile Asp Ala Leu Val Lys Ser Tyr Arg Gln
115 120 125

Ile Thr Glu Ala Glu Arg Ala Gly Ser Thr Leu Pro Leu Gly Leu Ala
130 135 140

Thr Val Met Ser Lys His Met Ser Ile Glu Gln Leu Arg Ala Met Leu
145 150 155 160

Pro Thr Asp Arg Gln Gly Tyr Ala Glu Val Tyr Ile Asp Pro Leu Asn
165 170 175

Glu Thr Met Asp Ile Phe Glu Ile Asn Thr Pro Leu Arg Ile Ala His
180 185 190

Phe Met Ala Gln Ile Leu His Glu Thr Ala Cys Phe Lys Tyr Thr Glu
195 200 205

Glu Leu Ala Ser Gly Lys Ala Tyr Glu Gly Arg Ala Asp Leu Gly Asn
210 215 220

Thr Arg Pro Gly Asp Gly Pro Leu Phe Lys Gly Arg Gly Leu Leu Gln
225 230 235 240

Ile Thr Gly Arg Leu Asn Tyr Val Lys Cys Gln Val Tyr Leu Arg Glu
245 250 255

Lys Leu Lys Asp Pro Thr Phe Asp Ile Thr Ser Ser Val Thr Cys Ala
260 265 270

Gln Gln Leu Ser Glu Ser Pro Leu Leu Ala Ala Leu Ala Ser Gly Tyr
275 280 285

Phe Trp Arg Phe Ile Lys Pro Lys Leu Asn Glu Thr Ala Asp Lys Asp
290 295 300

Asp Ile Tyr Trp Val Ser Val Tyr Val Asn Gly Tyr Ala Lys Gln Ala
305 310 315 320

Asn Pro Tyr Tyr Pro Asn Arg Asp Lys Glu Pro Asn His Met Lys Glu

```
                325                 330                 335

Arg Val Gln Met Leu Ala Val Thr Lys Lys Ala His Gly Ile Val
            340                 345                 350


<210> SEQ ID NO 79
<211> LENGTH: 359
<212> TYPE: PRT
<213> ORGANISM: unknown
<220> FEATURE:
<223> OTHER INFORMATION: Artilys1-OBPgpLys with additional His-tag

<400> SEQUENCE: 79

Met Gly Ser Gly Phe Phe Ile Pro Ala Val Ile Leu Pro Ser Ile Ala
1               5                   10                  15

Phe Leu Ile Val Pro Gly Ser Ser Lys Asn Ser Glu Lys Asn Ala Ser
            20                  25                  30

Ile Ile Met Ser Ile Gln Arg Thr Leu Ala Ser Leu Ser Leu Tyr Gly
        35                  40                  45

Gly Arg Ile Asp Gly Leu Phe Gly Glu Lys Cys Arg Gly Ala Ile Ile
    50                  55                  60

Leu Met Leu Asn Lys Val Tyr Pro Asn Phe Ser Thr Asn Lys Leu Pro
65                  70                  75                  80

Ser Asn Thr Tyr Glu Ala Glu Ser Val Phe Thr Phe Leu Gln Thr Ala
                85                  90                  95

Leu Ala Gly Val Gly Leu Tyr Thr Ile Thr Ile Asp Gly Lys Trp Gly
            100                 105                 110

Gly Thr Ser Gln Gly Ala Ile Asp Ala Leu Val Lys Ser Tyr Arg Gln
        115                 120                 125

Ile Thr Glu Ala Glu Arg Ala Gly Ser Thr Leu Pro Leu Gly Leu Ala
    130                 135                 140

Thr Val Met Ser Lys His Met Ser Ile Glu Gln Leu Arg Ala Met Leu
145                 150                 155                 160

Pro Thr Asp Arg Gln Gly Tyr Ala Glu Val Tyr Ile Asp Pro Leu Asn
                165                 170                 175

Glu Thr Met Asp Ile Phe Glu Ile Asn Thr Pro Leu Arg Ile Ala His
            180                 185                 190

Phe Met Ala Gln Ile Leu His Glu Thr Ala Cys Phe Lys Tyr Thr Glu
        195                 200                 205

Glu Leu Ala Ser Gly Lys Ala Tyr Glu Gly Arg Ala Asp Leu Gly Asn
    210                 215                 220

Thr Arg Pro Gly Asp Gly Pro Leu Phe Lys Gly Arg Gly Leu Leu Gln
225                 230                 235                 240

Ile Thr Gly Arg Leu Asn Tyr Val Lys Cys Gln Val Tyr Leu Arg Glu
                245                 250                 255

Lys Leu Lys Asp Pro Thr Phe Asp Ile Thr Ser Ser Val Thr Cys Ala
            260                 265                 270

Gln Gln Leu Ser Glu Ser Pro Leu Leu Ala Ala Leu Ala Ser Gly Tyr
        275                 280                 285

Phe Trp Arg Phe Ile Lys Pro Lys Leu Asn Glu Thr Ala Asp Lys Asp
    290                 295                 300

Asp Ile Tyr Trp Val Ser Val Tyr Val Asn Gly Tyr Ala Lys Gln Ala
305                 310                 315                 320

Asn Pro Tyr Tyr Pro Asn Arg Asp Lys Glu Pro Asn His Met Lys Glu
                325                 330                 335

Arg Val Gln Met Leu Ala Val Thr Lys Lys Ala His Gly Ile Val Lys
```

```
            340                 345                 350

Gly His His His His His His
        355


<210> SEQ ID NO 80
<211> LENGTH: 358
<212> TYPE: PRT
<213> ORGANISM: unknown
<220> FEATURE:
<223> OTHER INFORMATION: Artilys2-OBPgpLYS

<400> SEQUENCE: 80

Met Gly Ser Gly Lys Pro Gly Trp Leu Ile Lys Lys Ala Leu Val Phe
1               5                   10                  15

Lys Lys Leu Ile Arg Arg Pro Leu Lys Arg Leu Ala Gly Ser Ser Lys
            20                  25                  30

Asn Ser Glu Lys Asn Ala Ser Ile Ile Met Ser Ile Gln Arg Thr Leu
        35                  40                  45

Ala Ser Leu Ser Leu Tyr Gly Gly Arg Ile Asp Gly Leu Phe Gly Glu
    50                  55                  60

Lys Cys Arg Gly Ala Ile Ile Leu Met Leu Asn Lys Val Tyr Pro Asn
65                  70                  75                  80

Phe Ser Thr Asn Lys Leu Pro Ser Asn Thr Tyr Glu Ala Glu Ser Val
                85                  90                  95

Phe Thr Phe Leu Gln Thr Ala Leu Ala Gly Val Gly Leu Tyr Thr Ile
            100                 105                 110

Thr Ile Asp Gly Lys Trp Gly Gly Thr Ser Gln Gly Ala Ile Asp Ala
        115                 120                 125

Leu Val Lys Ser Tyr Arg Gln Ile Thr Glu Ala Glu Arg Ala Gly Ser
    130                 135                 140

Thr Leu Pro Leu Gly Leu Ala Thr Val Met Ser Lys His Met Ser Ile
145                 150                 155                 160

Glu Gln Leu Arg Ala Met Leu Pro Thr Asp Arg Gln Gly Tyr Ala Glu
                165                 170                 175

Val Tyr Ile Asp Pro Leu Asn Glu Thr Met Asp Ile Phe Glu Ile Asn
            180                 185                 190

Thr Pro Leu Arg Ile Ala His Phe Met Ala Gln Ile Leu His Glu Thr
        195                 200                 205

Ala Cys Phe Lys Tyr Thr Glu Glu Leu Ala Ser Gly Lys Ala Tyr Glu
    210                 215                 220

Gly Arg Ala Asp Leu Gly Asn Thr Arg Pro Gly Asp Gly Pro Leu Phe
225                 230                 235                 240

Lys Gly Arg Gly Leu Leu Gln Ile Thr Gly Arg Leu Asn Tyr Val Lys
                245                 250                 255

Cys Gln Val Tyr Leu Arg Glu Lys Leu Lys Asp Pro Thr Phe Asp Ile
            260                 265                 270

Thr Ser Ser Val Thr Cys Ala Gln Gln Leu Ser Glu Ser Pro Leu Leu
        275                 280                 285

Ala Ala Leu Ala Ser Gly Tyr Phe Trp Arg Phe Ile Lys Pro Lys Leu
    290                 295                 300

Asn Glu Thr Ala Asp Lys Asp Asp Ile Tyr Trp Val Ser Val Tyr Val
305                 310                 315                 320

Asn Gly Tyr Ala Lys Gln Ala Asn Pro Tyr Tyr Pro Asn Arg Asp Lys
                325                 330                 335

Glu Pro Asn His Met Lys Glu Arg Val Gln Met Leu Ala Val Thr Lys
```

340 345 350

Lys Ala His Gly Ile Val
355

<210> SEQ ID NO 81
<211> LENGTH: 366
<212> TYPE: PRT
<213> ORGANISM: unknown
<220> FEATURE:
<223> OTHER INFORMATION: Artilys2-OBPgpLYS with additional His-tag

<400> SEQUENCE: 81

Met Gly Ser Gly Lys Pro Gly Trp Leu Ile Lys Lys Ala Leu Val Phe
1 5 10 15

Lys Lys Leu Ile Arg Arg Pro Leu Lys Arg Leu Ala Gly Ser Ser Lys
20 25 30

Asn Ser Glu Lys Asn Ala Ser Ile Ile Met Ser Ile Gln Arg Thr Leu
35 40 45

Ala Ser Leu Ser Leu Tyr Gly Gly Arg Ile Asp Gly Leu Phe Gly Glu
50 55 60

Lys Cys Arg Gly Ala Ile Ile Leu Met Leu Asn Lys Val Tyr Pro Asn
65 70 75 80

Phe Ser Thr Asn Lys Leu Pro Ser Asn Thr Tyr Glu Ala Glu Ser Val
85 90 95

Phe Thr Phe Leu Gln Thr Ala Leu Ala Gly Val Gly Leu Tyr Thr Ile
100 105 110

Thr Ile Asp Gly Lys Trp Gly Gly Thr Ser Gln Gly Ala Ile Asp Ala
115 120 125

Leu Val Lys Ser Tyr Arg Gln Ile Thr Glu Ala Glu Arg Ala Gly Ser
130 135 140

Thr Leu Pro Leu Gly Leu Ala Thr Val Met Ser Lys His Met Ser Ile
145 150 155 160

Glu Gln Leu Arg Ala Met Leu Pro Thr Asp Arg Gln Gly Tyr Ala Glu
165 170 175

Val Tyr Ile Asp Pro Leu Asn Glu Thr Met Asp Ile Phe Glu Ile Asn
180 185 190

Thr Pro Leu Arg Ile Ala His Phe Met Ala Gln Ile Leu His Glu Thr
195 200 205

Ala Cys Phe Lys Tyr Thr Glu Glu Leu Ala Ser Gly Lys Ala Tyr Glu
210 215 220

Gly Arg Ala Asp Leu Gly Asn Thr Arg Pro Gly Asp Gly Pro Leu Phe
225 230 235 240

Lys Gly Arg Gly Leu Leu Gln Ile Thr Gly Arg Leu Asn Tyr Val Lys
245 250 255

Cys Gln Val Tyr Leu Arg Glu Lys Leu Lys Asp Pro Thr Phe Asp Ile
260 265 270

Thr Ser Ser Val Thr Cys Ala Gln Gln Leu Ser Glu Ser Pro Leu Leu
275 280 285

Ala Ala Leu Ala Ser Gly Tyr Phe Trp Arg Phe Ile Lys Pro Lys Leu
290 295 300

Asn Glu Thr Ala Asp Lys Asp Asp Ile Tyr Trp Val Ser Val Tyr Val
305 310 315 320

Asn Gly Tyr Ala Lys Gln Ala Asn Pro Tyr Tyr Pro Asn Arg Asp Lys
325 330 335

Glu Pro Asn His Met Lys Glu Arg Val Gln Met Leu Ala Val Thr Lys 340 345 350

Lys Ala His Gly Ile Val Lys Gly His His His His His His
355 360 365

<210> SEQ ID NO 82
<211> LENGTH: 352
<212> TYPE: PRT
<213> ORGANISM: unknown
<220> FEATURE:
<223> OTHER INFORMATION: Parasin1-OBPgpLys

<400> SEQUENCE: 82

Met Gly Ser Lys Gly Arg Gly Lys Gln Gly Gly Lys Val Arg Ala Lys
1 5 10 15

Ala Lys Thr Arg Ser Ser Gly Ser Ser Lys Asn Ser Glu Lys Asn Ala
20 25 30

Ser Ile Ile Met Ser Ile Gln Arg Thr Leu Ala Ser Leu Ser Leu Tyr
35 40 45

Gly Gly Arg Ile Asp Gly Leu Phe Gly Glu Lys Cys Arg Gly Ala Ile
50 55 60

Ile Leu Met Leu Asn Lys Val Tyr Pro Asn Phe Ser Thr Asn Lys Leu
65 70 75 80

Pro Ser Asn Thr Tyr Glu Ala Glu Ser Val Phe Thr Phe Leu Gln Thr
85 90 95

Ala Leu Ala Gly Val Gly Leu Tyr Thr Ile Thr Ile Asp Gly Lys Trp
100 105 110

Gly Gly Thr Ser Gln Gly Ala Ile Asp Ala Leu Val Lys Ser Tyr Arg
115 120 125

Gln Ile Thr Glu Ala Glu Arg Ala Gly Ser Thr Leu Pro Leu Gly Leu
130 135 140

Ala Thr Val Met Ser Lys His Met Ser Ile Glu Gln Leu Arg Ala Met
145 150 155 160

Leu Pro Thr Asp Arg Gln Gly Tyr Ala Glu Val Tyr Ile Asp Pro Leu
165 170 175

Asn Glu Thr Met Asp Ile Phe Glu Ile Asn Thr Pro Leu Arg Ile Ala
180 185 190

His Phe Met Ala Gln Ile Leu His Glu Thr Ala Cys Phe Lys Tyr Thr
195 200 205

Glu Glu Leu Ala Ser Gly Lys Ala Tyr Glu Gly Arg Ala Asp Leu Gly
210 215 220

Asn Thr Arg Pro Gly Asp Gly Pro Leu Phe Lys Gly Arg Gly Leu Leu
225 230 235 240

Gln Ile Thr Gly Arg Leu Asn Tyr Val Lys Cys Gln Val Tyr Leu Arg
245 250 255

Glu Lys Leu Lys Asp Pro Thr Phe Asp Ile Thr Ser Ser Val Thr Cys
260 265 270

Ala Gln Gln Leu Ser Glu Ser Pro Leu Leu Ala Ala Leu Ala Ser Gly
275 280 285

Tyr Phe Trp Arg Phe Ile Lys Pro Lys Leu Asn Glu Thr Ala Asp Lys
290 295 300

Asp Asp Ile Tyr Trp Val Ser Val Tyr Val Asn Gly Tyr Ala Lys Gln
305 310 315 320

Ala Asn Pro Tyr Tyr Pro Asn Arg Asp Lys Glu Pro Asn His Met Lys
325 330 335

Glu Arg Val Gln Met Leu Ala Val Thr Lys Lys Ala His Gly Ile Val 340 345 350

<210> SEQ ID NO 83
<211> LENGTH: 360
<212> TYPE: PRT
<213> ORGANISM: unknown
<220> FEATURE:
<223> OTHER INFORMATION: Parasin1-OBPgpLys with additional His-tag

<400> SEQUENCE: 83

Met Gly Ser Lys Gly Arg Gly Lys Gln Gly Gly Lys Val Arg Ala Lys
1 5 10 15

Ala Lys Thr Arg Ser Ser Gly Ser Ser Lys Asn Ser Glu Lys Asn Ala
20 25 30

Ser Ile Ile Met Ser Ile Gln Arg Thr Leu Ala Ser Leu Ser Leu Tyr
35 40 45

Gly Gly Arg Ile Asp Gly Leu Phe Gly Glu Lys Cys Arg Gly Ala Ile
50 55 60

Ile Leu Met Leu Asn Lys Val Tyr Pro Asn Phe Ser Thr Asn Lys Leu
65 70 75 80

Pro Ser Asn Thr Tyr Glu Ala Glu Ser Val Phe Thr Phe Leu Gln Thr
85 90 95

Ala Leu Ala Gly Val Gly Leu Tyr Thr Ile Thr Ile Asp Gly Lys Trp
100 105 110

Gly Gly Thr Ser Gln Gly Ala Ile Asp Ala Leu Val Lys Ser Tyr Arg
115 120 125

Gln Ile Thr Glu Ala Glu Arg Ala Gly Ser Thr Leu Pro Leu Gly Leu
130 135 140

Ala Thr Val Met Ser Lys His Met Ser Ile Glu Gln Leu Arg Ala Met
145 150 155 160

Leu Pro Thr Asp Arg Gln Gly Tyr Ala Glu Val Tyr Ile Asp Pro Leu
165 170 175

Asn Glu Thr Met Asp Ile Phe Glu Ile Asn Thr Pro Leu Arg Ile Ala
180 185 190

His Phe Met Ala Gln Ile Leu His Glu Thr Ala Cys Phe Lys Tyr Thr
195 200 205

Glu Glu Leu Ala Ser Gly Lys Ala Tyr Glu Gly Arg Ala Asp Leu Gly
210 215 220

Asn Thr Arg Pro Gly Asp Gly Pro Leu Phe Lys Gly Arg Gly Leu Leu
225 230 235 240

Gln Ile Thr Gly Arg Leu Asn Tyr Val Lys Cys Gln Val Tyr Leu Arg
245 250 255

Glu Lys Leu Lys Asp Pro Thr Phe Asp Ile Thr Ser Ser Val Thr Cys
260 265 270

Ala Gln Gln Leu Ser Glu Ser Pro Leu Leu Ala Ala Leu Ala Ser Gly
275 280 285

Tyr Phe Trp Arg Phe Ile Lys Pro Lys Leu Asn Glu Thr Ala Asp Lys
290 295 300

Asp Asp Ile Tyr Trp Val Ser Val Tyr Val Asn Gly Tyr Ala Lys Gln
305 310 315 320

Ala Asn Pro Tyr Tyr Pro Asn Arg Asp Lys Glu Pro Asn His Met Lys
325 330 335

Glu Arg Val Gln Met Leu Ala Val Thr Lys Lys Ala His Gly Ile Val
340 345 350

Lys Gly His His His His His His 355 360

<210> SEQ ID NO 84
<211> LENGTH: 358
<212> TYPE: PRT
<213> ORGANISM: unknown
<220> FEATURE:
<223> OTHER INFORMATION: Lycotoxin-OBPgLys

<400> SEQUENCE: 84

```
Met Gly Ser Ile Trp Leu Thr Ala Leu Lys Phe Leu Gly Lys His Ala
1               5                   10                  15

Ala Lys Lys Leu Ala Lys Gln Gln Leu Ser Lys Leu Gly Ser Ser Lys
            20                  25                  30

Asn Ser Glu Lys Asn Ala Ser Ile Ile Met Ser Ile Gln Arg Thr Leu
        35                  40                  45

Ala Ser Leu Ser Leu Tyr Gly Gly Arg Ile Asp Gly Leu Phe Gly Glu
    50                  55                  60

Lys Cys Arg Gly Ala Ile Ile Leu Met Leu Asn Lys Val Tyr Pro Asn
65                  70                  75                  80

Phe Ser Thr Asn Lys Leu Pro Ser Asn Thr Tyr Glu Ala Glu Ser Val
                85                  90                  95

Phe Thr Phe Leu Gln Thr Ala Leu Ala Gly Val Gly Leu Tyr Thr Ile
            100                 105                 110

Thr Ile Asp Gly Lys Trp Gly Gly Thr Ser Gln Gly Ala Ile Asp Ala
        115                 120                 125

Leu Val Lys Ser Tyr Arg Gln Ile Thr Glu Ala Glu Arg Ala Gly Ser
    130                 135                 140

Thr Leu Pro Leu Gly Leu Ala Thr Val Met Ser Lys His Met Ser Ile
145                 150                 155                 160

Glu Gln Leu Arg Ala Met Leu Pro Thr Asp Arg Gln Gly Tyr Ala Glu
                165                 170                 175

Val Tyr Ile Asp Pro Leu Asn Glu Thr Met Asp Ile Phe Glu Ile Asn
            180                 185                 190

Thr Pro Leu Arg Ile Ala His Phe Met Ala Gln Ile Leu His Glu Thr
        195                 200                 205

Ala Cys Phe Lys Tyr Thr Glu Glu Leu Ala Ser Gly Lys Ala Tyr Glu
    210                 215                 220

Gly Arg Ala Asp Leu Gly Asn Thr Arg Pro Gly Asp Gly Pro Leu Phe
225                 230                 235                 240

Lys Gly Arg Gly Leu Leu Gln Ile Thr Gly Arg Leu Asn Tyr Val Lys
                245                 250                 255

Cys Gln Val Tyr Leu Arg Glu Lys Leu Lys Asp Pro Thr Phe Asp Ile
            260                 265                 270

Thr Ser Ser Val Thr Cys Ala Gln Gln Leu Ser Glu Ser Pro Leu Leu
        275                 280                 285

Ala Ala Leu Ala Ser Gly Tyr Phe Trp Arg Phe Ile Lys Pro Lys Leu
    290                 295                 300

Asn Glu Thr Ala Asp Lys Asp Asp Ile Tyr Trp Val Ser Val Tyr Val
305                 310                 315                 320

Asn Gly Tyr Ala Lys Gln Ala Asn Pro Tyr Tyr Pro Asn Arg Asp Lys
                325                 330                 335

Glu Pro Asn His Met Lys Glu Arg Val Gln Met Leu Ala Val Thr Lys
            340                 345                 350

Lys Ala His Gly Ile Val
```

355

<210> SEQ ID NO 85
<211> LENGTH: 366
<212> TYPE: PRT
<213> ORGANISM: unknown
<220> FEATURE:
<223> OTHER INFORMATION: Lycotoxin-OBPgLys with additional His-tag

<400> SEQUENCE: 85

Met Gly Ser Ile Trp Leu Thr Ala Leu Lys Phe Leu Gly Lys His Ala
1 5 10 15

Ala Lys Lys Leu Ala Lys Gln Gln Leu Ser Lys Leu Gly Ser Ser Lys
20 25 30

Asn Ser Glu Lys Asn Ala Ser Ile Ile Met Ser Ile Gln Arg Thr Leu
35 40 45

Ala Ser Leu Ser Leu Tyr Gly Gly Arg Ile Asp Gly Leu Phe Gly Glu
50 55 60

Lys Cys Arg Gly Ala Ile Ile Leu Met Leu Asn Lys Val Tyr Pro Asn
65 70 75 80

Phe Ser Thr Asn Lys Leu Pro Ser Asn Thr Tyr Glu Ala Glu Ser Val
85 90 95

Phe Thr Phe Leu Gln Thr Ala Leu Ala Gly Val Gly Leu Tyr Thr Ile
100 105 110

Thr Ile Asp Gly Lys Trp Gly Gly Thr Ser Gln Gly Ala Ile Asp Ala
115 120 125

Leu Val Lys Ser Tyr Arg Gln Ile Thr Glu Ala Glu Arg Ala Gly Ser
130 135 140

Thr Leu Pro Leu Gly Leu Ala Thr Val Met Ser Lys His Met Ser Ile
145 150 155 160

Glu Gln Leu Arg Ala Met Leu Pro Thr Asp Arg Gln Gly Tyr Ala Glu
165 170 175

Val Tyr Ile Asp Pro Leu Asn Glu Thr Met Asp Ile Phe Glu Ile Asn
180 185 190

Thr Pro Leu Arg Ile Ala His Phe Met Ala Gln Ile Leu His Glu Thr
195 200 205

Ala Cys Phe Lys Tyr Thr Glu Glu Leu Ala Ser Gly Lys Ala Tyr Glu
210 215 220

Gly Arg Ala Asp Leu Gly Asn Thr Arg Pro Gly Asp Gly Pro Leu Phe
225 230 235 240

Lys Gly Arg Gly Leu Leu Gln Ile Thr Gly Arg Leu Asn Tyr Val Lys
245 250 255

Cys Gln Val Tyr Leu Arg Glu Lys Leu Lys Asp Pro Thr Phe Asp Ile
260 265 270

Thr Ser Ser Val Thr Cys Ala Gln Gln Leu Ser Glu Ser Pro Leu Leu
275 280 285

Ala Ala Leu Ala Ser Gly Tyr Phe Trp Arg Phe Ile Lys Pro Lys Leu
290 295 300

Asn Glu Thr Ala Asp Lys Asp Asp Ile Tyr Trp Val Ser Val Tyr Val
305 310 315 320

Asn Gly Tyr Ala Lys Gln Ala Asn Pro Tyr Tyr Pro Asn Arg Asp Lys
325 330 335

Glu Pro Asn His Met Lys Glu Arg Val Gln Met Leu Ala Val Thr Lys
340 345 350

Lys Ala His Gly Ile Val Lys Gly His His His His His His 355 360 365

<210> SEQ ID NO 86
<211> LENGTH: 328
<212> TYPE: PRT
<213> ORGANISM: unknown
<220> FEATURE:
<223> OTHER INFORMATION: OBPgpLYS

<400> SEQUENCE: 86

Met Lys Asn Ser Glu Lys Asn Ala Ser Ile Ile Met Ser Ile Gln Arg
1 5 10 15

Thr Leu Ala Ser Leu Ser Leu Tyr Gly Gly Arg Ile Asp Gly Leu Phe
20 25 30

Gly Glu Lys Cys Arg Gly Ala Ile Ile Leu Met Leu Asn Lys Val Tyr
35 40 45

Pro Asn Phe Ser Thr Asn Lys Leu Pro Ser Asn Thr Tyr Glu Ala Glu
50 55 60

Ser Val Phe Thr Phe Leu Gln Thr Ala Leu Ala Gly Val Gly Leu Tyr
65 70 75 80

Thr Ile Thr Ile Asp Gly Lys Trp Gly Gly Thr Ser Gln Gly Ala Ile
85 90 95

Asp Ala Leu Val Lys Ser Tyr Arg Gln Ile Thr Glu Ala Glu Arg Ala
100 105 110

Gly Ser Thr Leu Pro Leu Gly Leu Ala Thr Val Met Ser Lys His Met
115 120 125

Ser Ile Glu Gln Leu Arg Ala Met Leu Pro Thr Asp Arg Gln Gly Tyr
130 135 140

Ala Glu Val Tyr Ile Asp Pro Leu Asn Glu Thr Met Asp Ile Phe Glu
145 150 155 160

Ile Asn Thr Pro Leu Arg Ile Ala His Phe Met Ala Gln Ile Leu His
165 170 175

Glu Thr Ala Cys Phe Lys Tyr Thr Glu Glu Leu Ala Ser Gly Lys Ala
180 185 190

Tyr Glu Gly Arg Ala Asp Leu Gly Asn Thr Arg Pro Gly Asp Gly Pro
195 200 205

Leu Phe Lys Gly Arg Gly Leu Leu Gln Ile Thr Gly Arg Leu Asn Tyr
210 215 220

Val Lys Cys Gln Val Tyr Leu Arg Glu Lys Leu Lys Asp Pro Thr Phe
225 230 235 240

Asp Ile Thr Ser Ser Val Thr Cys Ala Gln Gln Leu Ser Glu Ser Pro
245 250 255

Leu Leu Ala Ala Leu Ala Ser Gly Tyr Phe Trp Arg Phe Ile Lys Pro
260 265 270

Lys Leu Asn Glu Thr Ala Asp Lys Asp Asp Ile Tyr Trp Val Ser Val
275 280 285

Tyr Val Asn Gly Tyr Ala Lys Gln Ala Asn Pro Tyr Tyr Pro Asn Arg
290 295 300

Asp Lys Glu Pro Asn His Met Lys Glu Arg Val Gln Met Leu Ala Val
305 310 315 320

Thr Lys Lys Ala His Gly Ile Val
325

<210> SEQ ID NO 87
<211> LENGTH: 327
<212> TYPE: PRT

<213> ORGANISM: unknown
<220> FEATURE:
<223> OTHER INFORMATION: OBPgpLYS

<400> SEQUENCE: 87

```
Lys Asn Ser Glu Lys Asn Ala Ser Ile Ile Met Ser Ile Gln Arg Thr
1               5                   10                  15

Leu Ala Ser Leu Ser Leu Tyr Gly Gly Arg Ile Asp Gly Leu Phe Gly
            20                  25                  30

Glu Lys Cys Arg Gly Ala Ile Ile Leu Met Leu Asn Lys Val Tyr Pro
        35                  40                  45

Asn Phe Ser Thr Asn Lys Leu Pro Ser Asn Thr Tyr Glu Ala Glu Ser
    50                  55                  60

Val Phe Thr Phe Leu Gln Thr Ala Leu Ala Gly Val Gly Leu Tyr Thr
65                  70                  75                  80

Ile Thr Ile Asp Gly Lys Trp Gly Gly Thr Ser Gln Gly Ala Ile Asp
                85                  90                  95

Ala Leu Val Lys Ser Tyr Arg Gln Ile Thr Glu Ala Glu Arg Ala Gly
            100                 105                 110

Ser Thr Leu Pro Leu Gly Leu Ala Thr Val Met Ser Lys His Met Ser
        115                 120                 125

Ile Glu Gln Leu Arg Ala Met Leu Pro Thr Asp Arg Gln Gly Tyr Ala
    130                 135                 140

Glu Val Tyr Ile Asp Pro Leu Asn Glu Thr Met Asp Ile Phe Glu Ile
145                 150                 155                 160

Asn Thr Pro Leu Arg Ile Ala His Phe Met Ala Gln Ile Leu His Glu
                165                 170                 175

Thr Ala Cys Phe Lys Tyr Thr Glu Glu Leu Ala Ser Gly Lys Ala Tyr
            180                 185                 190

Glu Gly Arg Ala Asp Leu Gly Asn Thr Arg Pro Gly Asp Gly Pro Leu
        195                 200                 205

Phe Lys Gly Arg Gly Leu Leu Gln Ile Thr Gly Arg Leu Asn Tyr Val
    210                 215                 220

Lys Cys Gln Val Tyr Leu Arg Glu Lys Leu Lys Asp Pro Thr Phe Asp
225                 230                 235                 240

Ile Thr Ser Ser Val Thr Cys Ala Gln Gln Leu Ser Glu Ser Pro Leu
                245                 250                 255

Leu Ala Ala Leu Ala Ser Gly Tyr Phe Trp Arg Phe Ile Lys Pro Lys
            260                 265                 270

Leu Asn Glu Thr Ala Asp Lys Asp Asp Ile Tyr Trp Val Ser Val Tyr
        275                 280                 285

Val Asn Gly Tyr Ala Lys Gln Ala Asn Pro Tyr Tyr Pro Asn Arg Asp
    290                 295                 300

Lys Glu Pro Asn His Met Lys Glu Arg Val Gln Met Leu Ala Val Thr
305                 310                 315                 320

Lys Lys Ala His Gly Ile Val
                325
```

<210> SEQ ID NO 88
<211> LENGTH: 336
<212> TYPE: PRT
<213> ORGANISM: unknown
<220> FEATURE:
<223> OTHER INFORMATION: OBPgpLYS derivative with His-tag

<400> SEQUENCE: 88

-continued

```
Met Lys Asn Ser Glu Lys Asn Ala Ser Ile Ile Met Ser Ile Gln Arg
1               5                   10                  15

Thr Leu Ala Ser Leu Ser Leu Tyr Gly Gly Arg Ile Asp Gly Leu Phe
            20                  25                  30

Gly Glu Lys Cys Arg Gly Ala Ile Ile Leu Met Leu Asn Lys Val Tyr
        35                  40                  45

Pro Asn Phe Ser Thr Asn Lys Leu Pro Ser Asn Thr Tyr Glu Ala Glu
    50                  55                  60

Ser Val Phe Thr Phe Leu Gln Thr Ala Leu Ala Gly Val Gly Leu Tyr
65                  70                  75                  80

Thr Ile Thr Ile Asp Gly Lys Trp Gly Gly Thr Ser Gln Gly Ala Ile
                85                  90                  95

Asp Ala Leu Val Lys Ser Tyr Arg Gln Ile Thr Glu Ala Glu Arg Ala
            100                 105                 110

Gly Ser Thr Leu Pro Leu Gly Leu Ala Thr Val Met Ser Lys His Met
        115                 120                 125

Ser Ile Glu Gln Leu Arg Ala Met Leu Pro Thr Asp Arg Gln Gly Tyr
    130                 135                 140

Ala Glu Val Tyr Ile Asp Pro Leu Asn Glu Thr Met Asp Ile Phe Glu
145                 150                 155                 160

Ile Asn Thr Pro Leu Arg Ile Ala His Phe Met Ala Gln Ile Leu His
                165                 170                 175

Glu Thr Ala Cys Phe Lys Tyr Thr Glu Glu Leu Ala Ser Gly Lys Ala
            180                 185                 190

Tyr Glu Gly Arg Ala Asp Leu Gly Asn Thr Arg Pro Gly Asp Gly Pro
        195                 200                 205

Leu Phe Lys Gly Arg Gly Leu Leu Gln Ile Thr Gly Arg Leu Asn Tyr
    210                 215                 220

Val Lys Cys Gln Val Tyr Leu Arg Glu Lys Leu Lys Asp Pro Thr Phe
225                 230                 235                 240

Asp Ile Thr Ser Ser Val Thr Cys Ala Gln Gln Leu Ser Glu Ser Pro
                245                 250                 255

Leu Leu Ala Ala Leu Ala Ser Gly Tyr Phe Trp Arg Phe Ile Lys Pro
            260                 265                 270

Lys Leu Asn Glu Thr Ala Asp Lys Asp Asp Ile Tyr Trp Val Ser Val
        275                 280                 285

Tyr Val Asn Gly Tyr Ala Lys Gln Ala Asn Pro Tyr Tyr Pro Asn Arg
    290                 295                 300

Asp Lys Glu Pro Asn His Met Lys Glu Arg Val Gln Met Leu Ala Val
305                 310                 315                 320

Thr Lys Lys Ala His Gly Ile Val Lys Gly His His His His His His
                325                 330                 335
```

<210> SEQ ID NO 89
<211> LENGTH: 1011
<212> TYPE: DNA
<213> ORGANISM: unknown
<220> FEATURE:
<223> OTHER INFORMATION: OBPgpLYS derivative with additional His-tag

<400> SEQUENCE: 89

```
atgaaaaata gcgagaagaa tgcatcgata attatgtcga tacagagaac gctcgcttca      60

ctctcactct atggaggccg catcgacggc ctctttggag agaagtgtcg tggggctatc     120

atcttgatgc tgaataaggt ctatcctaat ttcagcacca acaaacttcc gagtaacaca     180
```

-continued

```
tatgaagcgg aatccgtgtt cacgtttctc cagactgctt tggctggtgt tggtctttat    240

accattacta ttgatggtaa atggggtggt acttctcaag gtgctattga cgccctcgtc    300

aagtcttacc gtcaaattac cgaagcggag cgagctgggt cgacgttgcc attaggtctt    360

gctactgtga tgtctaagca tatgtctatt gaacagttga gagcaatgct ccctaccgat    420

agacaaggat atgctgaagt ttatatcgat cctttaaatg agacgatgga tatatttgaa    480

ataaatactc cattacgaat tgctcatttc atggcccaaa tcctccacga aacggcgtgt    540

tttaaatata ccgaagaact ggcgagcggt aaggcttatg agggtcgtgc tgatttaggt    600

aatactcgac caggtgatgg accactgttt aaaggtcgtg gattattaca aattaccggg    660

cgactgaatt atgtgaaatg ccaagtgtat ttgagagaga agttaaagga ccctactttc    720

gacattacgt cgtctgtaac ttgtgcccaa cagctctccg aaagtccact tcttgctgca    780

ttggcatcgg gctacttctg gagattcatc aaacctaaac tcaatgaaac ggctgataaa    840

gacgatatct attgggtttc tgtttatgtc aatggttacg ctaaacaagc gaatccttat    900

taccctaacc gggataagga acccaaccat atgaaagaac gtgtccaaat gcttgcagtg    960

acaaagaaag cacacggaat agttaagggt catcatcacc atcaccattg a            1011


<210> SEQ ID NO 90
<211> LENGTH: 72
<212> TYPE: DNA
<213> ORGANISM: unknown
<220> FEATURE:
<223> OTHER INFORMATION: antimicrobial peptide ascaphine

<400> SEQUENCE: 90

ggtatcaaag attggatcaa aggcgcagcg aaaaaactga tcaaaaccgt tgcctctcac     60

attgctaacc ag                                                          72


<210> SEQ ID NO 91
<211> LENGTH: 51
<212> TYPE: DNA
<213> ORGANISM: unknown
<220> FEATURE:
<223> OTHER INFORMATION: antimicrobial peptide apidaecine

<400> SEQUENCE: 91

gcgaaccgtc cggtctacat cccaccgcca cgtccaccgc acccacgtct g               51


<210> SEQ ID NO 92
<211> LENGTH: 117
<212> TYPE: DNA
<213> ORGANISM: unknown
<220> FEATURE:
<223> OTHER INFORMATION: antimicrobial peptide Sarcotoxin IA

<400> SEQUENCE: 92

ggatggctca aaaagattgg caagaaaatc gagcgagtcg gtcagcatac gcgtgatgca     60

actatccagg gtttaggtat cgcacagcaa gcagctaatg tagcagctac tgctcgg       117


<210> SEQ ID NO 93
<211> LENGTH: 87
<212> TYPE: DNA
<213> ORGANISM: unknown
<220> FEATURE:
<223> OTHER INFORMATION: antimicrobial peptide SMAP-29

<400> SEQUENCE: 93

cgtggtctgc gtcgcctggg tcgcaaaatt gcgcacggcg tcaaaaaata cggcccgacc     60
```

gtgctgcgca ttatccgcat cgctggt 87

<210> SEQ ID NO 94
<211> LENGTH: 120
<212> TYPE: DNA
<213> ORGANISM: unknown
<220> FEATURE:
<223> OTHER INFORMATION: antimicrobial peptide Cecropin A (A.aegypti)

<400> SEQUENCE: 94
ggctggctga aaaaaattgg caaaaaaatc gaacgcgtgg gccagcacac gcgtgatgca 60
accatccagg gtctgggtat cccacagcag gcagctaacg tagccgcgac tgctcgtggt 120

<210> SEQ ID NO 95
<211> LENGTH: 39
<212> TYPE: DNA
<213> ORGANISM: unknown
<220> FEATURE:
<223> OTHER INFORMATION: antimicrobial peptide Alpha 4

<400> SEQUENCE: 95
ccgaaccgtg caaaacgtgt aatcaccacc ttccgtacc 39

<210> SEQ ID NO 96
<211> LENGTH: 15
<212> TYPE: DNA
<213> ORGANISM: unknown
<220> FEATURE:
<223> OTHER INFORMATION: synthetic peptide

<400> SEQUENCE: 96
ttcttcgtag caccg 15

<210> SEQ ID NO 97
<211> LENGTH: 54
<212> TYPE: DNA
<213> ORGANISM: unknown
<220> FEATURE:
<223> OTHER INFORMATION: antimicropial peptide Artilysin1

<400> SEQUENCE: 97
ggcttcttca tcccggcagt aatcctgccc tccatcgcat tcctgatcgt accg 54

<210> SEQ ID NO 98
<211> LENGTH: 75
<212> TYPE: DNA
<213> ORGANISM: unknown
<220> FEATURE:
<223> OTHER INFORMATION: antimicropial peptide Artilysin2

<400> SEQUENCE: 98
ggcaaaccgg gctggctgat caaaaaggca ctggtattca agaaactgat ccgtcgtccg 60
ctgaagagac tggca 75

<210> SEQ ID NO 99
<211> LENGTH: 57
<212> TYPE: DNA
<213> ORGANISM: unknown
<220> FEATURE:
<223> OTHER INFORMATION: antimicrobial peptide Parasin 1

<400> SEQUENCE: 99
aaaggccgtg gcaagcaggg aggcaaagta cgtgcaaaag caaagacccg ttcctca 57

<210> SEQ ID NO 100
<211> LENGTH: 75
<212> TYPE: DNA
<213> ORGANISM: unknown
<220> FEATURE:
<223> OTHER INFORMATION: antimicrobial peptide Lycotoxin

<400> SEQUENCE: 100
atctggctga ccgcactgaa attcctcggc aaacacgccg caaagaaact ggcaaaacag 60
caattatcca aactg 75

<210> SEQ ID NO 101
<211> LENGTH: 984
<212> TYPE: DNA
<213> ORGANISM: unknown
<220> FEATURE:
<223> OTHER INFORMATION: OBPgpLYS

<400> SEQUENCE: 101
atgaaaaata gcgagaagaa tgcatcgata attatgtcga tacagagaac gctcgcttca 60
ctctcactct atggaggccg catcgacggc ctctttggag agaagtgtcg tggggctatc 120
atcttgatgc tgaataaggt ctatcctaat ttcagcacca acaaacttcc gagtaacaca 180
tatgaagcgg aatccgtgtt cacgtttctc cagactgctt tggctggtgt tggtctttat 240
accattacta ttgatggtaa atggggtggt acttctcaag gtgctattga cgccctcgtc 300
aagtcttacc gtcaaattac cgaagcggag cgagctgggt cgacgttgcc attaggtctt 360
gctactgtga tgtctaagca tatgtctatt gaacagttga gagcaatgct ccctaccgat 420
agacaaggat atgctgaagt ttatatcgat cctttaaatg agacgatgga tatatttgaa 480
ataaatactc cattacgaat tgctcatttc atggcccaaa tcctccacga aacggcgtgt 540
tttaaatata ccgaagaact ggcgagcggt aaggcttatg agggtcgtgc tgatttaggt 600
aatactcgac caggtgatgg accactgttt aaaggtcgtg gattattaca aattaccggg 660
cgactgaatt atgtgaaatg ccaagtgtat ttgagagaga agttaaagga ccctactttc 720
gacattacgt cgtctgtaac ttgtgcccaa cagctctccg aaagtccact tcttgctgca 780
ttggcatcgg gctacttctg gagattcatc aaacctaaac tcaatgaaac ggctgataaa 840
gacgatatct attgggtttc tgtttatgtc aatggttacg ctaaacaagc gaatccttat 900
taccctaacc gggataagga acccaaccat atgaaagaac gtgtccaaat gcttgcagtg 960
acaaagaaag cacacggaat agtt 984

<210> SEQ ID NO 102
<211> LENGTH: 33
<212> TYPE: DNA
<213> ORGANISM: Artificial Sequence
<220> FEATURE:
<223> OTHER INFORMATION: forward primer

<400> SEQUENCE: 102
ggaatgggga gctcctccaa aaatagcgag aag 33

<210> SEQ ID NO 103
<211> LENGTH: 24
<212> TYPE: DNA
<213> ORGANISM: Artificial Sequence
<220> FEATURE:
<223> OTHER INFORMATION: reverse primer

<400> SEQUENCE: 103
aactattccg tgtgctttct ttgt 24

<210> SEQ ID NO 104
<211> LENGTH: 48
<212> TYPE: DNA
<213> ORGANISM: Artificial Sequence
<220> FEATURE:
<223> OTHER INFORMATION: extended forward primer

<400> SEQUENCE: 104
atgggatcct tcttcgtagc accgggctcc tccaaaaata gcgagaag 48

<210> SEQ ID NO 105
<211> LENGTH: 39
<212> TYPE: DNA
<213> ORGANISM: Artificial sequence
<220> FEATURE:
<223> OTHER INFORMATION: forward primer alpha4

<400> SEQUENCE: 105
ttggaatggg gagcccgaac cgtgcaaaac gtgtaatca 39

<210> SEQ ID NO 106
<211> LENGTH: 42
<212> TYPE: DNA
<213> ORGANISM: Artificial Sequence
<220> FEATURE:
<223> OTHER INFORMATION: reverse primer alpha4

<400> SEQUENCE: 106
tatttttgga ggagccggta cggaaggtgg tgattacacg tt 42

<210> SEQ ID NO 107
<211> LENGTH: 39
<212> TYPE: DNA
<213> ORGANISM: Artificial Sequence
<220> FEATURE:
<223> OTHER INFORMATION: forward primer artilys1

<400> SEQUENCE: 107
ttatgggctt cttcatcccg gcagtaatcc tgccctcca 39

<210> SEQ ID NO 108
<211> LENGTH: 53
<212> TYPE: DNA
<213> ORGANISM: Artificial Sequence
<220> FEATURE:
<223> OTHER INFORMATION: reverse primer artilys1

<400> SEQUENCE: 108
tatttttgga tctgccgccc ggtacgatca ggaatgcgat ggagggcagg att 53

<210> SEQ ID NO 109
<211> LENGTH: 47
<212> TYPE: DNA
<213> ORGANISM: Artificial Sequence
<220> FEATURE:
<223> OTHER INFORMATION: forward primer artilys2

<400> SEQUENCE: 109
ttatgggcaa accgggctgg ctgatcaaaa ggcactggta ttcaaga 47

<210> SEQ ID NO 110
<211> LENGTH: 64
<212> TYPE: DNA

<213> ORGANISM: Artificial Sequence
<220> FEATURE:
<223> OTHER INFORMATION: revers primer artilys2

<400> SEQUENCE: 110
tatttttgga tctgccgcct gccagtctct tcagcggacg acggatcagt ttcttgaata 60
ccag 64

<210> SEQ ID NO 111
<211> LENGTH: 48
<212> TYPE: DNA
<213> ORGANISM: Artificial Sequence
<220> FEATURE:
<223> OTHER INFORMATION: forward primer Parasin1

<400> SEQUENCE: 111
ttggaatggg gagcaaaggc cgtggcaagc agggaggcaa agtacgtg 48

<210> SEQ ID NO 112
<211> LENGTH: 51
<212> TYPE: DNA
<213> ORGANISM: Artificial Sequence
<220> FEATURE:
<223> OTHER INFORMATION: reverse primer Parasin1

<400> SEQUENCE: 112
tatttttgga ggagcctgag gaacgggtct ttgcttttgc acgtactttg c 51

<210> SEQ ID NO 113
<211> LENGTH: 55
<212> TYPE: DNA
<213> ORGANISM: Artificial Sequence
<220> FEATURE:
<223> OTHER INFORMATION: forward primer Lycotoxin

<400> SEQUENCE: 113
ggaatgggga gcatctggct gaccgcactg aaattcctcg gcaaacacgc cgcaa 55

<210> SEQ ID NO 114
<211> LENGTH: 60
<212> TYPE: DNA
<213> ORGANISM: Artificial Sequence
<220> FEATURE:
<223> OTHER INFORMATION: reverse primer Lycotoxin

<400> SEQUENCE: 114
tatttttgga ggagcccagt ttggataatt gctgttttgc cagtttcttt gcggcgtgtt 60

<210> SEQ ID NO 115
<211> LENGTH: 339
<212> TYPE: PRT
<213> ORGANISM: unknown
<220> FEATURE:
<223> OTHER INFORMATION: PKOBPgpLYS derivative

<400> SEQUENCE: 115

Met Gly Ser Lys Arg Lys Lys Arg Lys Lys Arg Lys Lys Asn Ser Glu
1 5 10 15

Lys Asn Ala Ser Ile Ile Met Ser Ile Gln Arg Thr Leu Ala Ser Leu
20 25 30

Ser Leu Tyr Gly Gly Arg Ile Asp Gly Leu Phe Gly Glu Lys Cys Arg
35 40 45

Gly Ala Ile Ile Leu Met Leu Asn Lys Val Tyr Pro Asn Phe Ser Thr
50 55 60

```
Asn Lys Leu Pro Ser Asn Thr Tyr Glu Ala Glu Ser Val Phe Thr Phe
65                  70                  75                  80

Leu Gln Thr Ala Leu Ala Gly Val Gly Leu Tyr Thr Ile Thr Ile Asp
                85                  90                  95

Gly Lys Trp Gly Gly Thr Ser Gln Gly Ala Ile Asp Ala Leu Val Lys
            100                 105                 110

Ser Tyr Arg Gln Ile Thr Glu Ala Glu Arg Ala Gly Ser Thr Leu Pro
        115                 120                 125

Leu Gly Leu Ala Thr Val Met Ser Lys His Met Ser Ile Glu Gln Leu
    130                 135                 140

Arg Ala Met Leu Pro Thr Asp Arg Gln Gly Tyr Ala Glu Val Tyr Ile
145                 150                 155                 160

Asp Pro Leu Asn Glu Thr Met Asp Ile Phe Glu Ile Asn Thr Pro Leu
                165                 170                 175

Arg Ile Ala His Phe Met Ala Gln Ile Leu His Glu Thr Ala Cys Phe
            180                 185                 190

Lys Tyr Thr Glu Glu Leu Ala Ser Gly Lys Ala Tyr Glu Gly Arg Ala
        195                 200                 205

Asp Leu Gly Asn Thr Arg Pro Gly Asp Gly Pro Leu Phe Lys Gly Arg
    210                 215                 220

Gly Leu Leu Gln Ile Thr Gly Arg Leu Asn Tyr Val Lys Cys Gln Val
225                 230                 235                 240

Tyr Leu Arg Glu Lys Leu Lys Asp Pro Thr Phe Asp Ile Thr Ser Ser
                245                 250                 255

Val Thr Cys Ala Gln Gln Leu Ser Glu Ser Pro Leu Leu Ala Ala Leu
            260                 265                 270

Ala Ser Gly Tyr Phe Trp Arg Phe Ile Lys Pro Lys Leu Asn Glu Thr
        275                 280                 285

Ala Asp Lys Asp Asp Ile Tyr Trp Val Ser Val Tyr Val Asn Gly Tyr
    290                 295                 300

Ala Lys Gln Ala Asn Pro Tyr Tyr Pro Asn Arg Asp Lys Glu Pro Asn
305                 310                 315                 320

His Met Lys Glu Arg Val Gln Met Leu Ala Val Thr Lys Lys Ala His
                325                 330                 335

Gly Ile Val


<210> SEQ ID NO 116
<211> LENGTH: 347
<212> TYPE: PRT
<213> ORGANISM: unknown
<220> FEATURE:
<223> OTHER INFORMATION: PKOBPgpLYS derivative with additional His-tag

<400> SEQUENCE: 116

Met Gly Ser Lys Arg Lys Lys Arg Lys Lys Arg Lys Lys Asn Ser Glu
1               5                   10                  15

Lys Asn Ala Ser Ile Ile Met Ser Ile Gln Arg Thr Leu Ala Ser Leu
            20                  25                  30

Ser Leu Tyr Gly Gly Arg Ile Asp Gly Leu Phe Gly Glu Lys Cys Arg
        35                  40                  45

Gly Ala Ile Ile Leu Met Leu Asn Lys Val Tyr Pro Asn Phe Ser Thr
    50                  55                  60

Asn Lys Leu Pro Ser Asn Thr Tyr Glu Ala Glu Ser Val Phe Thr Phe
65                  70                  75                  80
```

```
Leu Gln Thr Ala Leu Ala Gly Val Gly Leu Tyr Thr Ile Thr Ile Asp
                85                  90                  95

Gly Lys Trp Gly Gly Thr Ser Gln Gly Ala Ile Asp Ala Leu Val Lys
            100                 105                 110

Ser Tyr Arg Gln Ile Thr Glu Ala Glu Arg Ala Gly Ser Thr Leu Pro
        115                 120                 125

Leu Gly Leu Ala Thr Val Met Ser Lys His Met Ser Ile Glu Gln Leu
    130                 135                 140

Arg Ala Met Leu Pro Thr Asp Arg Gln Gly Tyr Ala Glu Val Tyr Ile
145                 150                 155                 160

Asp Pro Leu Asn Glu Thr Met Asp Ile Phe Glu Ile Asn Thr Pro Leu
                165                 170                 175

Arg Ile Ala His Phe Met Ala Gln Ile Leu His Glu Thr Ala Cys Phe
            180                 185                 190

Lys Tyr Thr Glu Glu Leu Ala Ser Gly Lys Ala Tyr Glu Gly Arg Ala
        195                 200                 205

Asp Leu Gly Asn Thr Arg Pro Gly Asp Gly Pro Leu Phe Lys Gly Arg
    210                 215                 220

Gly Leu Leu Gln Ile Thr Gly Arg Leu Asn Tyr Val Lys Cys Gln Val
225                 230                 235                 240

Tyr Leu Arg Glu Lys Leu Lys Asp Pro Thr Phe Asp Ile Thr Ser Ser
                245                 250                 255

Val Thr Cys Ala Gln Gln Leu Ser Glu Ser Pro Leu Leu Ala Ala Leu
            260                 265                 270

Ala Ser Gly Tyr Phe Trp Arg Phe Ile Lys Pro Lys Leu Asn Glu Thr
        275                 280                 285

Ala Asp Lys Asp Asp Ile Tyr Trp Val Ser Val Tyr Val Asn Gly Tyr
    290                 295                 300

Ala Lys Gln Ala Asn Pro Tyr Tyr Pro Asn Arg Asp Lys Glu Pro Asn
305                 310                 315                 320

His Met Lys Glu Arg Val Gln Met Leu Ala Val Thr Lys Lys Ala His
                325                 330                 335

Gly Ile Val Lys Gly His His His His His His
            340                 345
```

<210> SEQ ID NO 117
<211> LENGTH: 18
<212> TYPE: PRT
<213> ORGANISM: unknown
<220> FEATURE:
<223> OTHER INFORMATION: antimicrobial peptide Ranalexin

<400> SEQUENCE: 117

```
Phe Leu Gly Gly Leu Ile Val Pro Ala Met Ile Cys Ala Val Thr Lys
1               5                   10                  15

Lys Cys
```

<210> SEQ ID NO 118
<211> LENGTH: 27
<212> TYPE: PRT
<213> ORGANISM: unknown
<220> FEATURE:
<223> OTHER INFORMATION: peptide stretch WLBU2 variant

<400> SEQUENCE: 118

```
Lys Arg Trp Val Lys Arg Val Lys Arg Val Lys Arg Trp Val Lys Arg
1               5                   10                  15
```

-continued

```
Val Val Arg Val Val Lys Arg Trp Val Lys Arg
            20                  25


<210> SEQ ID NO 119
<211> LENGTH: 26
<212> TYPE: PRT
<213> ORGANISM: unknown
<220> FEATURE:
<223> OTHER INFORMATION: antimicrobial peptide Melittin

<400> SEQUENCE: 119

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```